(12) United States Patent
Thompson, III et al.

(10) Patent No.: US 7,745,470 B2
(45) Date of Patent: Jun. 29, 2010

(54) ISOPHTHALATES AS BETA-SECRETASE INHIBITORS

(75) Inventors: Lorin A. Thompson, III, Higganum, CT (US); Kenneth M. Boy, Durham, CT (US); Jianliang Shi, Hamden, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 960 days.

(21) Appl. No.: 11/370,728

(22) Filed: Mar. 8, 2006

(65) Prior Publication Data

US 2006/0229309 A1 Oct. 12, 2006

Related U.S. Application Data

(60) Provisional application No. 60/660,432, filed on Mar. 10, 2005.

(51) Int. Cl.
*A61K 31/42* (2006.01)
*C07D 263/30* (2006.01)

(52) U.S. Cl. .................................. 514/374; 548/235
(58) Field of Classification Search ............. 514/374; 548/235
See application file for complete search history.

(56) References Cited

FOREIGN PATENT DOCUMENTS

| WO | WO 02/02512 | 1/2002 |
|---|---|---|
| WO | WO 02/02518 | 1/2002 |
| WO | WO 2004/043916 | 5/2004 |
| WO | WO 2005/016876 A2 * | 2/2005 |

OTHER PUBLICATIONS

Cecil Textbook of Medicine, 20th edition (1996), vol. 2, pp. 2050-2057.*
Cecil Textbook of Medicine, 20th Edition (1996), vol. 2, pp. 1992-1996.*
FDA mulls drug to slow late-stage Alzheimer's [online], [retrieved on Sep. 23, 2003]. Retrived from the internet, URL<http://www.cnn.com/2003/HEALTH/conditions/09/24/alzheimers.drug.ap/index.html>.*
Coburn, C.A., et al., "Identification of a Small Molecule Nonpeptide Active Site β-Secretase Inhibitor That Displays a Nontraditional Binding Mode for Aspartyl Proteases", *J. Med. Chem.* (2004) 47 (25): 6117-6119.
Hussain, I. et al. "Identification of a Novel Aspartic Protease (Asp 2) as β-Secretase", *Mol. Cell. Neurosci,* (1999) 14: 419-427.
Horn, R.K., et al., "Design and Synthesis of Hydroxyethylene-Bses Peptidomimetic Inhibitors of Human β-Secretase", *J. Med. Chem.* (2004) 47 (1): 158-164.
Lin, X. et al., "Human aspartic protease memapsin 2 cleaves the β-secretase site of β-amyloid precursor protein", Proceedings of the National Academy of Sciences of the USA, (2000) 97: 1456-1460.
Luo, Y., et al., "Mice deficient in BACE1, the Alzheimer's β-secretase, have normal phenotype and abolished β-amyloid generation", *Nature Neuroscience* (2001) 4: 231-232.
Roberds, S.L. et al., "BACE knockout mice are healthy despite lacking the primary β-secretase activity in brain: implications for Alzheimer's disease therapeutics", *Human Molecular Genetics* (2001) 10: 1317-1324.
Seiffert, D.; et al., "Presenilin-1 and -2 are molecular targets for γ-secretase inhibitors", *J. Biol. Chem.* (2000) 275, 34086-34091.
Selkoe, D. J., "Alzheimer's Disease: Genes, Proteins, and Therapy", *Physiol. Rev.* (2001) 81, 741-766.
Selkoe, D. J., "Biochemical Analyses of Alzheimer's Brain Lesions lead to the Identification of αβ and its Precursor", *Ann. Rev. Cell Biol.* (1994) 10: 373-403.
Sinha, S., et al., "Purification and cloning of amyloid precursor protein β-secretase from human brain", *Nature* (London) (1999) 402: 537-540.
Stachet, S.J., et al., "Structure-Based Design of Potent and Selective Cell-Permeable Inhibitors of Human β-secretase (BASE-1)", *J. of Med. Chem.* (2004) 47 (26): 6447-6450.
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.
Walsh, D. M., et al., "Naturally secreted oligomers of amyloid β protein potently inhibit hippocampal long-term potentiation in vivo", *Nature* (2002) 416, 535-539.
Wolfe, M. S., "Secretase Targets for Alzheimer's Disease: Identification and Therapeutic Potential", *J. Med. Chem.* (2001) 44, 2039-2060.
Yan, R. et al., "Membrane-anchored aspartyl protease with Alzheimer's disease β-secretase activity", *Nature* (1999) 402: 533-537.

* cited by examiner

*Primary Examiner*—Rebecca L Anderson
(74) *Attorney, Agent, or Firm*—John F. Levis; Aldo A. Algieri

(57) ABSTRACT

There is provided a series of substituted isophthalates of formula (I)

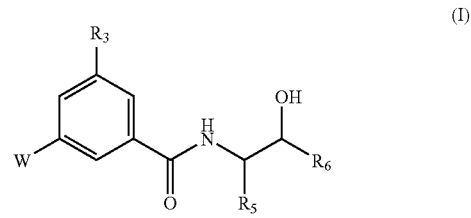

(I)

or a stereoisomer thereof; or a pharmaceutically acceptable salt thereof, wherein W, $R_3$, $R_5$ and $R_6$ as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

2 Claims, No Drawings

ISOPHTHALATES AS BETA-SECRETASE INHIBITORS

CROSS-REFERENCE TO RELATED APPLICATIONS

This is a non-provisional application which claims the benefit of U.S. Provisional Application No. 60/660,432 filed Mar. 10, 2005.

FIELD OF THE DISCLOSURE

This patent application provides novel isophthalates compounds having drug and bio-affecting properties, their pharmaceutical compositions and method of use. In particular, the disclosure is concerned with a series of novel isophthalates which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.*, 1994, 10: 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms thaFt may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al., (1999) *Nature (London)*, 402: 537-540; Vassar, R., et al., (1999) *Science (Washington, D.C.)*, 286: 735-741; Walsh, D. M. et al., (2002); Wolfe, M. S. (2001); Yan, R. et al., (1999) *Nature (London)*, 402: 533-537].

Removal of BACE activity in mice by gene targeting completely abolishes Aβ production [see Luo, Y., et al., (2001) *Nature Neuroscience*, 4: 231-232; Roberds, S. L. et al.,(2001) *Human Molecular Genetics*, 10: 1317-1324].

BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

International patent application WO 2004/043916, published May 27, 2004, discloses phenylcarboxamide derivatives as beta secretase inhibitors. Related compounds of this type were reported by Stachet et al. in the *Journal of Medicinal Chemistry* (2004) 47 (26): 6447 and Coburn et al. in the *Journal of Medicinal Chemistry* (2004) 47 (25): 6117. Isophthalate derivatives substituted with a number of disubstituted acyclic amine fragments have been disclosed in a number of International PCT publications, including International patent applications WO 2002/02512 and WO 2002/02518, both published Jan. 10, 2002. Compounds of this type were also reported by Horn et al. in the *Journal of Medicinal Chemistry* (2004) 47 (1): 158.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of isophthalate derivatives having the formula (I)

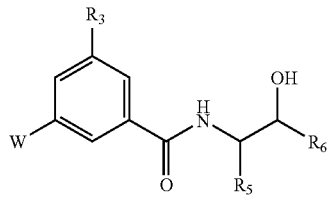

or a stereoisomer; or a pharmaceutically acceptable salt thereof, wherein $R_3$, $R_5$, $R_6$ and W are as defined below are effective inhibitors of the production of βamyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of formula (I), their pharmaceutical formulations, and their use in inhibiting β-AP production in patients suffering from or susceptible to AD or other disorders resulting from β-AP accumulation in brain tissue. The compounds of formula (I) which include stereoisomers and non-toxic pharmaceutically acceptable salts thereof have the following formula and meanings:

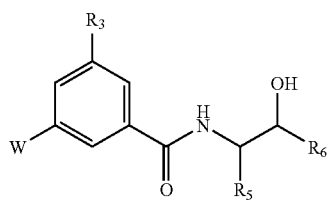

wherein
W is —(CO)—$NR_1R_2$, —O—$C_{1-6}$alkyl, —O—$C_{3-6}$cycloalkyl, or —O—$C_{3-6}$cycloalkyl ($C_{1-4}$alkyl);
$R_1$ is hydrogen or $C_{1-6}$alkyl;
$R_2$ is $C_{1-6}$alkyl, $C_{3-6}$alkenyl, $C_{3-6}$cycloalkyl, $C_{3-6}$cycloalkyl ($C_{1-4}$alkyl), phenyl, phenyl($C_{1-4}$alkyl), pyridyl or pyridyl ($C_{1-4}$alkyl) in which said phenyl and pyridyl are optionally substituted with the group selected from $C_{1-4}$alkyl, fluoro$C_{1-4}$alkyl, trifluoro $C_{1-4}$alkyl, $C_{1-4}$alkoxy, halogen and CN; or $R_1$ and $R_2$ are joined together with the nitrogen to form a 5- or 6-membered ring optionally substituted by $R_4$;

$R_3$ is hydrogen, $C_{1-6}$alkyl, $C_{3-6}$alkenyl, $C_{3-6}$cycloalkyl, $C_{3-6}$cycloalkyl($C_{1-4}$alkyl), —O—$C_{1-6}$alkyl, —O—$C_{3-6}$cycloalkyl, —O—$C_{3-6}$cycloalkyl($C_{1-4}$alkyl), phenyl, pyridyl, oxazole, thiazole, or $NR_{12}$—(CO)—$R_{13}$ in which $R_{12}$ and $R_{13}$ are independently $C_{1-6}$alkyl or are joined together with the nitrogen to form a 5- or 6-membered ring;
$R_4$ is $C_{1-4}$alkyl optionally substituted with the group selected from halogen, OH, $CF_3$, $NH_2$ and $C_{1-4}$alkoxy;
$R_5$ is $C_{1-6}$alkyl, $C_{3-6}$cycloalkyl, $C_{3-6}$cycloalkyl($C_{1-4}$alkyl), phenyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;
$R_6$ is

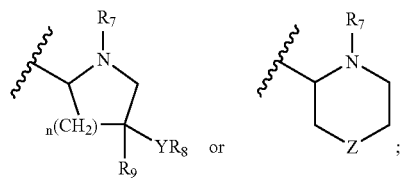

Y is O, $NR_7$ or $S(O)_n$;
Z is $CH_2$, O or S;
n is 1 or 2;
$R_7$ is hydrogen or $C_{1-4}$alkyl; and
$R_8$ and $R_9$ each are independently hydrogen, $C_{1-4}$alkyl, $C_{3-6}$alkenyl, $C_{3-6}$alkynyl, phenyl or pyridyl in which said phenyl and pyridyl are optionally substituted with $C_{1-4}$alkyl, fluoro$C_{1-4}$alkyl, $C_{1-4}$alkoxy, halogen or CN; or $YR_8$ and $R_9$ are joined together with the carbon to which they are attached to form a 5- or 6-membered ring wherein Y is oxygen, and $R_8$ and $R_9$ are —$CH_2(CH_2)_n$—O—;

or a nontoxic pharmaceutically acceptable salt thereof.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, November 2001, 108 (9): 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$alkyl" and "$C_{1-10}$alkyl" denotes alkyl having 1 to 6 or 1 to 10 carbon atoms. Examples of alkyl include, but are not limited to, methyl, ethyl, n-propyl, i-propyl, n-butyl, i-butyl, sec-butyl, t-butyl, pentyl, hexyl, octyl and decyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$cycloalkyl" denotes such as cyclopropyl, cyclobutyl, cyclopentyl and cyclohexyl.

The compounds described herein may have asymmetric centers. An example of a preferred stereochemical configuration is the isomer:

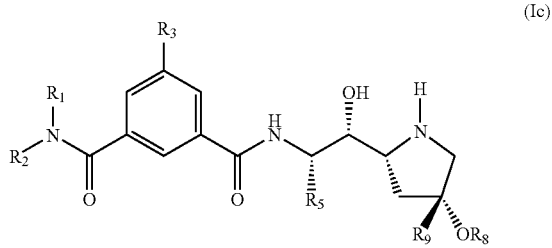

(Ic)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Additionally, the carbon atom to which $R_5$, OH and $OR_8$ are attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, compounds of the invention represented by formula (I) (General Reaction Scheme A) can be prepared by coupling, under standard conditions known to one skilled in the art, a substituted isophthalate of formula 2 and a substituted cyclic diaminopropane. Methods for the synthesis of functionalized isophthalates of formula 2 are known in the art and are disclosed in a number of references including but not limited to those given below. The synthesis of substituted cyclic diaminopropanes is novel and is disclosed in detail in the discussion given below.

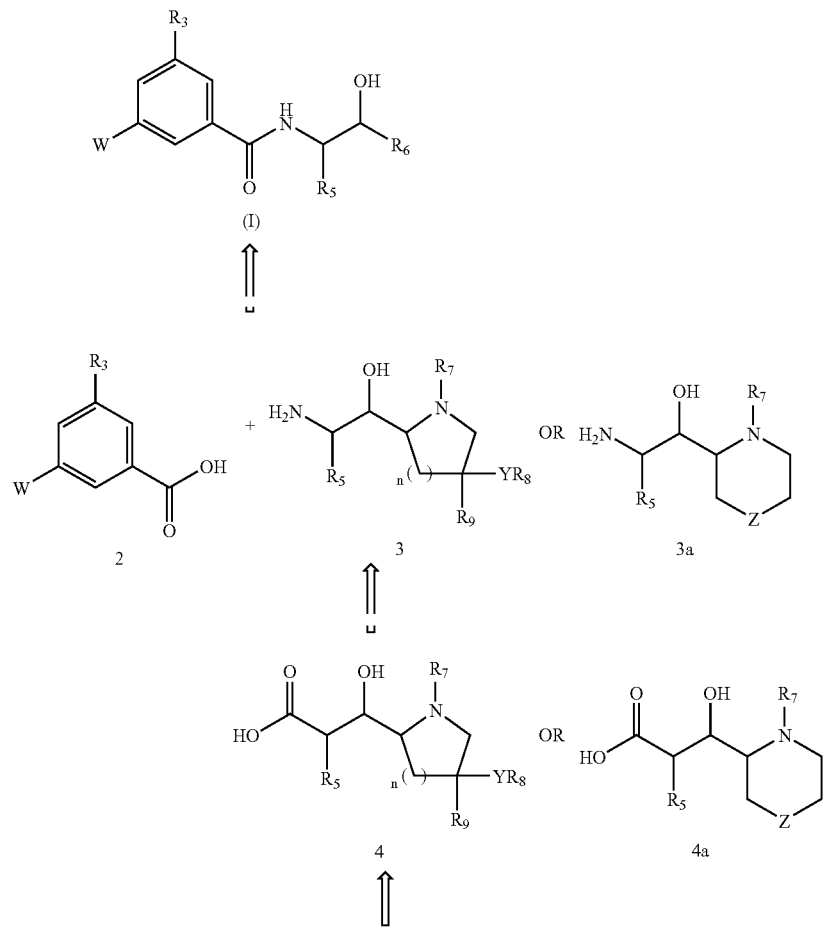

General Reaction Scheme A

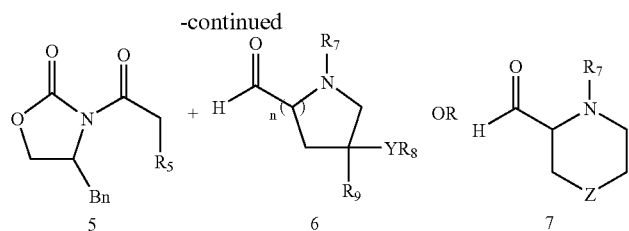

Compounds of the present invention may be also prepared by coupling an isophthalate intermediate such as formula 2a (Scheme B) to the cyclic diaminopropane 3b, followed by elaboration of the isophthalate, followed by deprotection, as is shown in general Reaction Scheme B.

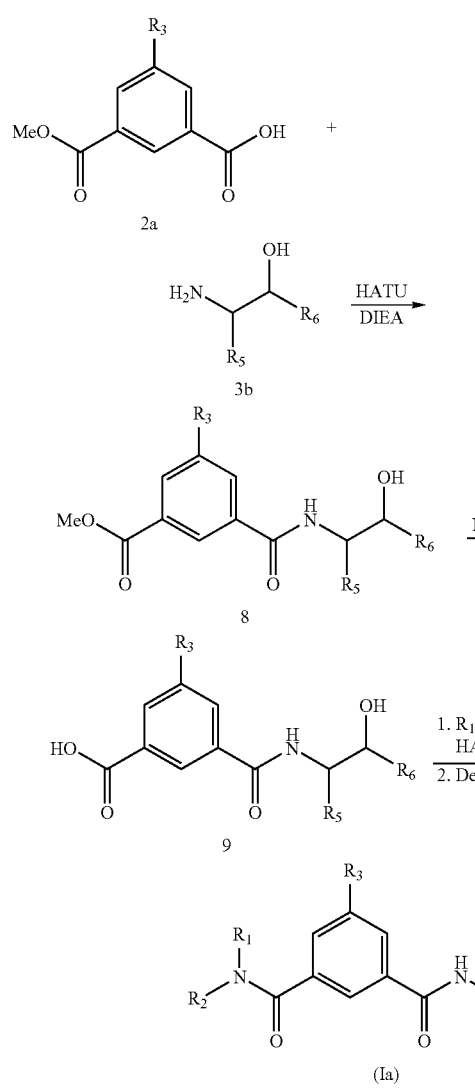

Functionalized isophthalic acid derivatives of formula 15 can be prepared in a number of ways known to those skilled in the art. Synthesis of a large variety of such intermediates is described in international patent application WO 2002/02512

A2. A versatile preparation of these intermediates begins with commercial monomethyl-5-nitroisophthalate. Reduction of the nitro group with catalytic hydrogenation followed by diazotization and trapping with bromine provides the aryl bromide of formula 12. Treatment of this acid with an amine

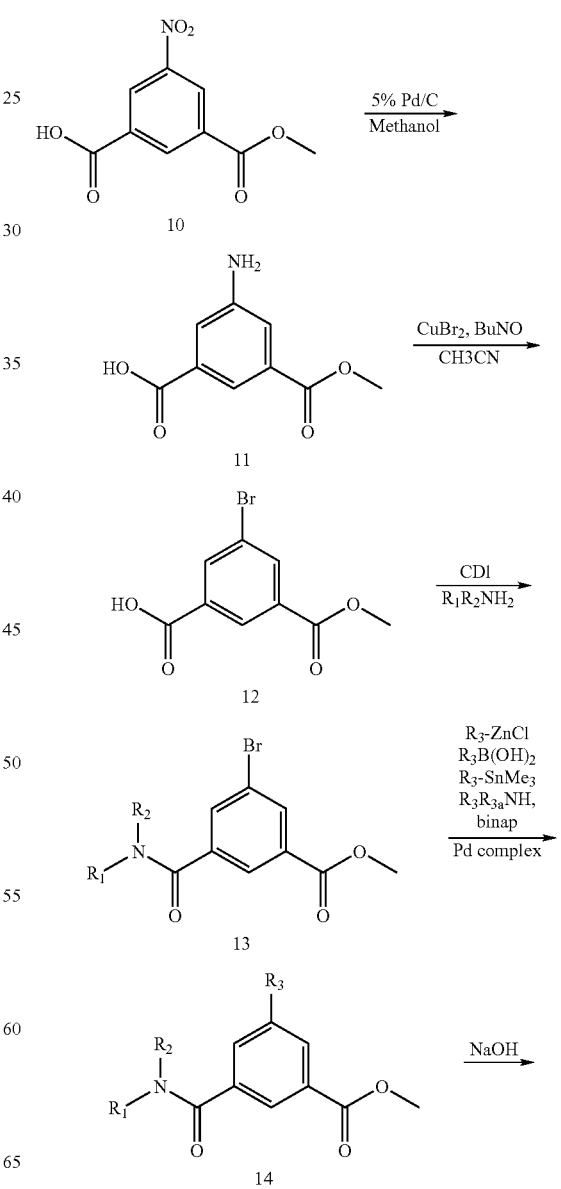

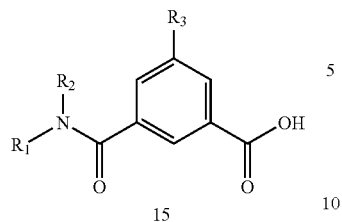

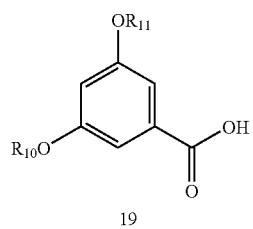

and any of a large number of coupling agents, including carbonyldiimidazole, a carbodiimide coupling agent, or HATU provides the amide product 13. This amide can then be functionalized by coupling any of a number of alkyl, alkenyl, aryl, or heteroaryl metal derivatives, including tin reagents, boronates, or zinc halides using a source of palladium according to the general protocols of Stille, Suzuki, or Negishi respectively. These are standard, extremely versatile reactions known to those skilled in the art. Similarly, a variety of amine-containing substrates can be coupled to the aryl bromide using the protocols of Buchwald and/or Hartwig. Saponification of the resulting esters to the acid affords substituted isophthalic acid derivatives that can be coupled with cyclic diaminopropanes of type 3b.

Additional examples of isophthalates containing ether substituents can be prepared using the general method described in Scheme 2, and additionally demonstrated in international patent application WO 2003/106405. Thus, monoalkylation of methyl 3,5-dihydroxybenzoate provides the monosubstituted ether of formula 17. A second alkylation can then be used to install a second ether group, followed by saponification to the desired acid 19.

Alternatively, one ether substituent and a second substituent can be introduced, as is shown in Scheme 3. Thus, 3-hydroxy-5-nitrobenzoic acid can be alkylated to provide the aryl ether of formula 21. Reduction of the nitro group to the amine provides intermediate 22, which can be alkylated or acylated by ways known to those skilled in the art to provide alkyl amines or amides. Alternatively, the amine can be diazotized and replaced with a halogen such as bromine and then further functionalized by coupling any of a number of alkyl, alkenyl, aryl, or heteroaryl metal derivatives, including tin reagents, boronates, or zinc halides using a source of palladium according to the general protocols of Stille, Suzuki, or Negishi respectively. These are standard, extremely versatile reactions known to those skilled in the art. Similarly, a variety of amine-containing substrates can be coupled to the aryl bromide using the protocols of Buchwald and/or Hartwig. Saponification of the resulting esters of formula 24 to the acid affords substituted isophthalic acid derivatives that can be coupled with cyclic diaminopropanes of type 3b.

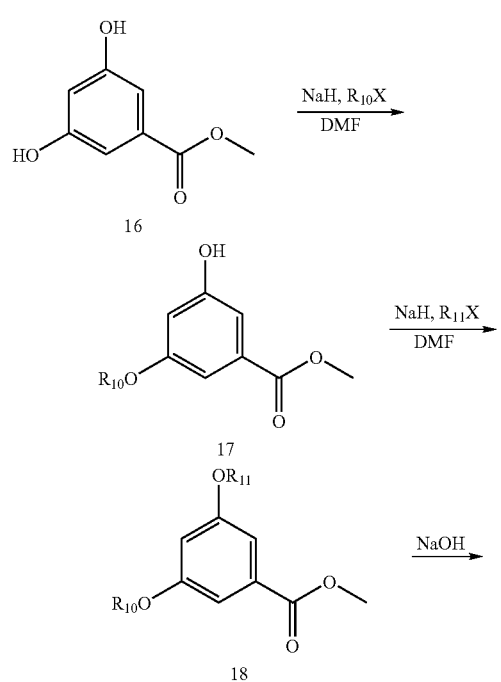

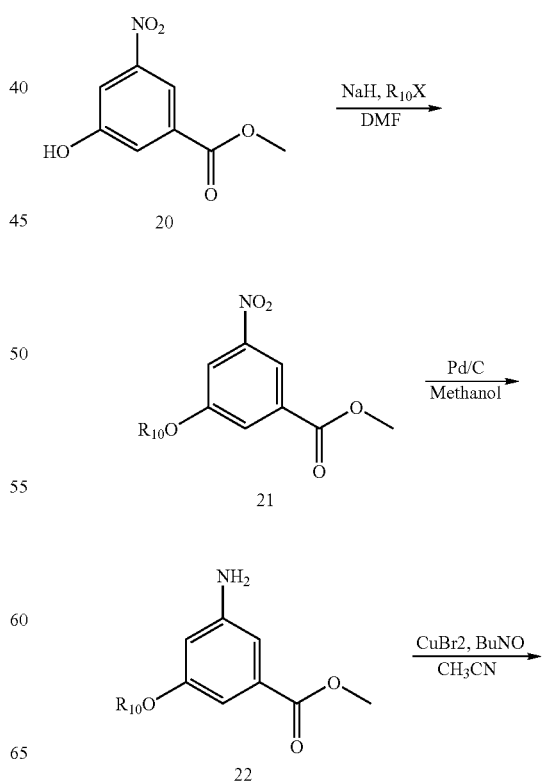

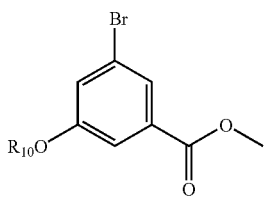

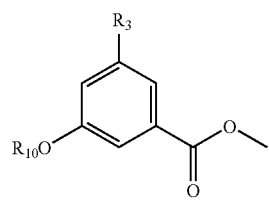

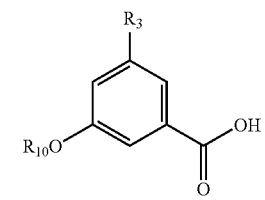

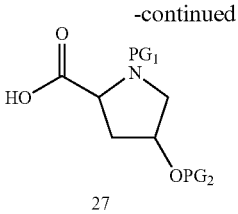

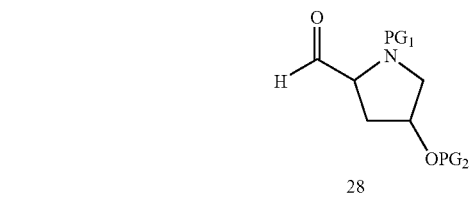

Using similar chemistry, substituted piperidine-based aldehydes of formulas 31a and 31b can be constructed, including the aldehydes derived from pipecolic acid or morpholine 3-carboxylic acid, both items of commerce, according to Scheme 5. Typically the nitrogen protecting group is a Boc group.

Additional examples of the synthesis of substituted isophthalates are provided in International patent application WO 2003/045913.

Cyclic aldehydes can be prepared by a number of methods known to one skilled in the art depending on the cyclic structure employed. A preferred class of cyclic aldehydes can be derived from derivitization of an appropriate commercially-available diastereomer of 4-hydroxy proline. The hydroxy proline acid of formula 26 may be protected using standard conditions know to those skilled in the art. In general, nitrogen atom can be blocked by such protecting groups as Boc or benzyl, the alcohol protected as allyl, benzyl, or other appropriate group, and the carboxylic acid may then be reduced under standard conditions to the alcohol Scheme 4. Ways to effect this transformation include sodium borohydride reduction of the carboxyanhydride, lithium aluminum hydride, or formation of the ester followed by borohydride reduction. The alcohol is then oxidized using a mild oxidizing agent such as the Swern protocol or the Dess-Mertin reagent, or other similar reagents to the desired protected pyrrolidinol aldehyde of formula 28.

Scheme 5

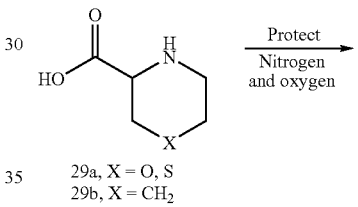

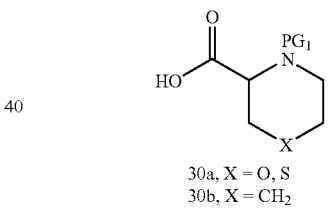

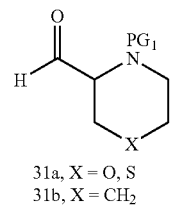

Scheme 6 discloses methods for preparing substituted cyclic hydroxyethyl amines of formula 28 that are used as a coupling partner for isophthalate acids of formula 2. The method relies on the diastereoselective aldol reaction of a suitable enolate equivalent with a substituted cyclic aldehyde. There are a number of methods for the diastereoselective aldol reaction, including those developed by Masamune, (See, for instance, Masamune, S.; Ali, S. A.; Snitman, D. L.; Garvey, D. S. Aldol condensation with increased stereoselectivity through use of an enantioselective chiral enolate. *Angewandte Chemie* 1980, 92, 573-575, and Masamune, S.; Choy, W.; Kerdesky Francis, A. J.; Imperiali, B. Stereoselective aldol condensation. Use of chiral boron enolates. *Journal of the American Chemical Society* 1981, 103, 1566-1568.)

Scheme 4

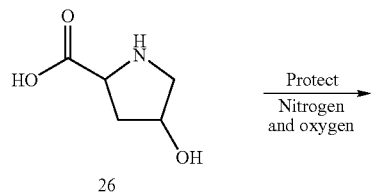

and Heathcock (See Heathcock, C. H. Acyclic stereoselection via the aldol condensation. *ACS Symposium Series* 1982, 185, 55-72, Pirrung, M. C.; Heathcock, C. H. Acyclic stereoselection. 8. A new class of reagents for the highly stereoselective preparation of threo-2-alkyl-3-hydroxycarboxylic acids by the aldol condensation. *Journal of Organic Chemistry* 1980, 45, 1727-1728.). The most commonly used method, and the one described herein, is the method of Evans, reported in a large number of articles including Gage, J. R.; Evans, D. A. Diastereoselective aldol condensation using a chiral oxazolidinone auxiliary. *Organic Syntheses* 1990, 68, 83-91.

The protected cyclic aldehyde of formula 34 is reacted with an enolate according to the method of Evans as referenced above. Thus, (S)-4-benzyl-2-oxazolidinone is acylated as it's lithium salt with a carboxylic acid chloride or with the carboxylate activated as it's pivaloyl mixed carboxyanhydride (see Ho, G.-J.; Mathre, D. J., "Lithium-Initiated Imide Formation. A Simple Method for N-Acylation of 2-Oxazolidinones and Bornane-2,10-Sultam", *Journal of Organic Chemistry*, 1995, 60(7): 2271-2273.) to provide the substituted N-Acyl oxazolidinone of formula 33. This reagent is deprotonated using dibutylboron triflate and a tertiary amine base such as diisopropylethylamine to form the boron enolate, which reacts in a diastereoselective manner to produce the β-hydroxyimide 35. Saponification of the Chiral

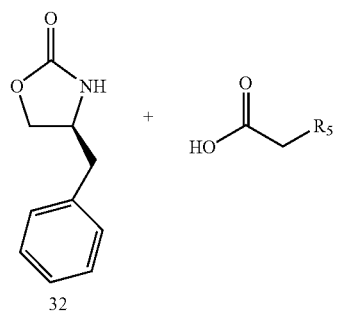

Scheme 6

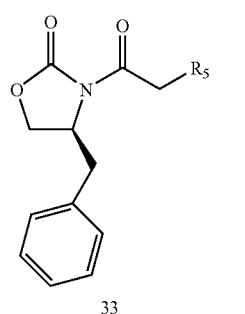

32

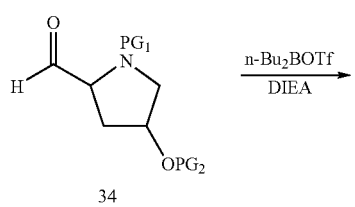

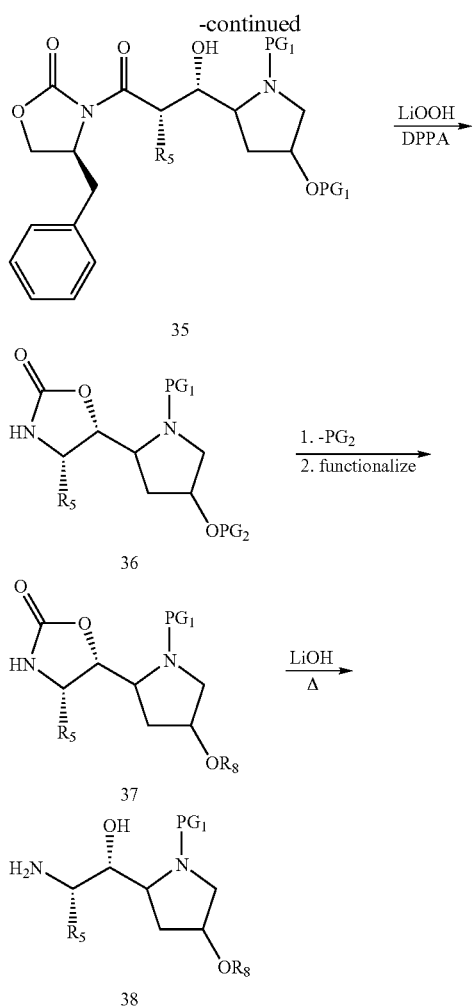

auxiliary under standard conditions (LiOH, $H_2O_2$) followed by Curtius rearrangement initiated by formation of the acyl azide using diphenylphosphorylazide (DPPA) provides the carbamate-protected aminoalcohol of formula 36. Alternatively, the acid can be converted to the acyl azide using an acid activating agent such as the mixed carbonic anhydride formed by isobutyl chloroformate in the presence of an amine base such as N-methyl morpholine followed by treatment with sodium azide. The rearrangement is then cleanly effected by heating the acyl azide in a solvent such as toluene containing an alcohol to trap the intermediate isocyanate. Removal of the alcohol protecting group provides the free alcohol, which may be carried forward itself, or serve as a synthon for other functionality. For example, Mitsunobu inversion with desired phenols and the like provide O-aryl derivatives, O-alkylation provides ether analogs, oxidation to the ketone and Wittig chemistry provides alkenes and, after reduction, substituted alkanes, and other transformations known to those skilled in the art. Mitsunobu inversion of the free alcohol 36 with methane sulfonic acid can also be used to provide a mesylate, which can be displaced with nucleophiles including thiols to provide thioethers. The thioether can be oxidized if desired to the sulfoxide or the sulfone. Cleavage of the carbamate of formula 37 by saponification with aqueous lithium hydroxide provides the functionalized pyrrolidine-containing diaminopropane ready to couple to a substituted isophthalate of formula 2.

Coupling of an isophthalic acid of formula 15 with a protected or unprotected cyclic amino alcohol of formula 38 using methods previously described for making amide bonds, such as HATU and DIEA in DMF, provides a protected or unprotected product, which can be deprotected if necessary to provide the compounds Ie of the present invention (Scheme 7). Preferably, if a protecting group PG is used, it is a Boc group, which is removed by treatment with trifluoroacetic acid in dichloromethane. Also preferred is cleavage of a p-methoxybenzyl or benzhydryl group using hydrogenation in the usual manner.

Scheme 7

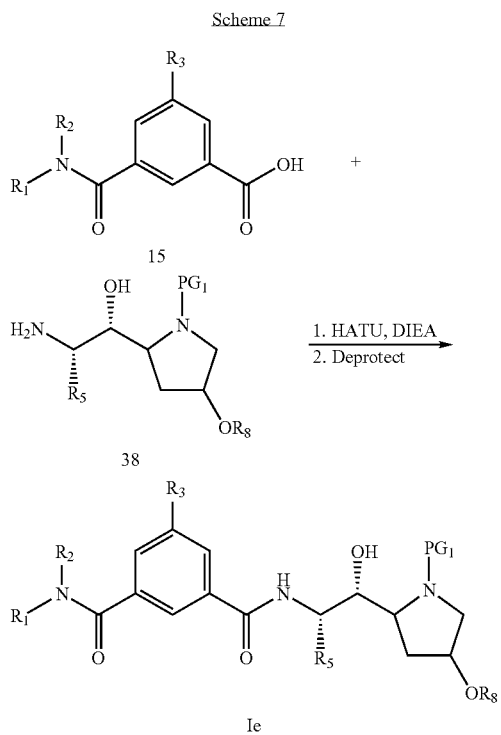

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:
"Ac" for acetate,
"APCI" for atmospheric pressure chemical ionization,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDI" for 1,1'-carbonyldiimidazole,
"CD$_3$OD" for deuteromethanol,
"CDCl$_3$" for deuterochloroform,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"EDC" or "EDCI" for 1-(3-dimethylaminopropyl)-3-ethylcarbodiimide hydrochloride,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"TMSCH$_2$N$_2$" for (trimethylsilyl)diazomethane,
"TMSN$_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable. "LC-MS" refers to high pressure liquid chromatography carried out according to the definition for HPLC with a mass spectrometry detector.

Melting points were determined on a Mel-Temp II apparatus and are uncorrected. IR spectra were obtained on a single-beam Nicolet Nexus FT-IR spectrometer using 16 accumulations at a resolution of 4.00 cm-1 on samples prepared in a pressed disc of KBr or as a film on KBr plates. Proton NMR spectra (300 MHz, referenced to tetramethylsilane) were obtained on a Varian INOUA 300, Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer. HPLC analyses were obtained using a Rainin Dynamax C18 column with UV detection at 223 nm using a standard solvent gradient program as follows:

HPLC solvent conditions: When described as performed under "standard conditions", Samples were dissolved in methanol (1 mg/mL) and run using the following gradient program with a solvent flow rate of 1.0 mL/min.

| Time (min) | Acetonitrile (0.05% TFA) | H$_2$O (0.05% TFA) |
|---|---|---|
| Initial | 10 | 90 |
| 20.0 | 90 | 10 |
| 20-30 | 90 | 10 |

Preparatory HPLC: When described as performed under "standard conditions", Samples (approx. 20 mg) were dissolved in methanol (10 mg/mL) and purified on a 25 mm×50 mm Vydac C18 column with a 5 minute gradient elution from 10% to 100% buffer B in buffer A (buffer A: water containing 0.1% trifluoroacetic acid, buffer B: 10% water, 90% acetonitrile containing 0.1% trifluoroacetic acid) at 10 mL/minute.

Analytical HPLC: When described as "Method A", a sample dissolved in a suitable carrier solvent (methanol, acetonitrile, or the like) was analyzed on an Xterra 3.0×50 mm s7 column with a run time of 3 min and a gradient of 0-100% B over 2 min at a flowrate of 5 mL/min. Absorbance was monitored at 220 μM. Solvent A=0% MeOH/90% water/0.1% TFA and Solvent B=10% water/90% MeOH/0.1% TFA.

Analytical HPLC: When described as "Method B", a sample dissolved in a suitable carrier solvent (methanol, acetonitrile, or the like) was analyzed on an Xterra 3.0×50 mm s7 column with a run time of 4 min and a gradient of 0-100% B over 3 min at a flowrate of 5 mL/min. Absorbance was monitored at 220 μM. Solvent A=0% MeOH/90% water/0.1% TFA and Solvent B=10% water/90% MeOH/0.1% TFA.

Analytical HPLC: When described as "Method C", a sample dissolved in a suitable carrier solvent (methanol, acetonitrile, or the like) was analyzed on an Xterra 4.6×50 mm S5 column with a run time of 4 min and a gradient of 0-100% B over 2 min at a flowrate of 5 mL/min. Absorbance was monitored at 220 μM. Solvent A=0% MeOH/90% water/0.1% TFA and Solvent B=10% water/90% MeOH/0.1% TFA.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation A (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate

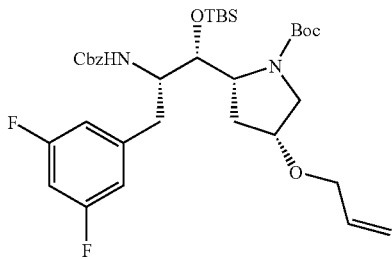

Step A (1): (2R,4R)-1-(tert-butoxycarbonyl)-4-hydroxypyrrolidine-2-carboxylic acid. To a suspension of H-D-Cis-Hyp-OH (purchased from Aldrich, 10.0 g, 76.3 mmol) in 2:1 THF:H$_2$O (125 ml) was added a 2.5 molar aqueous sodium hydroxide solution (42.0 ml). To this mixture was added a solution of Di-tert-butyldicarbonate (22.6 g, 103.6 mmol) in 2:1 THF: H$_2$O (125 ml). The resulting reaction mixture was stirred at rt for 18 h. The mixture was then concentrated in vacuo to remove the THF. To the remaining aqueous mixture was added a 10% aqueous potassium hydrogen sulfate solution (150 ml). The resulting mixture was extracted with ethyl acetate. The organic phase was washed with H$_2$O, sat. aqu. NaCl, dried (MgSO$_4$), and concentrated in vacuo. The resulting slightly yellow oil was crystallized from hot ethyl acetate to give 11.8 g (67%) of (2R,4R)-1-(tert-butoxycarbonyl)-4-hydroxypyrrolidine-2-carboxylic acid as a white solid: $^1$H NMR (CD$_3$OD, 300 MHz) δ 1.44 (9H, m), 1.99-2.09 (1H, m), 2.35-2.49 (1H, m), 3.32-3.35 (1H, m), 3.60 (1H, dd, J=6, 12 Hz), 4.25 (1H, dd, J=6, 12 Hz), 4.31-4.36 (1H, m).

Step A (2): (2R,4R)-4-(allyloxy)-1-(tert butoxycarbonyl)pyrrolidine-2-carboxylic acid. To a suspension of NaH (60% in oil, 5.84 g, 146 mmol) in DMF (125 ml) cooled to 0° C. was added a solution of (2R,4R)-1-(tert-butoxycarbonyl)-4-hydroxypyrrolidine-2-carboxylic acid (Step A (1), 13.5 g, 58.4 mmol) in THF (100 ml) dropwise. When the addition was complete, the mixture was allowed to come to rt and stir until gas evolution ceased (30-45 min.). To the reaction mixture was then added allyl bromide (5.05 ml, 58.4 mmol) dropwise. The resulting mixture was stirred at rt for 2 h. The reaction was quenched by the slow addition of 1N HCl (150 ml). pH 4 buffer was added and the mixture was extracted with ethyl acetate. The organic phase was washed with sat. aqu. NaCl, dried (MgSO$_4$), and concentrated in vacuo. Flash chromatography (silica gel, 0-20% methanol/chloroform) gave 13.06 g (83%) of (2R,4R)-4-(allyloxy)-1-(tert-butoxycarbonyl)pyrrolidine-2-carboxylic acid as a clear, colorless oil: $^1$H NMR (CD$_3$OD, 300 MHz) δ 1.44 (9H, m), 2.18-2.44 (2H, m), 3.42 (1H, dd, J=3, 12 Hz), 3.59 (1H, dd, J=6, 12 Hz), 3.95-3.96 (2H, m), 4.10-4.14 (1H, m), 4.26-4.34 (1H, m), 5.12 (1H, d, J=12 Hz), 5.26 (1H, d, J=18 Hz), 5.80-5.92 (1H, m). HPLC retention time: 1.21 min (method A). MS (ESI) (M+H)$^+$ 272.17.

Step A (3): Preparation of (2R,4R)-tert-butyl 4-(allyloxy)-2-(hydroxymethyl)pyrrolidine-1-carboxylate. A solution of (2R,4R)-4-(allyloxy)-1-(tert-butoxycarbonyl)pyrrolidine-2-carboxylic acid (Step A (2), 13.06 g, 48.2 mmol) in THF (250 ml) was cooled to 0° C. Hunig's base (12.6 ml, 72.3 mmol) and ethyl chloroformate (5.51 ml, 57.8 mmol) were added and the mixture was stirred at 0° C. for 15 min. The mixture was then allowed to come to rt and stir for 2 h. during which white ppt. formed. NaBH$_4$ (1.68 g, 44.28 mmol) was then added and the mixture was again cooled to 0° C. To the resulting mixture was added MeOH (179 ml) very slowly. The MeOH addition results in gas evolution and an exotherm. When the addition was complete, the mixture was allowed to come to rt and stir for 2 h. The reaction was then concentrated in vacuo and the residue was partitioned between 1N HCl and ethyl acetate. The organic phase was washed with sat. aqu. NaCl, dried (MgSO$_4$), and concentrated in vacuo. Flash chromatography (silica gel, 0-10% methanol/chloroform) gave 9.58 g (77%) of (2R,4R)-tert-butyl 4-(allyloxy)-2-(hydroxymethyl)pyrrolidine-1-carboxylate as a clear, colorless oil: $^1$H NMR (CD$_3$OD, 300 MHz) δ 1.43 (9H, s), 1.82 (1H, brd s), 2.18 (1H, m), 3.40-3.54 (2H, m), 3.66-3.69 (2H, m), 3.93-4.00 (5H, m), 5.16 (1H, dd, J=3, 9 Hz), 5.24 (1H, dd, J=3, 15 Hz), 5.78-5.91 (1H, m). HPLC retention time: 1.28 min (method A). MS (ESI) (M+H)$^+$ 258.19.

Step A (4): (2R,4R)-tert-butyl 4-(allyloxy)-2-formylpyrrolidine-1-carboxylate. To a solution of (2R,4R)-tert-butyl 4-(allyloxy)-2-(hydroxymethyl)pyrrolidine-1-carboxylate (Step A (3), 9.58 g, 37.28 mmol) in CH$_2$Cl$_2$ (500 ml) was added Dess Martin periodinane (32.0 g, 74.55 mmol). The resulting mixture was stirred at rt for 2 h. and then concentrated in vacuo. Flash chromatography (silica gel, 0-50% ethyl acetate/hexane) gave 7.39 g (78%) of (2R,4R)-tert-butyl 4-(allyloxy)-2-formylpyrrolidine-1-carboxylate as a slightly yellow oil: $^1$H NMR (CD$_3$OD, 300 MHz) δ 1.44 (9H, m), 2.01-2.35 (2H, m), 3.40-3.48 (1H, m), 3.55-3.70 (1H, m), 3.84-3.92 (2H, m), 4.04-4.20 (2H, m), 5.12-5.24 (2H, m), 5.74-5.87 (1H, m), 9.51-9.57 (1H, m). HPLC retention time: 1.39 min (method A). MS (ESI) (M+H+CH$_3$OH)$^+$ 288.21.

Step A (5): 2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate. To a solution of (S)-4-benzyl-3-(3-(3,5-difluorophenyl)propanoyl)oxazolidin-2-one (Preparation B, 1.47 g, 4.27 mmol) in CH$_2$Cl$_2$ (15 ml) at −78° C. was added Bu$_2$BOTf (5.12 ml, 5.12 mmol, 1M in CH$_2$Cl$_2$) and Hunig's base (1.12 ml, 6.41 mmol). The resulting mixture was brought to 0° C. and stirred for 30 min. The mixture was again cooled to −78° C. and a solution of (2R,4R)-tert-butyl 4-(allyloxy)-2-formylpyrrolidine-1-carboxylate (Step A (4), 1.09 g, 4.27 mmol) in CH$_2$Cl$_2$ (10 ml) was added dropwise. When the addition was complete, the mixture was stirred at −78° C. for 5 min., then was allowed to warm to rt. After stirring at rt for 4 h. the mixture was concentrated in vacuo. Flash chromatography (silica gel, 0-75% ethyl acetate/hexane) gave 1.22 g (48%) of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate as a slightly yellow oil: $^1$H NMR (CDCl$_3$, 300 MHz) δ 1.49 (9H, s), 2.03-2.22 (2H, m), 2.31 (1H, d, J=12 Hz), 2.98 (1H, dd, J=3, 15 Hz), 3.07 (1H, t, J=12 Hz), 3.42-3.57 (3H, m), 3.97-4.11 (8H, m), 4.57 (2H, brd s), 5.17-5.30 (2H, m), 5.81-5.94 (1H, m), 6.61 (1H, t, J=9 Hz), 6.90 (2H, brd s), 7.00 (2H, brd s), 7.26 (3H, m). HPLC retention time: 2.04 min (method A). MS (ESI) (M+H)$^+$ 601.37.

Step A (6): (2S,3S)-2-(3,5-difluorobenzyl)-3-((2R,4R)-4-(allyloxy)-1-(tert-butoxycarbonyl)pyrrolidin-2-yl)-3-(tert-butyldimethylsilyloxy)propanoic acid. The compound of Step A (5), (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate, 6.5 grams, 0.011 mmol) was dissolved in 30 mL of DCM and treated with 5.6 mL (32 mmol) of DIEA, followed by 3.43 g (13.0 mmol) of tert-butyldimethylsilyl triflate. After 30 min, the reaction had gone to completion by tlc analysis eluting with 2:3 ethyl acetate:hexanes and was washed twice with a satd. NaHCO$_3$ solution and once with brine. The organic layer was dried and concentrated in vacuo to an oil. The crude product thus obtained was dissolved in 150 mL of THF and chilled to 0° C. A solution of 30% H$_2$O$_2$ in water (9 mL, 0.088 mmol) was then added, followed by a solution of lithium hydroxide (0.53 g, 0.022 mmol) dissolved in 40 mL of water. The reaction solution was allowed to warm to rt and stirred 16 h. The mixture was then diluted with 100 mL of ether and washed twice with a satd. NaHCO$_3$ solution and once with brine. The organic layer was dried and concentrated to an oil which was purified by silica gel chromatography eluting with 2:3 ethyl acetate:hexanes to provide 3.77 g (62%) of the desired title compound as a white foam. $^1$H NMR (400 MHz, CDCl$_3$) δ ppm 0.07 (d, J=23.67 Hz, 6H) 0.93 (s, 9H) 1.35 (s, 9H) 2.06 (m, 1H) 2.22 (m, 1H) 2.46 (m, 1H) 2.78 (t, J=12.59 Hz, 1H) 2.94 (m, 1H) 3.08 (m, 1H) 3.82 (m, 1H) 3.97 (m, 4H) 4.53 (d, J=6.80 Hz, 1H) 5.15 (d, J=10.32 Hz, 1H) 5.25 (dd, J=17.25, 1.13 Hz, 1H) 5.86 (m, J=22.54, 10.70, 5.54 Hz, 1H) 6.59 (t, J=9.06 Hz, 1H) 6.64 (m, 1H) 6.69 (d, J=6.55 Hz, 1H).

Step A (7): (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate. The compound of step A (6) (3.77 g, 6.8 mmol) was dissolved in 20 mL of toluene, and treated with 1.31 g of DIEA (10.2 mmol), followed by 2.24 g (8.2 mmol) of DPPA. The reaction solution was heated to 70° C. for 4 h, then allowed to cool to rt. Excess DIEA (4.4 g, 34 mmol) was then added, followed by 1.83 g (17 mmol) of benzyl alcohol. The reaction solution was again heated to 70° C. for 16 h and then the solvent was directly removed in vacuo. The residue was purified by flash chromatography eluting with a gradient of 2.5% to 10% ethyl acetate in hexanes to provide 2.5 g (56%) of the title compound of preparation A as a white foam. MS (ESI, M+H)$^+$=661.26 $^1$H NMR (500 MHz, CDCl$_3$) δ ppm 0.05 (m, 6H) 0.91 (s, 9H) 1.45 (d, J=24.41 Hz, 9H) 2.14 (s, 1H) 2.41 (m, 1H) 3.14 (d, J=9.77 Hz, 2H) 3.79 (s, 1H) 3.95 (s, 4H) 4.03 (d, J=5.80 Hz, 1H) 4.13 (s, 1H) 4.94 (d, J=12.51 Hz, 1H) 5.00 (m, 1H) 5.15 (d, J=10.68 Hz, 1H) 5.24 (m, 1H) 5.85 (m, 1H) 6.60 (s, 1H) 6.73 (d, J=5.80 Hz, 1H) 7.27 (m, 8H).

Preparation B (S)-4-benzyl-3-(3-(3,5-difluorophenyl)propanoyl)oxazolidin-2-one

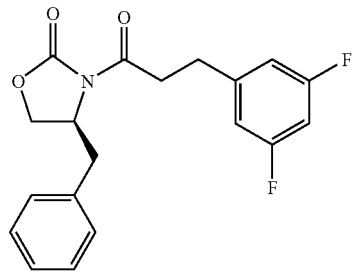

Step B (1): 3,5-difluorophenylhydrocinnamic acid. Commercial 3,5-difluorocinnamic acid (50.0 g, 0.271 mol) was dissolved in a mixture of 800 mL of ethyl acetate and 200 mL of methanol and added to a prewetted bed (methanol) of 5 g of 5% palladium on carbon. The mixture was placed under 40 psi of hydrogen in a Parr apparatus for 30 min, and the hydrogen pressure refilled until it stabilized. After an additional 30 min, the suspension was filtered through a bed of celite and concentrated to a crude oil which solidified upon standing. This material was carried onto the next step without further purification.

Step B (2): 3,5-difluorophenylhydrocinnamoyl chloride. To a solution of 3,5-difluorophenylhydrocinnamic acid (step B (1), 10 g, 54 mmol) in 250 mL of CH$_2$Cl$_2$ was added 2.5 mL of DMF. To this solution was added dropwise oxalyl chloride (6.6 mL, 75 mmol, vigorous gas evolution) and the resulting solution was then stirred at rt for 2 h and then concentrated to a crude oil which was used in the next step without further purification.

Step B (3): (S)-4-benzyl-3-(3-(3,5-difluorophenyl)propanoyl)oxazolidin-2-one. (S)-4-benzyloxazolidin-2-one (10.5 g, 59 mmol) was dissolved in 200 mL of THF and chilled to −78° C. A solution of n-butyllithium in pentane (55.6 mL, 1.18 M, 65 mmol) was then added dropwise. After stirring for an additional 30 min at −78° C., the solution was allowed to come to 0° C. Separately, the acid chloride prepared in step B (2) was dissolved in 100 mL of THF and chilled to −78° C. The oxazolidinone anion solution from above was added dropwise to the acid chloride solution, and upon completion of the addition, the reaction mixture was allowed to warm to rt and stir for 2 h. The reaction solution was then partitioned between water and ethyl acetate and the organic layer was separated and dried with brine and MgSO$_4$ and then concentrated. The crude product was then recrystallized from 95% EtOH to provide white needles. $^1$H NMR (500 MHz, CDCl$_3$) δ ppm 2.77 (dd, J=13.43, 9.46 Hz, 1H) 3.00 (m, 2H) 3.25 (m, 3 H) 4.18 (m, 2H) 4.67 (m, 1H) 6.64 (m, J=9.08, 9.08, 2.29, 2.14 Hz, 1H) 6.79 (dd, J=8.24, 1.83 Hz, 2H) 7.16 (d, J=6.71 Hz, 2H) 7.27 (m, 1H) 7.32 (t, J=7.17 Hz, 2H).

Preparation C (1S,2S)-1-((2R,4R)-4-(allyloxy)-1-benzhydrylpyrrolidin-2-yl)-2-amino-3-(3,5-difluorophenyl)propan-1-ol

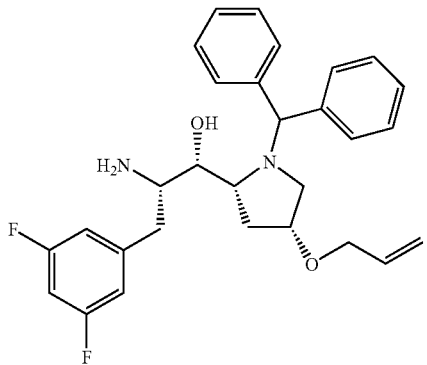

Step C (1): Preparation of (2R,4R)-1-(tert-butoxycarbonyl)-4-hydroxypyrrolidine-2-carboxylic acid. To a suspension of H-D-Cis-Hyp-OH (purchased from Aldrich) (10.0 g, 76.3 mmol) in 2:1 THF:H$_2$O (125 ml) was added a 2.5 molar aqueous sodium hydroxide solution (42.0 ml). To this mixture was added a solution of Di-tert-butyldicarbonate (22.6 g, 103.6 mmol) in 2:1 THF:H$_2$O (125 ml). The resulting reaction mixture was stirred at rt for 18 h. The mixture was then concentrated in vacuo to remove the THF. To the remaining aqueous mixture was added a 10% aqueous potassium hydrogen sulfate solution (150 ml). The resulting mixture was extracted with ethyl acetate. The organic phase was washed with H$_2$O, sat. aqu. NaCl, dried (MgSO$_4$), and concentrated in vacuo. The resulting slightly yellow oil was crystallized from hot ethyl acetate to give 11.8 g (67%) of (2R,4R)-1-(tert-butoxycarbonyl)-4-hydroxypyrrolidine-2-carboxylic acid as a white solid: $^1$H NMR (CD$_3$OD, 300 MHz) δ 1.44 (9H, m), 1.99-2.09 (1H, m), 2.35-2.49 (1H, m), 3.32-3.35 (1H, m), 3.60 (1H, dd, J=6, 12 Hz), 4.25 (1H, dd, J=6, 12 Hz), 4.31-4.36 (1H, m).

Step C (2): Preparation of (2R,4R)-4-(allyloxy)-1-(tert-butoxycarbonyl)pyrrolidine-2-carboxylic acid. To a suspension of NaH (60% in oil) (5.84 g, 146 mmol) in DMF (125 ml) cooled to 0° C. was added a solution of (2R,4R)-1-(tert-butoxycarbonyl)-4-hydroxypyrrolidine-2-carboxylic acid (Step C (1), 13.5 g, 58.4 mmol) in THF (100 ml) dropwise. When the addition was complete, the mixture was allowed to come to rt and stir until gas evolution ceased (30-45 min.). To the reaction mixture was then added allyl bromide (5.05 ml, 58.4 mmol) dropwise. The resulting mixture was stirred at rt for 2 h. The reaction was quenched by the slow addition of 1N HCl (150 ml). pH 4 buffer was added and the mixture was extracted with ethyl acetate. The organic phase was washed with sat. aqu. NaCl, dried (MgSO$_4$), and concentrated in vacuo. Flash chromatography (silica gel, 0-20% methanol/chloroform) gave 13.06 g (83%) of (2R,4R)-4-(allyloxy)-1-(tert-butoxycarbonyl)pyrrolidine-2-carboxylic acid as a clear, colorless oil: $^1$H NMR (CD$_3$OD, 300 MHz) δ 1.44 (9H, m), 2.18-2.44 (2H, m), 3.42 (1H, dd, J=3, 12 Hz), 3.59 (1H, dd, J=6, 12 Hz), 3.95-396 (2H, m), 4.10-4.14 (1H, m), 4.26-4.34 (1H, m), 5.12 (1H, d, J=12 Hz), 5.26 (1H, d, J=18 Hz), 5.80-5.92 (1H, m). HPLC retention time: 1.21 min (method A). MS (ESI) (M+H)$^+$ 272.17.

Step C (3): Preparation of (2R,4R)-tert-butyl 4-(allyloxy)-2-(hydroxymethyl)pyrrolidine-1-carboxylate. A solution of (2R,4R)-4-(allyloxy)-1-(tert-butoxycarbonyl)pyrrolidine-2-carboxylic acid (Step C (2), 13.06 g, 48.2 mmol) in THF (250 ml) was cooled to 0° C. Hunig's base (12.6 ml, 72.3 mmol) and ethyl chloroformate (5.51 ml, 57.8 mmol) were added and the mixture was stirred at 0° C. for 15 min. The mixture was then allowed to come to rt and stir for 2 h. during which white ppt. formed. NaBH$_4$ (1.68 g, 44.28 mmol) was then added and the mixture was again cooled to 0° C. To the resulting mixture was added MeOH (179 ml) very slowly. The MeOH addition results in gas evolution and an exotherm. When the addition was complete, the mixture was allowed to come to rt and stir for 2 h. The reaction was then concentrated in vacuo and the residue was partitioned between 1N HCl and ethyl acetate. The organic phase was washed with sat. aqu. NaCl, dried (MgSO$_4$), and concentrated in vacuo. Flash chromatography (silica gel, 0-10% methanol/chloroform) gave 9.58 g (77%) of (2R,4R)-tert-butyl 4-(allyloxy)-2-(hydroxymethyl)pyrrolidine-1-carboxylate as a clear, colorless oil: $^1$H NMR (CD$_3$OD, 300 MHz) δ 1.43 (9H, s), 1.82 (1H, brd s), 2.18 (1H, m), 3.40-3.54 (2H, m), 3.66-3.69 (2H, m), 3.93-4.00 (5H, m), 5.16 (1H, dd, J=3, 9 Hz), 5.24 (1H, dd, J=3, 15 Hz), 5.78-5.91 (1H, m). HPLC retention time: 1.28 min (method A). MS (ESI) (M+H)$^+$ 258.19.

Step C (4): Preparation of (2R,4R)-tert-butyl 4-(allyloxy)-2-formylpyrrolidine-1-carboxylate. To a solution of (2R,4R)-tert-butyl 4-(allyloxy)-2-(hydroxymethyl)pyrrolidine-1-carboxylate (Step C (3), 9.58 g, 37.28 mmol) in CH$_2$Cl$_2$ (500 ml) was added Dess Martin periodinane (32.0 g, 74.55 mmol). The resulting mixture was stirred at rt for 2 h. and then concentrated in vacuo. Flash chromatography (silica gel, 0-50% ethyl acetate/hexane) gave 7.39 g (78%) of (2R,4R)-tert-butyl 4-(allyloxy)-2-formylpyrrolidine-1-carboxylate as a slightly yellow oil: $^1$H NMR (CD$_3$OD, 300 MHz) δ 1.44 (9H, m), 2.01-2.35 (2H, m), 3.40-3.48 (1H, m), 3.55-3.70 (1H, m), 3.84-3.92 (2H, m), 4.04-4.20 (2H, m), 5.12-5.24 (2H, m), 5.74-5.87 (1H, m), 9.51-9.57 (1H, m). HPLC retention time: 1.39 min (method A). MS (ESI) (M+H+CH$_3$OH)$^+$ 288.21.

Step C (5): Preparation of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate. To a solution of (S)-4-benzyl-3-(3-(3,5-difluorophenyl)propanoyl)oxazolidin-2-one (Preparation M), 1.47 g, 4.27 mmol) in CH$_2$Cl$_2$ (15 ml) at −78° C. was added Bu$_2$BoTf (5.12 ml, 5.12 mmol, 1M in CH$_2$Cl$_2$) and Hunig's base (1.12 ml, 6.41 mmol). The resulting mixture was brought to 0° C. and stirred for 30 min. The mixture was again cooled to −78° C. and a solution of (2R,4R)-tert-butyl 4-(allyloxy)-2-formylpyrrolidine-1-carboxylate (Step C (4), 1.09 g, 4.27 mmol) in CH$_2$Cl$_2$ (10 ml) was added dropwise. When the addition was complete, the mixture was stirred at −78° C. for 5 min., then was allowed to warm to rt. After stirring at rt for 4 h. the mixture was concentrated in vacuo. Flash chromatography (silica gel, 0-75% ethyl acetate/hexane) gave 1.22 g (48%) of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate as a slightly yellow oil: $^1$H NMR (CDCl$_3$, 300 MHz) δ 1.49 (9H, s), 2.03-2.22 (2H, m), 2.31 (1H, d, J=12 Hz), 2.98 (1H, dd, J=3, 15 Hz), 3.07 (1H, t, J=12 Hz), 3.42-3.57 (3H, m), 3.97-4.11 (8H, m), 4.57 (2H, brd s), 5.17-5.30 (2H, m), 5.81-5.94 (1H, m), 6.61 (1H, t, J=9 Hz), 6.90 (2H, brd s), 7.00 (2H, brd s), 7.26 (3H, m). HPLC retention time: 2.04 min (method A). MS (ESI) (M+H)$^+$ 601.37.

Step C (6): Preparation of (2S,3S)-2-(3,5-difluorobenzyl)-3-((2R,4R)-4-(allyloxy)-1-(tert-butoxycarbonyl)pyrrolidin-2-yl)-3-hydroxypropanoic acid. To a solution of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine 1-carboxylate (Step C (5), 1.02 g, 1.7 mmol) in THF (31 ml) was added a solution of LiOH (82 mg, 3.4 mmol) in H$_2$O (7.7 ml), then 30% H$_2$O$_2$ (2.58 ml). This reaction mixture was stirred at rt for 2 h. The mixture was then cooled to 0° C. and a solution of Na$_2$SO$_3$ in H$_2$O was added slowly to quench. The resulting mixture was allowed to come to rt and stir for 10 min. 1N HCl was added and the mixture was extracted with diethyl ether. The organic phase was washed with sat. aqu. NaCl, dried (MgSO$_4$), and concentrated in vacuo. Flash chromatography (silica gel, 50% MTBE/diethyl ether) gave 408 mg (54%) of (2S,3S)-2-(3,5-difluorobenzyl)-3-((2R,4R)-4-(allyloxy)-1-(tert-butoxycarbonyl)pyrrolidin-2-yl)-3-hydroxypropanoic acid as a clear, colorless oil: $^1$H NMR (CDCl$_3$, 300 MHz) δ 1.42 (9H, s), 1.46-1.51 (1H, m), 2.01-2.18 (2H, m), 2.56 (1H, t, J=9 Hz), 2.91 (1H, dd, J=9, 15 Hz), 3.20-3.30 (1H, m), 3.45-3.51 (2H, m), 3.96-4.24 (6H, m), 5.21-5.31 (2H, m), 5.81-5.94 (1H, m), 6.60 (1H, t, J=6 Hz), 6.74 (2H, t, J=6 Hz). HPLC retention time: 1.63 min (method A). MS (ESI) (M+H)$^+$ 442.25.

Step C (7): Preparation of (2R,4R)-tert-butyl 2-((4S,5S)-4-(3,5-difluorobenzyl)-2-oxooxazolidin-5-yl)-4-(allyloxy)pyrrolidine-1-carboxylate. To a solution of (2S,3 S)-2-(3,5-difluorobenzyl)-3-((2R,4R)-4-(allyloxy)-1-(tert-butoxycarbonyl)pyrrolidin-2-yl)-3-hydroxypropanoic acid (Step C (6), 400 mg, 0.907 mmol) in toluene (22 ml) was added diphenylphosphoryl azide (353 µl, 1.63 mmol) and triethyl amine (253 µl, 1.81 mmol). This reaction mixture was brought to 65° C. and stirred for 18 h. The mixture was then concentrated in vacuo. The residue was taken up in ethyl acetate. This solution was washed with sat. aqu. sodium bicarbonate, H$_2$O, sat. aqu. NaCl, dried (MgSO$_4$), and concentrated in vacuo. Flash chromatography (silica gel, 0-60% ethyl acetate/hexane) gave 278 mg (70%) of (2R,4R)-tert-butyl 2-((4S,5S)-4-(3,5-difluorobenzyl)-2-oxooxazolidin-5-yl)-4-(allyloxy)pyrrolidine-1-carboxylate as a yellow oil: $^1$H NMR (CDCl$_3$, 300 MHz) δ 1.46 (9H, s), 2.03-2.14 (1H, m), 2.43-2.53 (2H, m), 3.35 (1H, d, J=12 Hz), 3.70 (2H, brd s), 3.90-3.96 (2H, m), 4.06-4.11 (2H, m), 4.25 (1H, dt, J=3, 9 Hz), 4.78 (1H, s), 4.88 (1H, t, J=6 Hz), 5.18 (1H, dd, J=3, 9 Hz), 5.28 (1H, dd, J=3, 18 Hz), 5.83-5.96 (1H, m), 6.68-6.76 (3H, m). HPLC retention time: 1.68 min (method A). MS (ESI) (M+H)$^+$ 439.27.

Step C (8): Preparation of (4S,5R)-4-(3,5-difluorobenzyl)-5-((2R,4R)-4-(allyloxy)pyrrolidin-2-yl)oxazolidin-2-one. A solution of (2R,4R)-tert-butyl 2-((4S,5 S)-4-(3,5-difluorobenzyl)-2-oxooxazolidin-5-yl)-4-(allyloxy)pyrrolidine-1-carboxylate (Step C (7), 278 mg, 0.635 mmol) in CH$_2$Cl$_2$ (2 ml) was treated with TFA (1 ml). This reaction mixture was stirred at rt for 1 h. The mixture was then concentrated in vacuo. CH$_2$Cl$_2$ was added to the residue and the mixture was again concentrated in vacuo. The residue was partitioned between ethyl acetate and sat. aqu. sodium bicarbonate. The organic phase was washed with sat. aqu. NaCl, dried (MgSO$_4$), and concentrated in vacuo to give 185 mg (86%) of (4S,4R)-4-(3,5-difluorobenzyl)-5-((2R,4R)-4-(allyloxy)pyrrolidin-2-yl)oxazolidin-2-one as an opaque yellow oil: $^1$H NMR (CDCl$_3$, 300 MHz) δ 2.05-2.23 (2H, m), 2.34 (1H, brd s), 2.61 (1H, t, J=12 Hz), 3.00-3.11 (2H, m), 3.16 (1H, dd, J=3, 12 Hz), 3.48-3.55 (1H, m), 3.90-4.13 (4H, m), 4.60 (1H, dd, J=9, 12 Hz), 4.92 (1H, s), 5.17 (1H, dd, J=3, 9 Hz), 5.26 (1H, dd, J=3, 15 Hz), 5.82-5.95 (1H, m), 6.68-6.74 (3H, m). HPLC retention time: 0.84 min (method A). MS (ESI) (M+H)$^+$ 339.20.

Step C (9): (4S,5S)-4-(3,5-difluorobenzyl)-5-((2R,4R)-4-(allyloxy)-1-benzhydrylpyrrolidin-2-yl)oxazolidin-2-one. A mixture of (4S,5R)-4-(3,5-difluorobenzyl)-5-((2R,4R)-4-(allyloxy)pyrrolidin-2-yl)oxazolidin-2-one (Step C (8), 2.03 g, 6.0 mmol), benzylhydryl bromide (2.22 g, 9.0 mmol), and potassium carbonate (1.24 g, 9.0 mmol) in acetonitrile (40 mL) was stirred at reflux for 35 min. After cooling to rt, the mixture was filtered and concentrated in vacuo. The crude mixture was purified by Flash Chromatography (silica gel, 0-7.5% methanol/chloroform) to give a slightly yellow oil as the title compound (2.64 g, 87% yield): $^1$H NMR (CDCl$_3$, 300 MHz) δ 1.95-2.23 (2H, m), 2.36 (1H, t, J=12 Hz), 2.70 (1H, m), 3.02 (2H, d, J=6 Hz), 3.48 (1H, m), 3.71-3.99 (4H, m), 4.70 (1H, s), 4.78 (1H, t, J=6 Hz), 4.93 (1H, s), 5.12 (1H, m), 5.22 (1H, dd, J=3, 18 Hz), 5.84 (1H, m), 6.49 (1H, d, J=6 Hz), 6.67 (1H, m), 7.20-7.39 (11H, m).

Step C (10): (1S,2S)-1-((2R,4R)-4-(allyloxy)-1-benzhydrylpyrrolidin-2-yl)-2-amino-3-(3,5-difluorophenyl)propan-1-ol. To a solution of (4S,5S)-4-(3,5-difluorobenzyl)-5-((2R,4R)-4-(allyloxy)-1-benzhydrylpyrrolidin-2-yl)oxazolidin-2-one (Step C (9), 60 mg) in EtOH (5 mL) was added a solution of LiOH (29 mg) in H$_2$O (1 mL). This reaction mixture was stirred at 90° C. overnight. EtOH was removed and ethyl ether (50 mL) was added to the mixture and washed with 1N HCl (40 mL) twice. The aqueous layer was neutralized with 50% NaOH to pH=12 and extracted with ethyl acetate (100 mL). The organic layer was dried (Na$_2$SO$_4$), and concentrated in vacuo to give the title compound: $^1$H NMR (CDCl$_3$, 300 MHz) δ 1.89-2.06 (2H, m), 2.29-2.49 (2H, m), 2.66 (1H, dt, J=3, 9 Hz), 2.90 (1H, dd, J=3, 9 Hz), 2.98 (1H, dd, J=3, 12 Hz), 3.19 (1H, d, J=12 Hz), 3.36 (1H, m), 3.88 (1H, m), 3.98 (2H, m), 4.86 (1H, s), 5.18 (1H, m), 5.28 (1H, m), 5.86-5.99 (1H, m), 6.58-6.71 (3H, m), 7.09-7.36 (10H, m). MS (ESI) (M+H)$^+$ 479.24.

Preparation D (4S,5S)-4-(3,5-difluorobenzyl)-5-((2R,4S)-1-benzhydryl-4-hydroxypyrrolidin-2-yl)oxazolidin-2-one

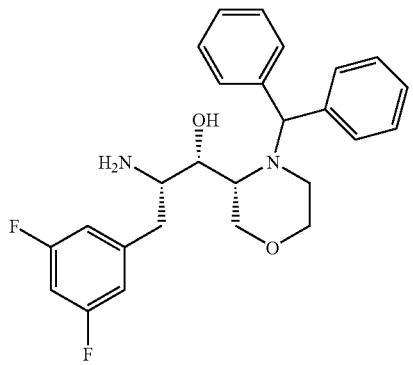

Step D (1): tert-Butyl 3-(hydroxymethyl)morpholine-4-carboxylate. To a solution of 4-(tert-butoxycarbonyl)morpholine-3-carboxylic acid (4.7 g, 20.35 mmol) in THF (120 mL) were added Hunig's base (6.6 g, 50.875 mmol). Then chloroethylformate (2.65 g, 24.4 mmol) was added at 0° C. After stirring from 0° C. to rt over 1.5 h, NaBH$_4$ (3.1 g, 81.4 mmol) was added and after 15 min, MeOH (20 mL) was added slowly at 0° C. After stirring at rt for 1 h, THF and MeOH was removed and ethyl acetate (600 mL) was added and the mixture was washed with NaHCO$_3$, H$_2$O, and dried (Na$_2$SO$_4$), and concentrated in vacuo to give 3.56 g of the title compound (81% yield): $^1$H NMR (CDCl$_3$, 500 MHz) δ 1.46 (9H, s), 2.03 (1H, brd s), 3.17 (1H, m), 3.46 (1H, m), 3.56 (1H, m), 3.72-3.86 (4H, m), 3.91 (1H, d, J=10 Hz), 3.99 (1H, brd s).

Step D (2): tert-Butyl 3-formylmorpholine-4-carboxylate. To a solution of dimethyl sulfoxide (32.4 g, 41.5 mmol) in dichloromethane (100 mL) was added oxalyl dichloride (3.14 g, 24.7 mmol) at −78° C. After stirring at −78° C. for 15 min, the mixture was added a solution of tert-butyl 3-(hydroxymethyl) morpholine-4-carboxylate (step D (1), 3.58 g, 16.5 mmol) in dichloromethane (100 mL) and stirred at −78° C. for 1 h. Then Hunig base (8.5 g, 66 mmol) was added and the reaction mixture was warmed up to rt over 3 h. The solvent was removed and ethyl acetate (500 mL) was added. The mixture was washed with sodium carbonate solution, H$_2$O, and dried (Na$_2$SO$_4$), and concentrated in vacuo to give 3.4 g of the title compound.

Step D (3): tert-Butyl 3-((1S,2S)-2-(3,5-difluorobenzyl)-3-((S)-4-benzyl-2-oxooxazolidin-3-yl)-1-hydroxy-3-oxopropyl)morpholine-4-carboxylate. To a solution of (S)-4-benzyl-3-(3-(3,5-difluorophenyl)propanoyl)oxazolidin-2-one (preparation M, 6.0 g, 17.4 mmol) in CH$_2$Cl$_2$ (200 mL) at −78° C. was added Bu$_2$BOTf (20.5 ml, 20.5 mmol, 1M in CH$_2$Cl$_2$) and Hunig's base (5.1 g, 39.5 mmol). The resulting mixture was brought up to 0° C. over 15 min. and cooled back to −78° C. A solution of tert-butyl 3-formylmorpholine-4-carboxylate (step D (2), 3.4 g, 15.8 mmol) in CH$_2$Cl$_2$ (200 mL) was added. When the addition was complete, the mixture was allowed to warm to and stirred at rt overnight. Dichloromethane (500 mL) was added and the mixture was washed with H$_2$O, dried and concentrated in vacuo. The crude mixture was purified by silica gel Flash Chromatography (0% to 30% to 50% to 70% EtOAc/Hexane step gradient) to give 5.6 g of the title compound (63% yield): MS (ESI) (M+Na)$^+$ 583.21.

Step D (4): (2S,3S)-2-(3,5-Difluorobenzyl)-3-(4-(tert-butoxycarbonyl)morpholin-3-yl)-3-hydroxypropanoic acid. To a solution of tert-butyl 3-((1S,2S)-2-(3,5-difluorobenzyl)-3-((S)-4-benzyl-2-oxooxazolidin-3-yl)-1-hydroxy-3-oxopropyl)morpholine-4-carboxylate (step D (3), 2.8 g, 5 mmol) in THF (60 mL) was added a solution of LiOH (240 mg, 10 mmol) in H$_2$O (10 mL), then 30% H$_2$O$_2$ (5.7 g, 50 mmol) was added at 0° C. This reaction mixture was warmed up to rt and stirred at rt overnight. THF was removed and ethyl ether (200 mL) was added. The mixture was washed with 1N NaOH (150 mL) twice. The aqueous layer was treated with conc. HCl to pH=1 and extracted with ethyl acetate (300 mL) twice. The organic layers were dried (Na$_2$SO$_4$), and concentrated in vacuo to give 1.6 g of the title compound (80% yield) which was used in the next step without purification. MS (ESI) (M+Na)$^+$ 424.13.

Step D (5): tert-Butyl 3-((4S,5S)-4-(3,5-difluorobenzyl)-2-oxooxazolidin-5-yl)morpholine-4-carboxylate. To a solution of (2S,3S)-2-(3,5-difluorobenzyl)-3-(4-(tert-butoxycarbonyl)morpholin-3-yl)-3-hydroxypropanoic acid (step D (4)), 1.6 g, 4. mmol) in toluene (100 mL) was added diphenylphosphoryl azide (1.65 g, 6 mmol) and triethyl amine (1.01 g, 10 mmol). This reaction mixture was stirred at 80° C. for 4 h. Ethyl acetate (500 mL) was added. The mixture was washed with sodium carbonate solution, H$_2$O, dried over Na$_2$SO$_4$ and concentrated. The crude mixture was purified by silica gel Flash Chromatography (0% to 20% to 30% to 50% to 70% EtOAc/Hexane step gradient) to give 800 mg of the title compound: MS (ESI) (M−H)$^−$ 397.12.

Step D (6): (4S,5S)-4-(3,5-Difluorobenzyl)-5-(morpholin-3-yl)oxazolidin-2-one. A solution of tert-butyl 3-((4S,5S)-4-(3,5-difluorobenzyl)-2-oxooxazolidin-5-yl)morpholine-4-carboxylate (step D (5), 230 mg) in CH$_2$Cl$_2$ (4 mL) was treated with TFA (3 mL). This reaction mixture was stirred at rt for 1.5 h. The mixture was then concentrated in vacuo. Diethyl ether (50 mL) was added and the mixture was washed with 1N HCl solution (40 mL) twice. Aqueous layer was neutralized with 50% aqueous NaOH to pH=12. The mixture was extracted with ethyl acetate (80 mL) twice. The combined organic layers were dried (Na$_2$SO$_4$), and concentrated in vacuo to give 180 mg of the title compound: MS (ESI) (M+H)$^+$ 299.17.

Step D (7): (4S,5S)-4-(3,5-Difluorobenzyl)-5-((R)-4-benzhydrylmorpholin-3-yl)oxazolidin-2-one. To a solution of (4S,5S)-4-(3,5-difluorobenzyl)-5-(morpholin-3-yl)oxazolidin-2-one (step D (6), 180 mg, 0.6 mmol) in acetonitrile (5 mL) were added potassium carbonate (248 mg, 1.8 mmol) and bromodiphenylmethane (296 mg, 1.2 mmol). This mixture was stirred at 100° C. for 1.5 h. Solvent was removed and the crude mixture was purified by silica gel Flash Chromatography (0% to 20% to 40% to 65% EtOAc/Hexane step gradient) to give 85 mg of the title compound (29% yield): $^1$H NMR (CDCl$_3$, 500 MHz) δ 2.14 (1H, m), 2.76 (2H, d, J=15 Hz), 2.98 (1H, d, J=5 Hz), 3.15 (1H, m), 3.52 (1H, m), 3.67 (1H, m), 3.87-3.94 (3H, m), 5.23 (2H, d, J=10 Hz), 5.31 (1H, m), 6.56 (2H, d, J=5 Hz), 6.70 (1H, m), 7.16 (1H, d, J=5 Hz), 7.21-7.37 (7H, m), 7.41 (2H, d, J=10 Hz). MS (ESI) (M+H)$^+$ 465.14.

Step D (8): (1S,2S)-2-Amino-1-((R)-4-benzhydrylmorpholin-3-yl)-3-(3,5-difluorophenyl)propan-1-ol. To a solution of (4S,5S)-4-(3,5-difluorobenzyl)-5-((R)-4-benzhydrylmorpholin-3-yl)oxazolidin-2-one (step D (7), 85 mg, 0.18 mmol) in EtOH (2 mL) was added a solution of LiOH (66 mg, 2.75 mmol) in H$_2$O (1 mL). This reaction mixture was brought to 98° C. and stirred for overnight. Solvent was removed and 1N HCl solution (50 mL) was added to the mixture and washed with diethyl ether. The aqueous phase was basified with 50% aqueous NaOH solution. This mixture was extracted with ethyl acetate. The combined organic layer was dried (Na$_2$SO$_4$), and concentrated in vacuo to give 80 mg of the title compound: $^1$H NMR (CDCl$_3$, 500 MHz) δ 1.94-2.06 (3H, m), 2.30 (1H, dd, J=10, 15 Hz), 2.51-2.59 (1H, m), 2.73-2.81 (1H, m), 2.90 (1H, m), 2.95 (1H, m), 3.08 (1H, m), 3.70 (1H, m), 3.80 (1H, dt, J=5, 10 Hz), 3.91 (1H, m), 4.09 (1H, m), 4.14 (1H, m), 5.05 (1H, s), 6.60-6.68 (3H, m), 7.15-7.31 (6H, m), 7.37 (2H, d, J=10 Hz), 7.42 (2H, d, J=5 Hz). MS (ESI) (M+H)$^+$ 439.20.

Preparation E 3-(dipropylcarbamoyl)benzoic acid

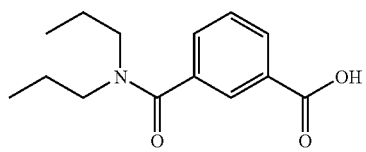

Step E (1): Methyl 3-(dipropylcarbamoyl)benzoate. To a solution of 3-(methoxycarbonyl)benzoic acid (6.7 g, 37.2 mmol) in DMF (60 mL) was added HATU (17.0 g, 44.7 mmol) and dipropylamine (9.4 g, 93 mmol) and the reaction mixture was stirred at rt overnight. Ethyl acetate (600 mL) was added and the mixture was washed with $H_2O$, dried and concentrated to give the title compound was used in the next step without purification.

Step E (2): To a solution of methyl 3-(dipropylcarbamoyl) benzoate (Step E (1), 7.7 mmol) in THF (100 mL) was added LiOH (1.7 g, 74.4 mmol) in $H_2O$ (20 mL) and the mixture was stirred at rt for 3 h. The solvent was removed and 1N NaOH (100 mL) was added. The mixture was washed with ethyl acetate, neutralized with conc. HCl to pH=2, and extracted with ethyl acetate. The organic layer was dried over $Na_2SO_4$ and concentrated to give the title compound: $^1$H NMR ($CDCl_3$, 500 MHz) δ 0.74 (3H, brd s), 0.98 (3H, brd s), 1.54 (2H, brd s), 1.70 (2H, brd s), 3.15 (2H, brd s), 3.48 (2H, brd s), 7.50 (1H, m), 7.61 (1H, m), 8.08 (1H, m), 8.11 (1H, m), 8.30 (1H, brd s).

Preparation F 3-(butyl(methyl)carbamoyl)benzoic acid

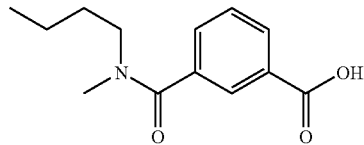

Step F (1): Methyl 3-(butyl(methyl)carbamoyl)benzoate. To a solution of 3-(methoxycarbonyl)benzoic acid (1.8 g, 10 mmol) in dichloromethane (40 mL) and DMF (20 mL) was added Hunig's base (2.58 g, 20 mmol) to make a clear solution and HATU (4.18 g, 11 mmol) was then added. After stirring for 10 min, the reaction mixture was added methylbutylamine (1.13 g, 13 mmol) and the reaction mixture was stirred at rt for 3 h. Dichloromethane was removed and ethyl acetate (300 mL) was added and the mixture was washed with 1N HCl, sodium carbonate solution, $H_2O$, dried and concentrated to give the title compound ready for next step without purification: $^1$H NMR ($CDCl_3$, 500 MHz) δ 0.79-0.98 (3H, m), 1.15 (1H, m), 1.41 (1H, brd s), 1.52 (1H, brd s), 1.64 (1H, m), 2.92-3.07 (2H, m), 3.21 (1H, brd s), 3.53 (1H, brd s), 3.91 (3H, s), 7.47 (1H, m), 7.58 (1H, d, J=10 Hz), 8.05-8.07 (2H, m).

Step F (2): 3-(Butyl(methyl)carbamoyl)benzoic acid. The solution of methyl 3-(butyl(methyl)carbamoyl)benzoate (Step F (1), 1.8 g, 7.7 mmol) in THF (50 mL) was added LiOH (370 mg, 15.4 mmol) in $H_2O$ (10 mL) and the mixture was stirred at rt overnight. The solvent was removed and 1N NaOH (150 mL) was added. The mixture was washed with ethyl acetate, neutralized with conc. HCl to pH=2, extracted with ethyl acetate. The organic layer was dried over $Na_2SO_4$ and concentrated to give 1.8 g of the title compound: $^1$H NMR ($CDCl_3$, 500 MHz) δ 1.16 (1H, m), 1.42 (1H, m), 1.54 (1H, m), 1.65 (1H, m), 2.10 (3H, m), 2.94-3.09 (3H, m), 3.22 (1H, m), 3.55 (1H, m), 7.51 (1H, m), 7.64 (1H, m), 8.10-8.13 (2H, m). MS (ESI) (M+H)$^+$ 236.17.

Preparation G 3-(dipropylcarbamoyl)benzoic acid

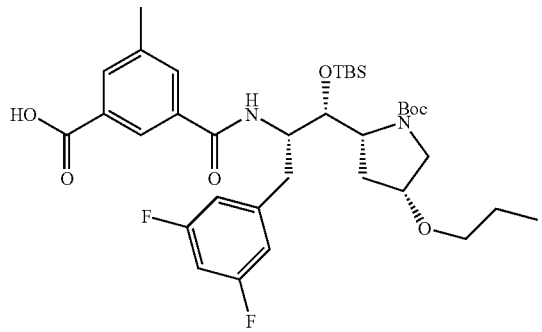

Step G (1): 3-amino-5-(methoxycarbonyl)benzoic acid. A suspension of 3-(methoxycarbonyl)-5-nitrobenzoic acid (20.0 g) and palladium on carbon (5 wt %, 4.0 g) in MeOH (600 mL) was shaken in hydrogenator under hydrogen at 50 psi for 3 h. The mixture was filtered and concentrated in vacuo to give the title compound: $^1$H NMR ($CD_3OD$, 500 MHz) δ ppm 3.90 (3H, s), 7.52 (1H, m), 7.55 (1H, m), 7.92 (1H, m). MS (ESI) (M–H)$^-$ 194.08.

Step G (2): 3-bromo-5-(methoxycarbonyl)benzoic acid. To a mixture of copper (II) bromide (5.5 g, 24.6 mmol), n-butyl nitrite (3.17 g, 30.75 mmol) and acetonitrile (300 mL) was added 3-amino-5-(methoxycarbonyl)benzoic acid (Step G (1), 4.0 g, 20.5 mmol) in aceonitrile (300 mL) over 30 min at 0° C. and the mixture was warmed up and stirred at rt for 3 h. $H_2O$ was added and acetonitrile was removed. Ethyl acetate (600 mL) was added and the mixture was washed with 3N HCl, $H_2O$, dried over $Na_2SO_4$, and concentrated in vacuo to give the title compound (97% yield): $^1$H NMR ($CDCl_3$, 500 MHz) δ ppm 3.96 (3H, s), 8.41 (1H, s), 8.41 (1H, s), 8.67 (1H, m). MS (ESI) (M–H)$^-$ 259.02.

Step G (3): Preparation of (2R,4R)-tert-butyl 2-((1S,2S)-2-(3-bromo-5-(methoxycarbonyl)benzamido)-1-(tert-butyldimethylsilyloxy)-3-(3,5-difluorophenyl)propyl)-4-propoxypyrrolidine-1-carboxylate. To a solution of 3-bromo-5-(methoxycarbonyl)benzoic acid (Step G (2), 111 mg, 0.43 mmol) in dichloromethane (10 mL) and was added Hunig's base (108 mg, 0.84 mmol) to make a clear solution and HATU (167 mg, 0.44 mmol) was then added. After stirring for 20 min, the reaction mixture was added (2R,4R)-tert-butyl 2-((1S,2S)-2-amino-1-(tert-butyldimethylsilyloxy)-3-(3,5-difluorophenyl)propyl)-4-propoxypyrrolidine-1-carboxylate (Example 1, Step 1 (A), 150 mg, 0.28 mmol) and the reaction mixture was stirred at rt overnight. The crude mixture was purified by silica gel flash Chromatography (0% to 10% to 20% EtOAc/Hexane step gradient) to give 170 mg of the title compound (79% yield): $^1$H NMR ($CDCl_3$, 500 MHz) δ ppm 0.03 (3H, s), 0.06 (3H, s), 0.83 (9H, s), 0.88 (3H, m), 1.45-1.54 (11H, m), 1.96-2.02 (1H, m), 2.20 (1H, d, J=10 Hz), 2.67 (1H, dd, J=5, 15 Hz), 2.84 (1H, m), 3.27-3.38 (3H, m), 3.76 (1H, dd, J=5, 10 Hz), 3.91 (3H, s), 4.00 (1H, m), 4.05-4.11 (2H, m), 4.63 (1H, m), 6.61 (1H, m), 6.76 (2H, d, J=5 Hz), 8.25 (1H, m), 8.32 (1H, s), 8.53 (1H, s), 8.74 (1H, d, J=5 Hz). MS (ESI) (M+H)$^+$ 771.32.

Step G (4): Preparation of (2R,4R)-tert-butyl 2-((1S,2S)-1-(tert-butyldimethylsilyloxy)-3-(3,5-difluorophenyl)-2-(3-(methoxycarbonyl)-5-methylbenzamido)propyl)-4-propoxypyrrolidine-1-carboxylate. To a solution of (2R,4R)-tert-butyl 2-((1S,2S)-2-(3-bromo-5-(methoxycarbonyl)benzamido)-1-(tert-butyldimethylsilyloxy)-3-(3,5-difluorophenyl)propyl)-4-propoxypyrrolidine-1-carboxylate (Step G (3). 163 mg, 0.21 mmol) in DMF (10 mL) were added potassium carbonate (87 mg, 0.63 mmol), Pd(PPh$_3$)$_4$ (24 mg, 0.021 mmol), and trimethylboroxine (53 mg, 0.42 mmol) and the reaction mixture was stirred at 100° C. with sealed cap for 5 h. Then another portion of trimethylboroxine (53 mg, 0.42 mmol) was added and the reaction was stirred at 60° C. overnight. Another portion of trimethylboroxine (53 mg, 0.42 mmol) was added and the reaction was stirred at 100° C. for 6 h. Ethyl acetate (100 mL) was added and the mixture was washed with H$_2$O and concentrated under vacuum. The crude mixture was purified by silica gel Flash Chromatography (0% to 5% to 10% to 15% EtOAc/Hexane step gradient) to give 110 mg of the title compound (77% yield): $^1$H NMR (CDCl$_3$, 500 MHz) δ ppm 0.02 (3H, s), 0.07 (3H, s), 0.85 (9H, s), 0.88 (3H, m), 1.45-1.52 (11H, m), 2.02-2.07 (1H, m), 2.20 (1H, d, J=15 Hz), 2.41 (3H, s), 2.66 (1H, dd, J=10, 15 Hz), 2.94 (1H, m), 3.28-3.37 (3H, m), 3.76 (1H, dd, J=5, 10 Hz), 3.90 (3H, s), 3.99 (1H, m), 4.07-4.13 (2H, m), 4.62 (1H, m), 6.59 (1H, m), 6.77 (1H, s), 6.79 (1H, s), 7.91 (1H, s), 7.94 (1H, s), 8.20 (1H, brd s), 8.34 (1H, s). MS (ESI) (M+H)$^+$ 705.41.

Step G (5): Preparation of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)-5-methylbenzoic acid. To a solution of (2R,4R)-tert-butyl 2-((1S,2S)-1-(tert-butyldimethylsilyloxy)-3-(3,5-difluorophenyl)-2-(3-(methoxycarbonyl)-5-methylbenzamido)propyl)-4-propoxypyrrolidine-1-carboxylate (Step G (4), 110 mg, 0.16 mmol) in THF (2 mL) was added a solution of LiOH (18 mg, 0.8 mmol) in H$_2$O (0.4 mL). This reaction mixture was stirred at rt for 2 h. MeOH (2 mL) was added to the reaction mixture and stirred for another 2 h at rt. Ethyl ether (100 mL) was added to the mixture and washed with 1N HCl, H$_2$O, dried (Na$_2$SO$_4$), and concentrated in vacuo to give 105 mg of the title compound: $^1$H NMR (CDCl$_3$, 500 MHz) δ ppm 0.05 (3H, s), 0.10 (3H, s), 0.93 (3H, m), 0.97 (9H, s), 1.47 (9H, s), 1.58 (2H, m), 2.26 (1H, m), 2.39 (3H, s), 2.47-2.52 (1H, m), 2.61 (1H, m), 3.07 (1H, m), 3.27 (1H, m), 3.37 (1H, dt, J=5, 10 Hz), 3.47 (1H, dt, J=5, 10 Hz), 3.86 (1H, dd, J=5, 10 Hz), 3.97 (1H, m), 4.12 (1H, m), 4.36 (1H, m), 4.50 (1H, m), 6.47 (1H, m), 6.89 (1H, s), 6.90 (1H, s), 7.90 (1H, s), 7.95 (1H, s), 8.26 (1H, d, J=10 Hz), 8.54 (1H, s). MS (ESI) (M−H)$^-$ 689.49.

Preparation H 3-((R)-2-(methoxymethyl)pyrrolidine-1-carbonyl)-5-(oxazol-2-yl)benzoic acid

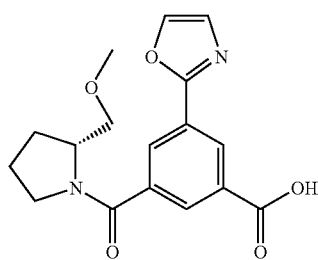

Step H (1): (R)-methyl 3-bromo-5-(2-(methoxymethyl)pyrrolidine-1-carbonyl)benzoate. To a solution of 3-bromo-5-(methoxycarbonyl)benzoic acid (1.8 g, 6.95 mmol) in dichloromethane (100 mL) and was added Hunig's base (2.7 g, 20.85 mmol) to make a clear solution and HATU (3.17 g, 8.34 mmol) was then added. After stirring for 30 min, the reaction mixture was added (R)-2-(methoxymethyl)pyrrolidine (800 mg, 6.95 mmol) and the reaction mixture was stirred at rt for 6 h. Dichloromethane (100 mL) was added and the mixture was washed with 1N NaOH, H$_2$O and concentrated under vacuum. The crude mixture was purified by silica gel Flash Chromatography (0% to 20% to 40% EtOAc/Hexane step gradient) to give 1.8 g of the title compound (73% yield): $^1$H NMR (CDCl$_3$, 500 MHz) δ ppm 1.77-2.08 (4H, m), 3.14-3.47 (5H, m), 3.63 (2H, brd s), 3.82 (3H, s), 4.41 (1H, brd s), 7.83 (1H, s), 8.07 (1H, s), 8.20 (1H, m).

Step H (2): Preparation of methyl 3-((R)-2-(methoxymethyl)pyrrolidine-1-carbonyl)-5-(oxazol-2-yl)benzoate. To a solution of oxazole (2.0 g, 29.0 mmol) in THF (30 mL) was added n-butyl lithium (2.0 M solution in cyclohexanes, 16 mL, 31.9 mmol) at −78° C. slowly. The reaction mixture was stirred at −78° C. for 1.2 h, then tributylstannyl chloride (5.0 g, 15.4 mmol) was added. The reaction mixture was warmed up to rt over 3 h. Hexanes (200 mL) was added and the mixture was washed with H$_2$O, dried over Na$_2$SO$_4$ and concentrated under vacuum to give 5.6 g of the 2-(tributylstannyl) oxazole ready for use.

To a solution of (R)-methyl 3-bromo-5-(2-(methoxymethyl)pyrrolidine-1-carbonyl)benzoate (Step H (1), 350 mg, 1.0 mmol) in dioxane (5 mL) were added Pd(PPh$_3$)$_4$ (173.5 mg, 0.15 mmol) and 2-(tributylstannyl)oxazole (1.8 g, 5.0 mmol) above made and the reaction mixture was stirred at 95° C. with sealed cap for 16 h. Ethyl acetate (200 mL) was added and the mixture was washed with H$_2$O and concentrated under vacuum. The crude mixture was purified by silica gel Flash Chromatography (0% to 30% to 50% to 70% EtOAc/Hexane step gradient) to give 250 mg of the title compound: $^1$H NMR (CDCl$_3$, 500 MHz) δ ppm 1.75-2.11 (4H, m), 3.08 (1H, brd s), 3.38 (3H, s), 3.50 (1H, m), 3.63 (2H, s), 3.83 (3H, s), 4.43 (1H, s), 7.24 (1H, s), 7.73 (1H, s), 8.22 (1H, s), 8.35 (1H, s), 8.71 (1H, s). MS (ESI) (M+H)$^+$ 345.26.

Step H (3): Preparation of 3-((R)-2-(methoxymethyl)pyrrolidine-1-carbonyl)-5-(oxazol-2-yl)benzoic acid. To a solution of methyl 3-((R)-2-(methoxymethyl)pyrrolidine-1-carbonyl)-5-(oxazol-2-yl)benzoate (Step H (2), (250 mg) in THF (5 mL) was added a solution of LiOH (60 mg) in H$_2$O (1 mL). MeOH (1 mL) to make a homogeneous solution. This reaction mixture was stirred at rt for 1 h. Ethyl ether (150 mL) was added to the mixture and washed with 1N NaOH and the aqueous layer was neutralized with conc. HCl to pH ~1. The mixture was extracted with diethyl ether and the organic layer was dried (Na$_2$SO$_4$), and concentrated in vacuo to give 90 mg of the title compound (28% yield over 2 steps): $^1$H NMR (CDCl$_3$, 500 MHz) δ ppm 1.75-2.06 (4H, m), 3.08 (1H, m), 3.24-4.06 (6H, m), 4.46 (1H, m), 7.30 (1H, s), 7.75 (1H, s), 8.30 (1H, s), 8.37 (1H, s), 8.82 (1H, s), 8.98 (1H, brd s). MS (ESI) (M+H)$^+$ 331.22.

Preparation I (2R,4R)-tert-butyl 2-((1S,2S)-1-(tert-butyldimethyl-silyloxy)-3-(3,5-difluorophenyl)-2-(3-hydroxy-5-(2-oxopyrrolidin-1-yl)benzamido)propyl)-4-propoxy-pyrrolidine-1-carboxylate

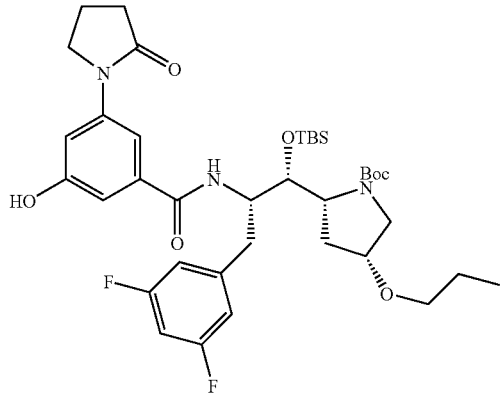

Step I (1): 3-Bromo-5-nitrobenzoic acid. To a solution of 3-amino-5-nitrobenzoic acid (4.0 g, 21.98 mmol) in HBr (48% in $H_2O$, 40 mL) was added $NaNO_2$ (2.0 g, 28.98 mmol) in portions over 25 min. Then CuBr (2.0 g) in HBr (48% in $H_2O$, 10 mL) was added to the above mixture slowly. The mixture was stirred at 65° C. for 2 h. $H_2O$ (300 mL) was added and the mixture was extracted with diethyl ether (300 mL) twice. The combined organic layers were washed with $H_2O$, dried over sodium sulfate, filtered and concentrated in vacuo to give 5.3 g of the title compound: $^1H$ NMR ($CD_3OD$, 500 MHz) δ ppm 8.50 (1H, m), 8.62 (1H, m), 8.74 (1H, m).

Step I (2): 3-Nitro-5-(2-oxopyrrolidin-1-yl)benzoic acid. To a solution of 3-bromo-5-nitrobenzoic acid (Step I (1), 366 mg, 1.5 mmol) in dioxane (5 mL) were added pyrrolidin-2-one (255 mg, 3 mmol), 4,5-bis(diphenylphosphino)-9,9-dimethylxanthene (130 mg, 0.225 mmol), tris(dibenzylideneacetone)dipalladium(0)-chloroform adduct (78 mg, 0.075 mmol) and cesium carbonate (1.22 g, 3.75 mmol). The mixture was stirred at 95° C. for 2 days. 1N NaOH (100 mL) was added and the mixture was washed with diethyl ether (80 mL) twice. The aqueous layer was neutralized with conc. HCl to pH ~1 and extracted with ethyl acetate (100 mL) twice. The combined organic layers were dried over $Na_2SO_4$, and concentrated in vacuo to give 310 mg of the title compound (83% yield): $^1H$ NMR ($CD_3OD$, 500 MHz) δ ppm 2.25 (2H, m), 2.68 (2H, m), 4.04 (2H, m), 8.55 (1H, m), 8.58 (1H, m), 8.90 (1H, m). MS (ESI) (M−H)⁻ 249.09.

Step I (3): 3-Amino-5-(2-oxopyrrolidin-1-yl)benzoic acid. A suspension of 3-nitro-5-(2-oxopyrrolidin-1-yl)benzoic acid (Step I (2), 180 mg) and palladium on carbon (10 wt %, 50 mg) in MeOH (15 mL) was shaken in hydrogenator under hydrogen at 50 psi for 3 h. The mixture was filtered and concentrated in vacuo to give 140 mg of the title compound: $^1H$ NMR ($CD_3OD$, 500 MHz) δ ppm 2.16 (2H, m), 2.59 (2H, m), 3.89 (2H, t, J=5 Hz), 7.21 (1H, m), 7.26 (1H, m), 7.49 (1H, m). MS (ESI) (M+H)⁺ 221.14.

Step I (4): 3-Hydroxy-5-(2-oxopyrrolidin-1-yl)benzoic acid. To a solution of 3-amino-5-(2-oxopyrrolidin-1-yl)benzoic acid (Step I (3), 140 mg, 0.63 mmol) in 2N HCl (2 mL) were added MeOH (2 mL) followed by $NaNO_2$ (88 mg, 1.26 mmol) in portions at −10° C. After the mixture was warmed up to 0° C., $H_2O$ (3 mL) was added to the above mixture and the mixture was stirred at 95° C. for 1 h. 0.1N HCl (30 mL) was added and the mixture was extracted with ethyl acetate (50 mL) three times. The combined organic layers were dried over sodium sulfate, filtered and concentrated in vacuo to give 130 mg of the title compound: $^1H$ NMR ($CD_3OD$, 500 MHz) δ ppm 2.19 (2H, m), 2.62 (2H, m), 3.94 (2H, m), 7.27 (1H, m), 7.47 (1H, m), 7.66 (1H, m). MS (ESI) (M−H)⁻ 220.12.

Step I (5): Preparation of (2R,4R)-tert-butyl 2-((1S,2S)-1-(tert-butyldimethylsilyloxy)-3-(3,5-difluorophenyl)-2-(3-hydroxy-5-(2-oxopyrrolidin-1-yl)benzamido)propyl)-4-propoxypyrrolidine-1-carboxylate. To a solution of 3-hydroxy-5-(2-oxopyrrolidin-1-yl)benzoic acid (Step I (4), 56 mg, 0.25 mmol) in DMF (1 mL) was added HATU (125 mg, 0.33 mmol) followed by (2R,4R)-tert-butyl 2-((1S,2S)-2-amino-1-(tert-butyldimethylsilyloxy)-3-(3,5-difluorophenyl)propyl)-4-propoxypyrrolidine-1-carboxylate (Example 1, Step 1 (A), 133 mg, 0.25 mmol) in dichloromethane (1.5 mL) and Hunig's base (65 mg, 0.5 mmol) and the reaction mixture was stirred at rt overnight. Ethyl acetate (100 mL) was added and the mixture was washed with $H_2O$ and concentrated under vacuum. The crude mixture was purified by silica gel Flash Chromatography (0% to 20% to 40% to 60% EtOAc/Hexane step gradient) to give 65 mg of the title compound: $^1H$ NMR ($CDCl_3$, 500 MHz) δ ppm 0.01 (3H, s), 0.09 (3H, s), 0.85-0.90 (12H, s), 1.45-1.53 (11H, m), 2.09-2.21 (3H, m), 2.26-2.30 (1H, m), 2.62 (1H, dd, J=5, 10 Hz), 2.66 (1H, dd, J=10, 15 Hz), 2.78 (2H, s), 3.07 (1H, dd, J=5, 15 Hz), 3.16 (1H, dd, J=5, 10 Hz), 3.28-3.38 (2H, m), 3.75-3.99 (4H, m), 4.03-4.09 (1H, m), 4.21 (1H, m), 4.37-4.44 (1H, m), 6.54 (1H, m), 6.70 (1H, d, J=5 Hz), 6.78 (1H, d, J=5 Hz), 6.90 (1H, s), 7.02 (1H, s), 7.70 (1H, s), 7.86 (1H, d, J=10 Hz). MS (ESI) (M+H)⁺ 732.43.

Preparation J (2R,4R)-tert-butyl 4-(allyloxy)-2-((1S,2S)-2-(benzyloxycarbonyl)-1-(tert-butyldimethylsilyloxy)-3-phenylpropyl)pyrrolidine-1-carboxylate

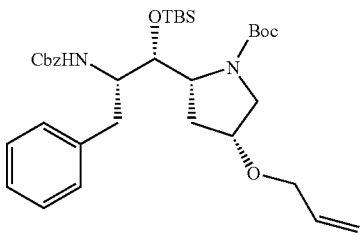

In a manner identical to the preparation of the compound of Preparation B, but using hydrocinnamic acid, (S)-4-benzyl-3-((3-phenyl)propanoyl)-oxazolidin-2-one was prepared. In a manner identical to the preparation of the compound of Preparation A, but using the above starting material, the title compound of Preparation J was prepared. $^1H$ NMR (500 MHz, $CDCl_3$) δ ppm 0.02 (s, 3H) 0.07 (s, 3H) 0.92 (s, 10H) 1.47 (s, 9H) 1.69 (s, 1H) 2.16 (s, 2H) 2.40 (d, J=11.90 Hz, 1H) 3.16 (d, J=13.73 Hz, 2H) 3.91 (m, 4H) 4.19 (dd, J=5.95, 4.42 Hz, 1H) 4.92 (m, 2H) 5.15 (d, J=9.46 Hz, 1H) 5.25 (d, J=17.09 Hz, 1H) 5.86 (m, 1H) 7.26 (m, 11H)

MS (ESI) (M+H−Boc)⁺525.23

Example 1

N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)benzamide

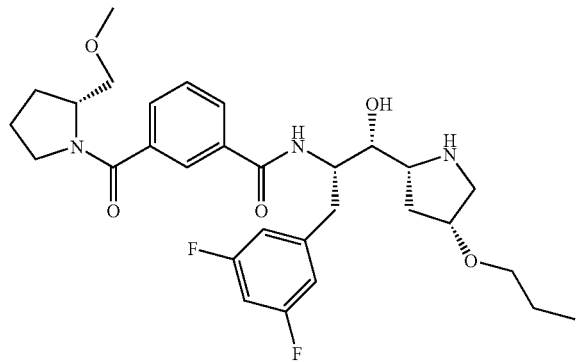

Step 1 (A): (2R,4R)-tert-butyl 2-((1S,2S)-2-amino-1-(tert-butyldimethylsilyloxy)-3-(3,5-difluorophenyl)propyl)-4-propoxypyrrolidine-1-carboxylate. To a solution of (2R,4R)-tert-butyl 4-(allyloxy)-2-((1S,2S)-2-(benzyloxycarbonyl)-1-(tert-butyldimethylsilyloxy)-3-(3,5-difluorophenyl)propyl) pyrrolidine-1-carboxylate (Preparation A, 1.1 g, 1.17 mmol) in MeOH (25 mL) was added a catalytic amount of Pd on activated charcoal (10 wt %, 150 mg). The reaction mixture was put on hydrogenator at 50 psi for 6 h. The mixture was then filtered and concentrated in vacuo to give the title compound ready for next step without purification: $^1$H NMR (CDCl$_3$, 500 MHz) δ 0.02 (6H, s), 0.87 (3H, m), 0.89 (9H, s), 1.12 (1H, m), 1.44 (9H, s), 1.52 (2H, m), 2.12-2.16 (2H, m), 2.33 (1H, t, J=10 Hz), 2.91-3.04 (3H, m), 3.27-3.38 (2H, m), 3.78-3.89 (2H, m), 4.06-4.07 (2H, m), 4.18 (1H, s), 6.58-6.61 (1H, m), 6.71-6.72 (2H, m). MS (ESI) (M+H)$^+$ 529.25.

Step 1 (B): 2R,4R)-tert-butyl 2-((1S,2S)-1-(tert-butyldimethylsilyloxy)-3-(3,5-difluorophenyl)-2-(3-(methoxycarbonyl)benzamido)propyl)-4-propoxypyrrolidine-1-carboxylate. To a solution of 3-(methoxycarbonyl)benzoic acid (450 mg, 2.5 mmol) in dichloromethane (20 mL) and DMF (5 mL) was added Hunig's base (646 mg, 5.01 mmol) to make a clear solution and HATU (1.08 g, 2.84 mmol) was then added. After stirring for 20 min, the reaction mixture was added (2R,4R)-tert-butyl 2-((1S,2S)-2-amino-1-(tert-butyldimethylsilyloxy)-3-(3,5-difluorophenyl)propyl)-4-propoxypyrrolidine 1-carboxylate (Step 1 (A), 900 mg, 1.67 mmol) and the reaction mixture was stirred at rt overnight. Ethyl acetate (200 mL) was added and the mixture was washed with H$_2$O, dried and concentrated. The crude mixture was purified by silica gel Flash Chromatography (0% to 20% to 40% to 60% to 80% EtOAc/Hexane step gradient) to give 1.02 g of the title compound (88% yield for 2 steps): $^1$H NMR (CDCl$_3$, 500 MHz) δ 0.02 (3H, s), 0.06 (3H, s), 0.84 (9H, s), 0.86-0.89 (3H, m), 1.52 (9H, s), 2.00-2.05 (2H, m), 2.20 (1H, d, J=15 Hz), 2.68 (1H, dd, J=10, 15 Hz), 2.92 (1H, m), 3.27-3.37 (3H, m), 3.76 (1H, dd, J=5, 10 Hz), 3.91 (3H, s), 3.99 (1H, s), 4.07-4.12 (2H, m), 4.64 (1H, m), 6.59 (1H, m), 6.78 (2H, d, J=5 Hz), 7.46-7.49 (1H, m), 8.08 (1H, d, J=10 Hz), 8.12 (1H, d, J=5 Hz), 8.29 (1H, brd s), 8.56 (1H, s). MS (ESI) (M+H)$^+$ 691.33.

Step 1 (C): 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid. To a solution of (2R,4R)-tert-butyl 2-((1S,2S)-1-(tert-butyldimethylsilyloxy)-3-(3,5-difluorophenyl)-2-(3-(methoxycarbonyl)benzamido)propyl)-4-propoxypyrrolidine-1-carboxylate (Step 1 (B), 330 mg, 0.48 mmol) in MeOH (5 mL) was added a solution of LiOH (23 mg, 0.96 mmol) in H$_2$O (1 mL). This reaction mixture was stirred at rt for 24 h. Ethyl ether (150 mL) was added to the mixture and washed with 1N HCl, H$_2$O, dried (Na$_2$SO$_4$), and concentrated in vacuo to give 300 mg of the title compound: $^1$H NMR (CDCl$_3$, 500 MHz) δ 0.04 (3H, s), 0.11 (3H, s), 0.90-0.93 (3H, m), 0.96 (9H, s), 1.46 (9H, s), 1.57 (2H, m), 2.23-2.29 (1H, m), 2.45-2.50 (1H, m), 2.63 (1H, m), 3.09 (1H, m), 3.26 (1H, dd, J=5, 15 Hz), 3.35-3.39 (1H, m), 3.43-3.48 (1H, m), 3.86 (1H, m), 3.97 (1H, m), 4.13 (1H, m), 4.39 (1H, m), 4.48 (1H, m), 6.47-6.50 (1H, m), 6.90 (2H, d, J=5 Hz), 7.44-7.47 (1H, m), 8.08 (1H, d, J=5 Hz), 8.15 (1H, d, J=10 Hz), 8.31 (1H, d, J=10 Hz), 8.73 (1H, s). MS (ESI) (M+H)$^+$ 677.30.

Step 1 (D): (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)benzamido)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid (Step 1 (C), 50 mg, 0.074 mmol) in dichloromethane (2 mL) and DMF (5 mL) was added Hunig's base (28 mg, 0.222 mmol) to make a clear solution and HATU (36 mg, 0.0962 mmol) was then added. After stirring for 20 min, the reaction mixture was added (R)-2-(methoxymethyl)pyrrolidine (17 mg, 0.148 mmol) and the reaction mixture was stirred at rt overnight. Ethyl acetate (100 mL) was added and the mixture was washed with Brine, H$_2$O, dried and concentrated to give 45 mg of the title compound (79% yield): $^1$H NMR (CDCl$_3$, 500 MHz) δ 0.02 (3H, s), 0.05 (3H, s), 0.83 (9H, s), 0.86-0.89 (3H, m), 1.48-1.51 (11H, m), 1.72 (1H, m), 1.91-2.07 (4H, m), 2.18 (1H, d, J=15 Hz), 2.64 (1H, dd, J=10, 15 Hz), 2.90-2.94 (1H, m), 3.02 (1H, brd s), 3.28-3.38 (6H, m), 3.48 (1H, m), 3.55 (1H, m), 3.67 (1H, m), 3.74 (1H, m), 3.98 (1H, m), 4.04-4.12 (2H, m), 4.42 (1H, m), 4.59 (1H, m), 6.57-6.60 (1H, m), 6.76 (2H, d, J=5 Hz), 7.41-7.44 (1H, m), 7.60-7.62 (1H, m), 7.88 (1H, d, J=5 Hz), 7.96 (1H, s), 8.08 (1H, brd s). MS (ESI) (M+H)$^+$ 774.40.

Step 1 (E): N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)benzamide. The solution of (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)benzamido)propyl)-4-propoxypyrrolidine-1-carboxylate (Step 1 (D), 45 mg) in mixture of trifluoroacetic acid (1.5 mL), acetic acid (1.5 mL), THF (1 mL) and H$_2$O (0.5 mL) was stirred at 70° C. for 7 h. The solvent was removed and the mixture was purified by reverse phase HPLC (30×50 mm Xterra column, 30-100% methanol/H$_2$O/0.1% TFA) to give the title compound of example 1: $^1$H NMR (CD$_3$OD, 500 MHz) δ 0.96-0.99 (3H, m), 1.63 (2H, m), 1.80 (1H, m), 2.03 (2H, m), 2.09-2.20 (2H, m), 2.52 (1H, m), 2.88 (1H, dd, J=10, 15 Hz), 3.02 (1H, brd s), 3.33-3.50 (9H, m), 3.65 (2H, m), 3.81 (1H, m), 4.06 (1H, m), 4.20-4.29 (2H, m), 4.39 (1H, m), 6.75 (1H, m), 6.90 (2H, m), 7.52-7.55 (1H, m), 7.66 (1H, d, J=5 Hz), 7.75-7.78 (2H, m), 8.47 (1H, d, J=10 Hz). MS (ESI) (M+H)+ 560.28.

Example 2

N[1]-((1R,2S)-3-(3,5-difluorophenyl)-1-hydroxy-1-((2R,4R)-4-propoxypyrrolidin-2-yl)propan-2-yl)-N[3]-methyl-N[3]-propylisophthalamide

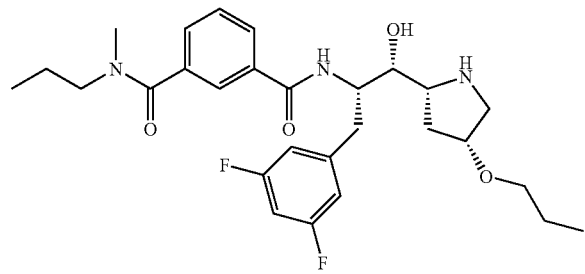

Step 2 (A): (2R,4R)-tert-butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid (Step 1 (C), 60 mg, 0.088 mmol) in dichloromethane (2 mL) was added Hunig's base (34 mg, 0.267 mmol) to make a clear solution and HATU (45 mg, 0.12 mmol) was then added. After stirring for 20 min, the reaction mixture was added N-methylpropan-1-amine (13 mg, 0.178 mmol) and the reaction mixture was stirred at rt overnight. Ethyl acetate (100 mL) was added and the mixture was washed with Brine, $H_2O$, dried and concentrated to give 55 mg of the title compound (85% yield): $^1$H NMR (CDCl$_3$, 500 MHz) δ 0.02 (3H, s), 0.05 (3H, s), 0.71-0.76 (1H, m), 0.83 (9H, s), 0.87 (3H, m), 0.91-1.00 (2H, m), 1.40-1.53 (12H, m), 1.60-1.67 (1H, m), 2.01-2.05 (1H, m), 2.17-2.20 (1H, m), 2.64 (1H, m), 2.89-3.04 (4H, m), 3.17 (1H, brd s), 3.27-3.36 (3H, m), 3.48 (1H, brd s), 3.74 (1H, m), 3.97 (1H, m), 4.04-4.11 (2H, m), 4.58 (1H, m), 6.58 (1H, m), 6.76 (2H, d, J=5 Hz), 7.41-7.48 (2H, m), 7.86 (2H, s), 8.13 (1H, brd s).

Step 2 (B): N[1]-((1R,2S)-3-(3,5-difluorophenyl)-1-hydroxy-1-((2R,4R)-4-propoxypyrrolidin-2-yl)propan-2-yl)-N[3]-methyl-N[3]-propylisophthalamide. The solution of (2R,4R)-tert-butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate (Step 2 (A), 55 mg) in mixture of trifluoroacetic acid (1.5 mL), acetic acid (1.5 mL), THF (1 mL) and $H_2O$ (0.5 mL) was stirred at 70° C. for 7 h. The solvent was removed and the mixture was purified by reverse phase HPLC (30×50 mm Xterra column, 30-100% methanol/H$_2$O/0.1% TFA) to give 34 mg of the title compound of example 2 (85% yield): $^1$H NMR (CD$_3$OD, 500 MHz) δ 0.74 (1H, m), 0.96-0.99 (3H, m), 1.02 (2H, m), 1.54-1.66 (3H, m), 1.73 (1H, 2.17 (1H, m), 2.48-2.54 (1H, m), 2.87 (1H, m), 3.21 (1H, m), 3.33-3.49 (8H, m), 3.53 (1H, m), 3.82 (1H, m), 4.06 (1H, dd, J=5, 10 Hz), 4.20-4.28 (2H, m), 6.74 (1H, m), 6.90 (2H, d, J=5 Hz), 7.52-7.57 (2H, m), 7.66 (1H, m), 7.76 (1H, d, J=5 Hz). MS (ESI) (M+H)+ 518.28.

Example 3

N[1]-butyl-N[3]-((1R,2S)-3-(3,5-difluorophenyl)-1-hydroxy-1-((2R,4R)-4-propoxypyrrolidin-2-yl)propan-2-yl)-N[1]-methylisophthalamide

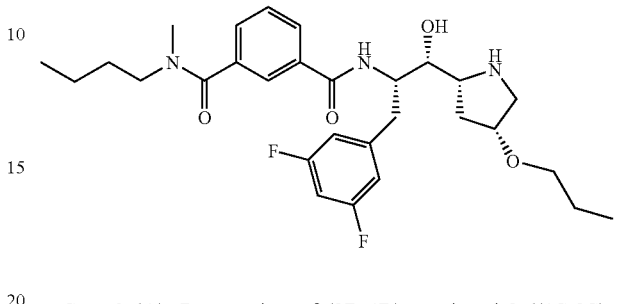

Step 3 (A): Preparation of (2R,4R)-tert-butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid (Step 1 (C), 66 mg, 0.10 mmol) in dichloromethane (2 mL) were added HATU (46 mg, 0.12 mmol) and N-methylbutan-1-amine (12 mg, 0.13 mmol) and the reaction mixture was stirred at rt overnight. The crude mixture was purified by silica gel Flash Chromatography (0% to 20% to 40% to 60% to 80% EtOAc/Hexane step gradient) to give 60 mg of the title compound (80% yield): $^1$H NMR (CDCl$_3$, 500 MHz) δ 0.02 (3H, s), 0.05 (3H, s), 0.75 (2H, m), 0.83 (9H, s), 0.88 (3H, m), 0.93-0.96 (2H, m), 1.12 (1H, m), 1.35-1.41 (1H, m), 1.48-1.53 (11H, m), 1.61 (1H, m), 2.01-2.06 (1H, m), 2.19 (1H, d, J=10 Hz), 2.66 (1H, m), 2.89-2.93 (3H, m), 3.04 (1H, s), 3.21 (1H, brd s), 3.27-3.36 (3H, m), 3.51 (1H, brd s), 3.75 (1H, dd, J=5, 15 Hz), 3.97 (1H, m), 4.05-4.11 (2H, m), 4.60 (1H, m), 6.59 (1H, m), 6.76 (2H, d, J=5 Hz), 7.41-7.48 (2H, m), 7.87 (2H, s), 8.13 (1H, brd s). MS (ESI) (M+H)+ 746.36.

Step 3 (B): Preparation of N[1]-butyl-N[3]-((1R,2S)-3-(3,5-difluorophenyl)-1-hydroxy-1-((2R,4R)-4-propoxypyrrolidin-2-yl)propan-2-yl)-N[1]-methylisophthalamide. The solution of (2R,4R)-tert-butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate (Step 3 (A), 60 mg) in mixture of trifluoroacetic acid (1.0 mL), acetic acid (1.5 mL), THF (0.5 mL) and $H_2O$ (0.5 mL) was stirred at 70° C. for 6 h. The solvent was removed and the mixture was purified by reverse phase HPLC (30×50 mm Xterra column, 30-100% methanol/H$_2$O/0.1% TFA) to give the title compound of example 3: $^1$H NMR (CD$_3$OD, 500 MHz) δ 0.76-0.79 (2H, m), 0.96-0.98 (3H, m), 1.01-1.04 (2H, m), 1.14 (1H, m), 1.41-1.47 (1H, m), 1.52-1.55 (1H, m), 1.59-1.70 (3H, m), 2.17 (1H, m), 2.48-2.54 (1H, m), 2.87 (1H, m), 3.24 (1H, m), 3.33-3.50 (7H, m), 3.57 (1H, m), 3.82 (1H, m), 4.06 (1H, dd, J=5, 10 Hz), 4.21-4.28 (2H, m), 6.74 (1H, t, J=10 Hz), 6.90 (2H, d, J=5 Hz), 7.52-7.55 (2H, m), 7.66 (1H, s), 7.76 (1H, d, J=5 Hz). MS (ESI) (M+H)+ 532.25.

Example 4

N$^1$-((1R,2S)-3-(3,5-difluorophenyl)-1-hydroxy-1-((2R,4R)-4-propoxypyrrolidin-2-yl)propan-2-yl)-N$^3$,N$^3$-dipropylisophthalamide

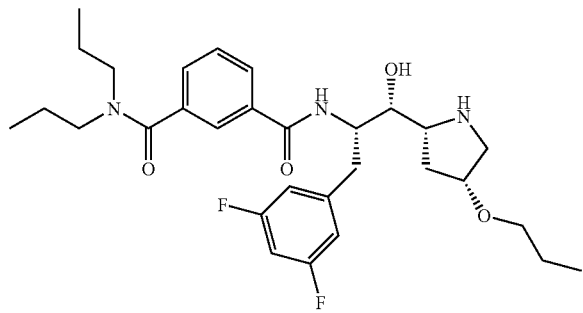

Step 4 (A): N$^1$-((1S,2S)-1-((2R,4R)-4-(allyloxy)-1-benzhydrylpyrrolidin-2-yl)-3-(3,5-difluorophenyl)-1-hydroxypropan-2-yl)-N$^3$,N$^3$-dipropylisophthalamide. To a solution of 3-(dipropylcarbamoyl)benzoic acid (31 mg, 0.12 mmol) in dichloromethane (3 mL) were added Hunig's base (43 mg, 0.33 mmol) and HATU (54 mg, 0.143 mmol). After stirring for 20 min, the reaction mixture was added (1S,2S)-1-((2R,4R)-4-(allyloxy)-1-benzhydrylpyrrolidin-2-yl)-2-amino-3-(3,5-difluorophenyl)propan-1-ol (Preparation (C), 54 mg, 0.11 mmol) and the reaction mixture was stirred at rt overnight. The crude mixture was purified by silica gel Flash Chromatography (0% to 20% to 40% to 50% EtOAc/Hexane step gradient) to give 70 mg of the title compound (89% yield): $^1$H NMR (CDCl$_3$, 500 MHz) δ 0.74 (3H, brd s), 1.00 (3H, brd s), 1.53 (2H, brd s), 1.73 (2H, brd s), 2.02-2.09 (1H, m), 2.17 (1H, d, J=10 Hz), 2.26 (1H, dd, J=5, 10 Hz), 2.68 (1H, d, J=10 Hz), 2.84 (1H, dd, J=5, 15 Hz), 2.96 (1H, dd, J=5, 15 Hz), 3.09 (1H, d, J=10 Hz), 3.16 (2H, brd s), 3.25 (1H, d, J=10 Hz), 3.49 (2H, brd s), 3.91-3.93 (2H, m), 3.96-4.11 (3H, m), 4.50 (1H, s), 4.91 (1H, d, J=10 Hz), 5.22 (1H, dd, J=5, 10 Hz), 5.31 (1H, m), 5.90-5.98 (1H, m), 6.64-6.69 (3H, m), 6.91-6.97 (3H, m), 7.15-7.20 (3H, m), 7.22-7.25 (2H, m), 7.34 (2H, d, J=5 Hz), 7.47-7.57 (4H, m). MS (ESI) (M+H)$^+$ 710.37.

Step 4 (B): N$^1$-((1R,2S)-3-(3,5-difluorophenyl)-1-hydroxy-1-((2R,4R)-4-propoxypyrrolidin-2-yl)propan-2-yl)-N$^3$,N$^3$-dipropylisophthalamide. To a solution of N$^1$-((1S,2S)-1-((2R,4R)-4-(allyloxy)-1-benzhydrylpyrrolidin-2-yl)-3-(3,5-difluorophenyl)-1-hydroxypropan-2-yl)-N$^3$,N$^3$-dipropylisophthalamide (Step 4 (A), 70 mg) in MeOH (5 mL) were added a catalytic amount of Pd on activated charcoal (10 wt %, 20 mg) and acetic acid (0.5 mL). The reaction mixture was put on hydrogenator at 50 psi for 3.5 h. The mixture was then filtered and concentrated in vacuo. The crude mixture was purified by silica gel Flash Chromatography (0% to 5% to 10% to 15% to 20% MeOH/dichloromethane step gradient) to give the title compound of example 4 (40 mg, 74% yield): $^1$H NMR (CD$_3$OD, 500 MHz) δ 0.70-0.73 (3H, m), 0.95-0.98 (3H, m), 1.00-1.03 (3H, m), 1.54 (2H, m), 1.62 (2H, m), 1.74 (2H, m), 2.09 (1H, m), 2.39-2.44 (1H, m), 2.88 (1H, m), 3.16-3.24 (3H, m), 3.29 (1H, m), 3.38-3.50 (6H, m), 3.66 (1H, m), 4.02 (1H, m), 4.19-4.23 (1H, m), 4.24-4.29 (1H, m), 6.73 (1H, m), 6.89-6.92 (2H, m), 7.50-7.56 (2H, m), 7.64 (1H, s), 7.78-7.80 (1H, m). MS (ESI) (M+H)+ 546.33.

Example 5

N$^1$-((1S,2S)-3-(3,5-difluorophenyl)-1-hydroxy-1-((R)-morpholin-3-yl)propan-2-yl)-N$^3$,N$^3$-dipropylisophthalamide

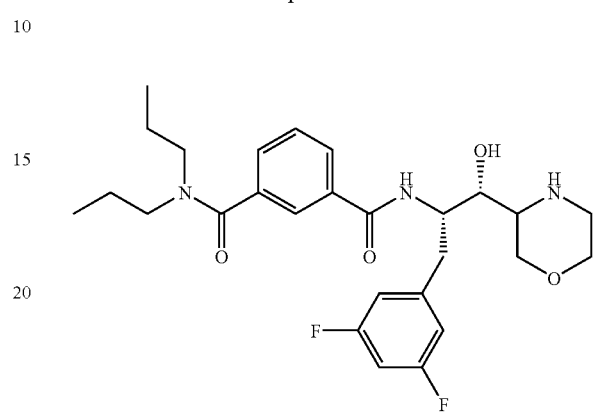

Step 5 (A): N$^1$-((1S,2S)-1-((R)-4-benzhydrylmorpholin-3-yl)-3-(3,5-difluorophenyl)-1-hydroxypropan-2-yl)-N$^3$,N$^3$-dipropylisophthalamide. To a solution of 3-(dipropylcarbamoyl)benzoic acid (Preparation E, 14 mg, 0.055 mmol) in dichloromethane (1 mL) was added Hunig's base (18 mg, 0.14 mmol) to make a clear solution and HATU (25 mg, 0.064 mmol) was then added. After stirring for 20 min, the reaction mixture was added (1S,2S)-2-amino-1-((R)-4-benzhydrylmorpholin-3-yl)-3-(3,5-difluorophenyl)propan-1-ol (Preparation D, (20 mg, 0.046 mmol) and the reaction mixture was stirred at rt overnight. Dichloromethane (100 mL) was added and washed with H$_2$O (50 mL) twice, dried over Na$_2$SO$_4$, and concentrated to give the title compound as a crude product ready for next step without purification: $^1$H NMR (CD$_3$OD, 500 MHz) δ 0.71 (3H, m), 1.01 (3H, m), 1.52 (2H, m), 1.74 (2H, m), 2.52 (1H, d, J=5 Hz), 2.63 (2H, dd, J=5, 15 Hz), 2.71 (1H, m), 3.12-3.19 (3H, m), 3.44-3.49 (3H, m), 3.94-3.99 (2H, m), 4.04 (1H, m), 4.58 (1H, m), 5.06 (1H, m), 5.50 (1H, s), 6.76 (1H, m), 6.92-6.95 (2H, m), 7.14-7.19 (3H, m), 7.25-7.32 (3H, m), 7.44 (2H, m), 7.49-7.55 (2H, m), 7.58 (2H, d, J=10 Hz), 7.63 (1H, s), 7.73-7.76 (1H, m).

Step 5 (B): N$^1$-((1S,2S)-3-(3,5-difluorophenyl)-1-hydroxy-1-((R)-morpholin-3-yl)propan-2-yl)-N$^3$,N$^3$-dipropylisophthalamide. To a solution of N$^1$-((1S,2S)-1-((R)-4-benzhydrylmorpholin-3-yl)-3-(3,5-difluorophenyl)-1-hydroxypropan-2-yl)-N$^3$,N$^3$-dipropylisophthalamide (Step 5 (A), 30 mg) in MeOH (5 mL) were added a catalytic amount of Pd on activated charcoal (10 wt %, 15 mg) and acetic acid (0.2 mL). The reaction mixture was put on hydrogenator at 50 psi for 3 h. The mixture was then filtered and concentrated in vacuo and purified by reverse phase HPLC to give the title compound of example 5: $^1$H NMR (CD$_3$OD, 500 MHz) δ 0.72 (3H, t, J=5 Hz), 1.02 (3H, m), 1.54 (2H, m), 1.74 (2H, m), 2.87 (1H, m), 3.17 (2H, m), 3.26-3.39 (3H, m), 3.48-3.51 (3H, m), 3.72 (1H, m), 3.84 (1H, m), 4.00 (2H, dd, J=5, 10 Hz), 4.19 (1H, m), 4.40 (1H, m), 6.75 (1H, m), 6.87-6.90 (2H, m), 7.53-7.57 (2H, m), 7.62 (1H, s), 7.76-7.78 (1H, m). MS (ESI) (M+H)$^+$ 504.25.

Example 6

N$^1$-butyl-N$^3$-((1R,2S)-3-(3,5-difluorophenyl)-1-hydroxy-1-((2R)-4-hydroxy-4-phenylpyrrolidin-2-yl)propan-2-yl)-N$^1$-methylisophthalamide

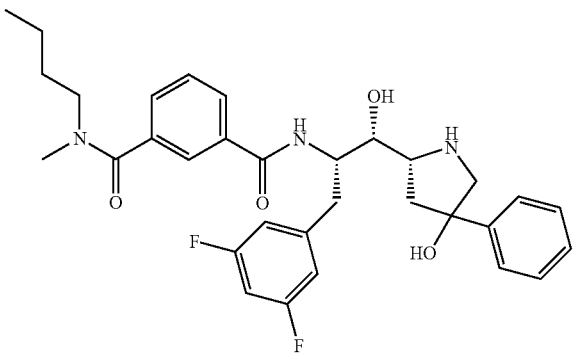

Step 6 (A): (2R,4R)-tert-butyl 2-((1S,2S)-2-(benzyloxycarbonyl)-1-(tert-butyldimethylsilyloxy)-3-(3,5-difluorophenyl)propyl)-4-hydroxypyrrolidine-1-carboxylate. To a solution of (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate (Preparation A, 730 mg, 1.11 mmol) in H$_2$O/EtOH (0.8/7 mL) were added RhCl(PPh$_3$)$_3$ (77 mg, 0.083 mmol) and DABCO (25 mg, 0.22 mmol). The mixture was stirred at 140° C. for 3 h and then cooled to rt. MeOH (20 mL) and 1N NaOH solution (5 mL) were added followed by 0.1% KMnO$_4$ solution (5 mL) dropwise. The reaction mixture was stirred at rt for 1.5 h and quenched with H$_2$O. The mixture was extracted with ethyl acetate (300 mL) twice and solvent was removed. Flash chromatography (silica gel, 0% to 10% to 20% to 35% EtOAc/Hexane step gradient) gave the title compound (530 mg, 77% yield): $^1$H NMR (CDCl$_3$, 500 MHz) δ 0.10-0.13 (6H, m), 0.93 (9H, s), 1.22-1.27 (2H, m), 1.46 (9H, s), 2.13 (2H, s), 3.23-3.25 (2H, m), 3.54-3.89 (2H, m), 4.12 (1H, m), 4.22 (1H, s), 4.32 (1H, m), 4.86-5.03 (3H, m), 6.60-6.70 (3H, m), 7.17 (2H, s), 7.27-7.28 (3H, m). MS (ESI) (M+H)$^+$ 621.25.

Step 6 (B): Preparation of (2R,4R)-tert-butyl 2-((1S,2S)-2-amino-1-(tert-butyldimethylsilyloxy)-3-(3,5-difluorophenyl)propyl)-4-hydroxypyrrolidine 1-carboxylate. To a solution of (2R,4R)-tert-butyl 2-((1S,2S)-2-(benzyloxycarbonyl)-1-(tert-butyldimethylsilyloxy)-3-(3,5-difluorophenyl)propyl)-4-hydroxypyrrolidine-1-carboxylate (Step 6 (A), 330 mg) in MeOH (8 mL) was added a catalytic amount of Pd on activated charcoal (10 wt %, 50 mg). The reaction mixture was put on hydrogenator at 50 psi for 3 h. The mixture was then filtered and concentrated in vacuo to give the title compound (230 mg, 89% yield): $^1$H NMR (CDCl$_3$, 500 MHz) δ 0.11-0.13 (6H, m), 0.92 (9H, s), 1.46 (9H, s), 2.21 (1H, m), 2.35 (1H, t, J=10 Hz), 2.46 (1H, d, J=15 Hz), 3.10 (2H, dd, J=5, 10 Hz), 3.29 (1H, d, J=10 Hz), 3.46 (1H, m,) 4.21-4.36 (3H, m), 6.64-6.73 (3H, m). MS (ESI) (M+H)$^+$ 487.21.

Step 6 (C): Preparation of (2R,4R)-tert-butyl 2-((1S,2S)-1-(tert-butyldimethylsilyloxy)-2-(3-(carbamoyl)benzamido)-3-(3,5-difluorophenyl)propyl)-4-hydroxypyrrolidine-1-carboxylate. To a solution of 3-(butyl(methyl)carbamoyl)benzoic acid (Preparation F, 146 mg, 0.62 mmol) in dichloromethane (8 mL) was added Hunig's base (182 mg, 1.41 mmol) to make a clear solution and HATU (250 mg, 0.66 mmol) was then added. After stirring for 30 min, the reaction mixture was added (2R,4R)-tert-butyl 2-((1S,2S)-2-amino-1-(tert-butyldimethylsilyloxy)-3-(3,5-difluorophenyl)propyl)-4-hydroxypyrrolidine-1-carboxylate (Step 6 (B), 230 mg, 0.47 mmol) and the reaction mixture was stirred at rt for 3 h. The crude mixture was purified by silica gel Flash Chromatography (0% to 20% to 40% to 60% EtOAc/Hexane step gradient) to give 350 mg of the title compound: $^1$H NMR (CDCl$_3$, 500 MHz) δ 0.01-0.07 (6H, m), 0.66 (2H, m), 0.83 (9H, s), 1.02 (1H, m), 1.30 (1H, m), 1.38 (9H, s), 1.53 (1H, m), 2.10 (2H, s), 2.60 (1H, m), 2.70 (1H, m), 2.79 (2H, s), 2.89-2.94 (2H, m), 3.09-3.16 (3H, m), 3.43 (1H, brd s), 3.56 (1H, dd, J=5, 10 Hz), 3.97-4.02 (2H, m), 4.16 (1H, brd s), 4.31-4.38 (2H, m), 6.48 (1H, m), 6.65-6.71 (2H, m), 7.25-7.34 (2H, m), 7.56-7.63 (2H, m), 7.83 (1H, s). MS (ESI) (M+H)$^+$ 704.43.

Step 6 (D): (R)-tert-butyl 2-((1S,2S)-1-(tert-butyldimethylsilyloxy)-2-(3-(carbamoyl)benzamido)-3-(3,5-difluorophenyl)propyl)-4-oxopyrrolidine-1-carboxylate. To a solution of (2R,4R)-tert-butyl 2-((1S,2S)-1-(tert-butyldimethylsilyloxy)-2-(3-(carbamoyl)benzamido)-3-(3,5-difluorophenyl)propyl)-4-hydroxypyrrolidine-1-carboxylate (Step 6 (C), (320 mg, 0.455 mmol) in dichloromethane (10 mL) was added Dess-Martin reagent (386 mg, 0.91 mmol) and the mixture was stirred at rt for 5 h. Ethyl acetate (300 mL) was added and the mixture was washed with 1N NaOH, H$_2$O, dried over Na$_2$SO$_4$ and concentrated to give the title compound (280 mg): $^1$H NMR (CDCl$_3$, 500 MHz) δ 0.01 (3H, s), 0.10 (3H, s), 0.71 (2H, m), 0.86 (9H, s), 0.95-0.97 (2H, m), 1.07 (1H, m), 1.44 (11H, m), 1.62 (1H, m), 2.69-2.75 (3H, m), 2.81-2.86 (2H, m), 3.03 (1H, s), 3.12-3.22 (2H, m), 3.47-3.54 (1H, m), 3.64 (1H, d, J=20 Hz), 3.82 (1H, d, J=20 Hz), 4.23-4.27 (2H, m), 4.50 (1H, m), 6.55 (1H, t, J=10 Hz), 6.78 (2H, m), 7.25 (1H, s), 7.36 (1H, s), 7.43-7.52 (2H, m). MS (ESI) (M+H)$^+$ 702.31.

Step 6 (E): Preparation of (2R)-tert-butyl 2-((1S,2S)-1-(tert-butyldimethylsilyloxy)-2-(3-(carbamoyl)benzamido)-3-(3,5-difluorophenyl)propyl)-4-hydroxy-4-phenylpyrrolidine-1-carboxylate. To a solution of (R)-tert-butyl 2-((1S,2S)-1-(tert-butyldimethylsilyloxy)-2-(3-(carbamoyl)benzamido)-3-(3,5-difluorophenyl)propyl)-4-oxopyrrolidine-1-carboxylate (Step 6 (D), 25 mg, 0.036 mmol) in THF (1 mL) was added phenylmagnesium bromide (3.0 M in diethyl ether, 0.0144 mL, 0.0432 mmol) at −20° C. After stirring for 20 min, the reaction mixture was warmed up to 0° C. and stirred for 30 min and another portion of phenylmagnesium bromide (3.0 M in diethyl ether, 0.0144 mL, 0.0432 mmol) was added and the reaction mixture was stirred at rt for 2 h. Another portion of phenylmagnesium bromide (3.0 M in diethyl ether, 0.024 mL, 0.072 mmol) was added and the reaction mixture was stirred at rt for 2 days. H$_2$O (50 mL) was added and the mixture was extracted with ethyl acetate, dried (Na$_2$SO$_4$) and concentrated. The crude mixture was purified by silica gel Flash Chromatography (0% to 20% to 40% EtOAc/Hexane step gradient) to give 12 mg of the title compound (42% yield): $^1$H NMR (CDCl$_3$, 500 MHz) δ 0.15 (3H, s), 0.20 (3H, s), 0.72-0.79 (1H, m), 0.86 (1H, m), 0.96 (9H, s), 1.08-1.11 (1H, m), 1.45 (9H, s), 1.58-1.62 (1H, m), 1.77 (3H, s), 2.52 (2H, d, J=5 Hz), 2.63 (1H, m), 2.87-3.04 (3H, m), 3.16 (1H, brd s), 3.28 (1H, d, J=10 Hz), 3.51 (1H, brd s), 3.66 (1H, d, J=15 Hz), 3.78 (1H, d, J=10H), 3.95 (1H, m), 4.30 (1H, s), 4.56 (2H, s), 6.59 (1H, t, J=10 Hz), 6.78 (2H, d, J=5 Hz), 7.14 (1H, m), 7.24-7.27 (1H, m), 7.34 (2H, m), 7.39 (1H, m), 7.46-7.50 (3H, m), 7.68 (2H, m). MS (ESI) (M+H)$^+$ 780.49.

Step 6 (F): Preparation of N¹-butyl-N³-((1R,2S)-3-(3,5-difluorophenyl)-1-hydroxy-1-((2R)-4-hydroxy-4-phenylpyrrolidin-2-yl)propan-2-yl)-N¹-methylisophthalamide. The solution of (2R)-tert-butyl 2-((1S,2S)-1-(tert-butyldimethylsilyloxy)-2-(3-(carbamoyl)benzamido)-3-(3,5-difluorophenyl)propyl)-4-hydroxy-4-phenylpyrrolidine-1-carboxylate (Step 6 (E), 10 mg) in THF (0.5 mL) was added HCl (4.0 M in dioxane, 0.3 mL) and the mixture was stirred at rt for 1 h and 2 drops of H₂O was added. After stirring for another 1 h, the solvent was removed and purified by reverse phase HPLC (21.2×50 mm PHENOMENEX-LUNA S5 column, flow rate 25 mL/min, gradient time 12 min, 20-100% methanol/H₂O/0.1% TFA) to give 3 mg of the title compound: ¹H NMR (CD₃OD, 500 MHz) δ 0.76 (1H, m), 0.90-0.93 (1H, m), 1.03 (1H, m), 1.14 (1H, dd, J=10, 15 Hz), 1.31 (1H, m), 1.45 (1H, m), 1.65-1.71 (1H, m), 2.64 (1H, d, J=10 Hz), 2.92-2.97 (2H, m), 3.09 (1H, s), 3.24 (1H, m), 3.44 (1H, m), 3.53-3.64 (4H, m), 4.12-4.19 (2H, m), 4.28-4.32 (1H, m), 6.75 (1H, m), 6.92-6.94 (2H, m), 7.32 (1H, m), 7.39 (2H, m), 7.53-7.56 (4H, m), 7.66 (1H, s), 7.76-7.78 (1H, m). MS (ESI) (M+H)⁺ 566.35.

Example 7

N¹-butyl-N³-((1R,2S)-3-(3,5-difluorophenyl)-1-hydroxy-1-((2R)-4-phenylpyrrolidin-2-yl)propan-2-yl)-N¹-methylisophthalamide

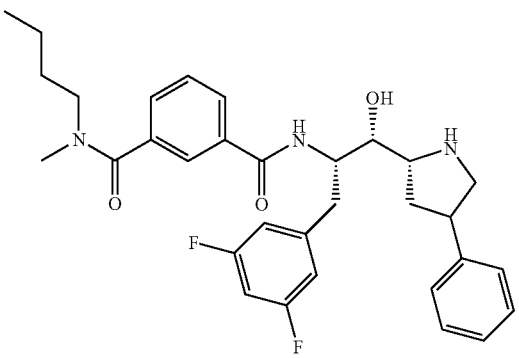

Step 7 (A): (R)-tert-butyl 2-((1S,2S)-1-(tert-butyldimethylsilyloxy)-2-(3-(carbamoyl)benzamido)-3-(3,5-difluorophenyl)propyl)-4-phenyl-2,3-dihydropyrrole-1-carboxylate. To a solution of (2R)-tert-butyl 2-((1S,2S)-1-(tert-butyldimethylsilyloxy)-2-(3-(carbamoyl)benzamido)-3-(3,5-difluorophenyl)propyl)-4-hydroxy-4-phenylpyrrolidine-1-carboxylate (Step 6 (B), 8 mg) in dichloromethane (0.3 mL) was added Et₃SiH (0.5 mL) and the mixture was stirred at rt for 2 h. TFA (0.5 mL) was added and the mixture was stirred at rt for another 2 h. Solvent was removed and TFA (0.5 mL) and Et₃SiH (0.5 mL) were added and the mixture was stirred at rt for 2 days. The mixture was concentrated in vacuum and the crude product was ready for next step without further purification.

Step 7 (B): Preparation of N¹-butyl-N³-((1R,2S)-3-(3,5-difluorophenyl)-1-hydroxy-1-((2R)-4-phenylpyrrolidin-2-yl)propan-2-yl)-N¹-methylisophthalamide. To a solution of (R)-tert-butyl 2-((1S,2S)-1-(tert-butyldimethylsilyloxy)-2-(3-(carbamoyl)benzamido)-3-(3,5-difluorophenyl)propyl)-4-phenyl-2,3-dihydropyrrole-1-carboxylate (Step 7 (A), 15 mg) in MeOH (1 mL) was added a catalytic amount of Pd on activated charcoal (10 wt %, 10 mg). The reaction mixture was put on hydrogenator at 50 psi for 3 h. The mixture was then filtered and concentrated in vacuo. To the above residue were added dioxane (0.5 mL) and 2 drops of H₂O and the mixture was stirred at rt for 2 h. Solvent was removed and the mixture was purified by reverse phase HPLC to give the title compound (9 mg): ¹H NMR (CDCl₃, 500 MHz) δ 0.77 (2H, m), 1.03 (2H, m), 1.14 (1H, dd, J=10, 15 Hz), 1.45 (1H, dd, J=5, 15 Hz), 1.54 (1H, m), 1.69 (1H, m), 2.33 (1H, m), 2.58 (1H, m), 2.89 (1H, m), 2.94 (1H, s), 3.09 (1H, s), 3.23-3.29 (2H, m), 3.44 (1H, dd, J=5, 15 Hz), 3.57 (2H, m), 3.74 (1H, m), 4.00 (1H, m), 4.17 (1H, m), 4.26 (1H, m), 6.74 (1H, t, J=10 Hz), 6.89 (2H, d, J=10 Hz), 7.31 (1H, m), 7.36-7.40 (4H, m), 7.53-7.56 (2H, m), 7.67 (1H, s), 7.76-7.78 (1H, m). MS (ESI) (M+H)⁺ 550.31.

Example 8

N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-methylbenzamide

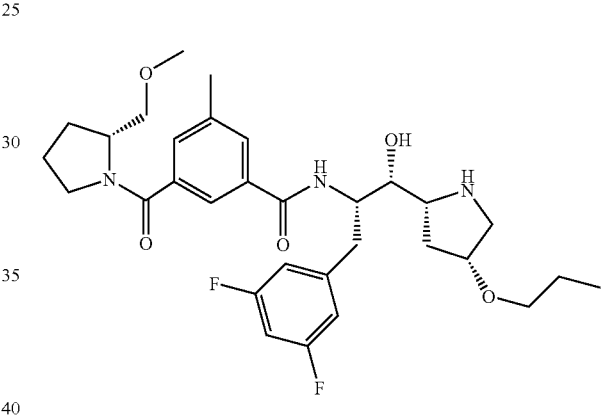

Step 8 (A): (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)-5-methylbenzamido)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)-5-methylbenzoic acid (Preparation G, 28 mg, 0.038 mmol) in dichloromethane (1 mL) was added Hunig's base (14 mg, 0.114 mmol) to make a clear solution and HATU (19 mg, 0.05 mmol) was then added. After stirring for 20 min, the reaction mixture was added (R)-2-(methoxymethyl)pyrrolidine (65 mg, 0.057 mmol) and the reaction mixture was stirred at rt overnight. Ethyl acetate (100 mL) was added and the mixture was washed with Brine, H₂O, dried and concentrated to give 30 mg of the title compound (95% yield): ¹H NMR (CDCl₃, 500 MHz) δ ppm 0.01 (3H, s), 0.06 (3H, s), 0.85 (9H, s), 0.88 (3H, t, J=5 Hz), 1.48-1.54 (11H, m), 1.73 (1H, m), 1.92-22.09 (5H, m), 2.18 (1H, m), 2.38 (3H, s), 2.62 (1H, m), 2.96 (1H, m), 3.05 (1H, m), 3.26-3.39 (5H, m), 3.47 (1H, m), 3.58 (1H, m), 3.68 (1H, m), 3.76 (1H, dd, J=5, 15 Hz), 3.97 (1H, m), 4.04-4.07 (1H, m), 4.11-4.14 (1H, m), 4.41 (1H, brd s), 4.56 (1H, m), 6.59 (1H, m), 6.76 (1H, s), 6.77 (1H, s), 7.43 (1H, s), 7.72 (1H, s), 7.74 (1H, s), 7.98 (1H, brd s). MS (ESI) (M+H)⁺ 788.61.

Step 8 (B): Preparation of N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-methylbenzamide. To a solution of (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)-5-methylbenzamido)propyl)-4-propoxypyrrolidine-1-carboxylate (Step 8 (A), 30 mg) in dioxane containing HCl (4.0 M solution in dioxane, 1 mL) was added 2 drops of $H_2O$ and the mixture was stirred at rt for 3 h. The solvent was removed and the mixture was purified by reverse phase HPLC (20×50 mm YMC ODS-A S5 column, 34-82% methanol/$H_2O$/0.1% TFA) to give 12 mg of the title compound: $^1$H NMR ($CD_3OD$, 500 MHz) δ ppm 0.97 (3H, m), 1.63 (2H, m), 1.79 (1H, m), 1.98-2.05 (2H, m), 2.10 (1H, dd, J=5, 10 Hz), 2.17 (1H, m), 2.42 (3H, s), 2.52 (1H, m), 2.87 (1H, m), 3.03 (1H, brd s), 3.29-3.51 (9H, m), 3.65 (2H, m), 3.80 (1H, m), 4.04 (1H, dd, J=5, 10 Hz), 4.21 (1H, m), 4.27 (1H, m), 4.38 (1H, m), 6.76 (1H, m), 6.90 (2H, m), 7.47 (1H, s), 7.52 (1H, s), 7.58 MS (ESI) (M+H)$^+$ 574.38.

Step 9 (B): $N^1$-butyl-$N^3$-((1R,2S)-3-(3,5-difluorophenyl)-1-hydroxy-1-((2R,4R)-4-propoxypyrrolidin-2-yl)propan-2-yl)-$N^1$,5-dimethylisophthalamide. The solution of (2R,4R)-tert-butyl 2-((1S,2S)-2-(3-(benzamido)-5-methylbenzamido)-1-(tert-butyldimethylsilyloxy)-3-(3,5-difluorophenyl)propyl)-4-propoxypyrrolidine-1-carboxylate (Step 9 (A), 24 mg) in HCl (4.0 M solution in dioxane, 1 mL) was added 2 drops of $H_2O$ and the mixture was stirred at rt for 3 h. The solvent was removed and the mixture was purified by reverse phase HPLC (20×50 mm YMC ODS-A S5 column, 34-82% methanol/$H_2O$/0.1% TFA) to give 12 mg of the title compound: $^1$H NMR ($CD_3OD$, 500 MHz) δ ppm 0.77 (2H, m), 0.97 (3H, m), 1.03 (2H, m), 1.14 (1H, m), 1.44 (1H, dd, J=10, 15 Hz), 1.53 (1H, m), 1.59-1.71 (3H, m), 2.16 (1H, m), 2.42 (3H, s), 2.51 (1H, m), 2.87 (1H, m), 2.92 (1H, s), 3.08 (1H, s), 3.24 (1H, m), 3.35-3.50 (5H, m), 3.56 (1H, m), 3.80 (1H, m), 4.05 (1H, m), 4.20 (1H, m), 4.27 (1H, m), 6.75 (1H, t, J=10 Hz), 6.90 (2H, d, J=5 Hz), 7.37 (1H, s), 7.43 (1H, s), 7.57 (1H, d, J=10 Hz). MS (ESI) (M+H)$^+$ 546.41.

Example 9

$N^1$-butyl-$N^3$-((1R,2S)-3-(3,5-difluorophenyl)-1-hydroxy-1-((2R,4R)-4-propoxypyrrolidin-2-yl)propan-2-yl)-$N^1$,5-dimethylisophthalamide

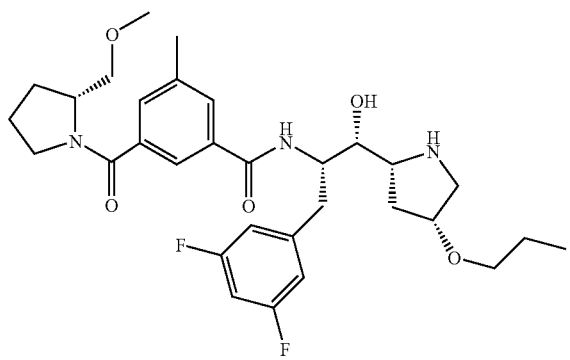

Step 9 (A): (2R,4R)-tert-butyl 2-((1S,2S)-2-(3-(benzamido)-5-methylbenzamido)-1-(tert-butyldimethylsilyloxy)-3-(3,5-difluorophenyl)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)-5-methylbenzoic acid (Preparation G, 26 mg, 0.037 mmol) in dichloromethane (1 mL) was added Hunig's base (15 mg, 0.114 mmol) to make a clear solution and HATU (19 mg, 0.05 mmol) was then added. After stirring for 20 min, the reaction mixture was added methylbutylamine (5 mg, 0.057 mmol) and the reaction mixture was stirred at rt for 6 h. The crude mixture was purified by silica gel Flash Chromatography (0% to 10% to 30% EtOAc/Hexane step gradient) to give 24 mg of the title compound (85% yield): $^1$H NMR ($CDCl_3$, 500 MHz) δ ppm 0.02 (3H, s), 0.06 (3H, s), 0.72-0.97 (15H, m), 1.12 (1H, m), 1.36-1.53 (11H, m), 1.61 (1H, m), 1.78 (2H, s), 2.05 (1H, m), 2.19 (1H, m), 2.38 (3H, s), 2.62 (1H, m), 2.91-2.95 (3H, m), 3.04 (1H, s), 3.21 (1H, m), 3.27-3.36 (3H, m), 3.50 (1H, m), 3.76 (1H, m), 3.98 (1H, m), 4.03-4.06 (1H, m), 4.10-4.12 (1H, m), 4.56 (1H, m), 6.59 (1H, m), 6.76 (2H, d, J=5 Hz), 7.29 (1H, d, J=10 Hz), 7.64 (1H, s), 7.71 (1H, s), 8.03 (1H, brd s). MS (ESI) (M+H)$^+$ 760.61.

Example 10

$N^1$-((1R,2S)-3-(3,5-difluorophenyl)-1-hydroxy-1-((2R,4R)-4-propoxypyrrolidin-2-yl)propan-2-yl)-5-methyl-$N^3$,$N^3$-dipropylisophthalamide

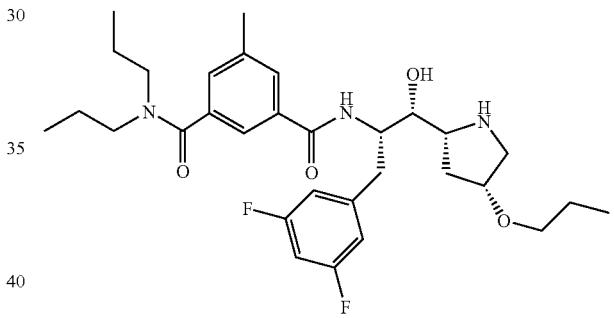

Step 10 (A): Preparation of (2R,4R)-tert-butyl 2-((1S,2S)-2-(3-(benzamido)-5-methylbenzamido)-1-(tert-butyldimethylsilyloxy)-3-(3,5-difluorophenyl)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)-5-methylbenzoic acid (Preparation G, 26 mg, 0.037 mmol) in dichloromethane (1 mL) was added Hunig's base (15 mg, 0.114 mmol) to make a clear solution and HATU (18 mg, 0.05 mmol) was then added. After stirring for 20 min, the reaction mixture was added dipropylamine (6 mg, 0.057 mmol) and the reaction mixture was stirred at rt for 6 h. The crude mixture was purified by silica gel Flash Chromatography (0% to 10% to 30% EtOAc/Hexane step gradient) to give 27 mg of the title compound (90% yield): $^1$H NMR ($CDCl_3$, 500 MHz) δ ppm 0.02 (3H, s), 0.06 (3H, s), 0.71 (3H, m), 0.85 (9H, s), 0.88 (3H, m), 0.96 (3H, m), 1.48-1.54 (12H, m), 1.67 (2H, m), 1.74 (2H, m), 2.03-2.09 (1H, m), 2.19 (1H, m), 2.38 (3H, s), 2.62 (1H, m), 2.94 (1H, m), 3.13 (2H, brd s), 3.26-3.36 (3H, m), 3.43 (2H, brd s), 3.76 (1H, m), 3.97 (1H, m), 4.04-4.07 (1H, m), 4.10-4.12 (1H, m), 4.58 (1H, m), 6.59 (1H, m), 6.76 (2H, d, J=5 Hz), 7.25 (1H, s), 7.60 (1H, s), 7.70 (1H, s), 7.98 (1H, brd s). MS (ESI) (M+H)$^+$ 774.63.

Step 10 (B): N¹-((1R,2S)-3-(3,5-difluorophenyl)-1-hydroxy-1-((2R,4R)-4-propoxypyrrolidin-2-yl)propan-2-yl)-5-methyl-N³,N³-dipropylisophthalamide. The solution of (2R,4R)-tert-butyl 2-((1S,2S)-2-(3-(benzamido)-5-methylbenzamido)-1-(tert-butyldimethylsilyloxy)-3-(3,5-difluorophenyl)propyl)-4-propoxypyrrolidine-1-carboxylate (Step 10 (A), 27 mg) in HCl (4.0 M solution in dioxane, 1 mL) was added 2 drops of H₂O and the mixture was stirred at rt for 3 h. The solvent was removed and the mixture was purified by reverse phase HPLC (20×50 mm YMC ODS-A S5 column, 34-82% methanol/H₂O/0.1% TFA) to give 11 mg of the title compound: $^1$H NMR (CD₃OD, 500 MHz) δ ppm 0.72 (3H, m), 0.97 (3H, m), 1.01 (3H, t, J=5 Hz), 1.52 (2H, dd, J=10, 15 Hz), 1.62 (2H, m), 1.72 (2H, dd, J=10, 15 Hz), 2.17 (1H, m), 2.42 (3H, s), 2.51 (1H, m), 2.87 (1H, m), 3.17 (2H, m), 3.35-3.50 (7H, m), 3.80 (1H, m), 4.06 (1H, dd, J=5, 10 Hz), 4.21 (1H, m), 4.27 (1H, m), 6.75 (1H, m), 6.90 (2H, m), 7.33 (1H, s), 7.39 (1H, s), 7.57 (1H, s). MS (ESI) (M+H)⁺ 560.43.

Example 11

N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-(oxazol-2-yl)benzamide

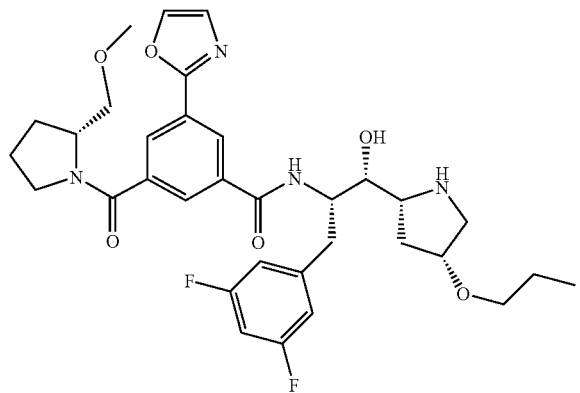

Step 11 (A): Preparation of (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)-5-(oxazol-2-yl)benzamido)propyl)-4-propoxypyrrolidine-1-carboxylate. To a solution of 3-((R)-2-(methoxymethyl)pyrrolidine-1-carbonyl)-5-(oxazol-2-yl)benzoic acid (Preparation H, 40 mg, 0.12 mmol) in dichloromethane (3 mL) was added Hunig's base (46 mg, 0.36 mmol) to make a clear solution and HATU (60 mg, 0.156 mmol) was then added. After stirring for 20 min, the reaction mixture was added (2R,4R)-tert-butyl 2-((1S,2S)-2-amino-1-(tert-butyldimethylsilyloxy)-3-(3,5-difluorophenyl)propyl)-4-propoxypyrrolidine-1-carboxylate (Step 1 (A), 64 mg, 0.12 mmol) and the reaction mixture was stirred at rt for 16 h. The crude mixture was purified by silica gel Flash Chromatography (0% to 30% to 50% to 70% EtOAc/Hexane step gradient) to give 70 mg of the title compound (70% yield): $^1$H NMR (CDCl₃, 500 MHz) δ ppm 0.02 (3H, s), 0.07 (3H, s), 0.84 (9H, s), 0.87 (3H, m), 1.46-1.50 (1H, m), 1.74 (1H, m), 1.92-2.06 (3H, m), 2.17-2.23 (2H, m), 2.66 (1H, m), 2.77-2.81 (2H, m), 2.92 (1H, m), 3.05 (1H, m), 3.29-3.38 (4H, m), 3.48 (1H, m), 3.58 (1H, m), 3.66 (1H, m), 3.76 (1H, m), 3.98 (1H, m), 4.07-4.09 (1H, m), 4.12-4.14 (1H, m), 4.43 (1H, brd s), 4.61 (1H, m), 6.58 (1H, m), 6.77 (2H, d, J=10 Hz), 7.22 (1H, s), 7.69 (1H, s), 8.10 (1H, s), 8.28 (1H, s), 8.53 (1H, brd s), 8.64 (1H, s). MS (ESI) (M+H)⁺ 841.61.

Step 11 (B): Preparation of N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-(oxazol-2-yl)benzamide. The solution of (2R,4R)-tert-butyl 2-((1S,2S)-1-(tert-butyldimethylsilyloxy)-3-(3,5-difluorophenyl)-2-(3-((R)-2-(methoxymethyl)pyrrolidine-1-carbonyl)-5-(oxazol-2-yl)benzamido)propyl)-4-propoxypyrrolidine-1-carboxylate (Step 11 (A),70 mg) in HCl (4.0 M solution in dioxane, 2 mL) was added 2 drops of H₂O and the mixture was stirred at rt for 2 h. The solvent was removed and the mixture was purified by reverse phase HPLC (30×50 mm YMC ODS-A S5 column, 34-82% methanol/H₂O/0.1% TFA) to give 40 mg of the title compound: $^1$H NMR (CD₃OD, 500 MHz) δ ppm 0.97 (3H, m), 1.63 (2H, m), 1.82 (1H, m), 2.03 (2H, m), 2.12 (1H, m), 2.19 (1H, m), 2.54 (1H, m), 2.89 (1H, m), 3.03 (1H, m), 3.36-3.53 (9H, m), 3.68 (2H, m), 3.87 (1H, m), 4.08 (1H, dd, J=5, 10 Hz), 4.25-4.30 (2H, m), 4.42 (1H, m), 6.75 (1H, m), 6.92 (2H, m), 7.37 (1H, s), 7.85 (1H, s), 8.05 (1H, s), 8.26 (1H, s), 8.39 (1H, m). MS (ESI) (M+H)⁺ 627.41.

Example 12

N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-(oxazol-2-yl)benzamide

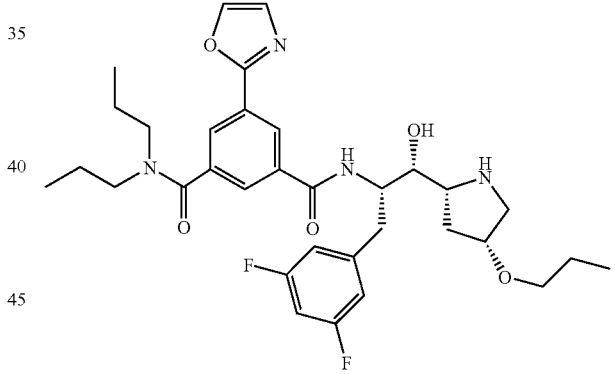

Step 12 (A): Preparation of (2R,4R)-tert-butyl 2-((1S,2S)-2-(3-(benzamido)-5-(oxazol-2-yl)benzamido)-1-(tert-butyldimethylsilyloxy)-3-(3,5-difluorophenyl)propyl)-4-propoxypyrrolidine-1-carboxylate. To a solution of 3-(dipropylcarbamoyl)-5-(oxazol-2-yl)benzoic acid (WO 2002/02512), 45 mg, 0.14 mmol) in dichloromethane (2 mL) was added Hunig's base (54 mg, 0.42 mmol) to make a clear solution and HATU (65 mg, 0.17 mmol) was then added. After stirring for 30 min, the reaction mixture was added (2R,4R)-tert-butyl 2-((1S,2S)-2-amino-1-(tert-butyldimethylsilyloxy)-3-(3,5-difluorophenyl)propyl)-4-propoxypyrrolidine-1-carboxylate (Step 1 (A), 81 mg, 0.154 mmol) and the reaction mixture was stirred at rt for 6 h. The crude mixture was purified by silica gel Flash Chromatography (0% to 10% to 20% to 30% to 40% EtOAc/Hexane step gradient) to give 110 mg of the title compound (95% yield): $^1$H NMR (CDCl₃, 500 MHz) δ ppm 0.03 (3H, s), 0.06 (3H, s), 0.69 (3H, m), 0.82 (9H, s), 0.87 (3H, m), 0.96 (3H, m), 1.21-1.28 (2H, m), 1.47-1.51 (11H, 1.68 (2H, m), 2.01 (1H, m), 2.18 (1H, d, J=15 Hz), 2.68 (1H, dd, J=10, 15 Hz), 2.88 (1H, dd, J=5, 15 Hz), 3.14 (2H, m), 3.26-3.36 (3H, m), 3.44 (2H, m), 3.74 (1H, dd, J=5, 10 Hz), 3.98 (1H, m), 4.08-4.11 (2H, m), 4.64 (1H, dd, J=10, 15 Hz), 6.59 (1H, m), 6.78 (2H, d, J=5 Hz), 7.22 (1H, s), 7.68 (1H, s), 7.97 (1H, s), 8.14 (1H, s), 8.64 (2H, m).

Step 12 (B): Preparation of $N^1$-((1R,2S)-3-(3,5-difluorophenyl)-1-hydroxy-1-((2R,4R)-4-propoxypyrrolidin-2-yl)propan-2-yl)-5-(oxazol-2-yl)-$N^3$,$N^3$-dipropylisophthalamide. The solution of (2R,4R)-tert-butyl 2-((1S,2S)-2-(3-(benzamido)-5-(oxazol-2-yl)benzamido)-1-(tert-butyldimethylsilyloxy)-3-(3,5-difluorophenyl)propyl)-4-propoxypyrrolidine-1-carboxylate (step 12 (A), 110 mg) in HCl (4.0 M solution in dioxane, 2 mL) was added 4 drops of $H_2O$ and the mixture was stirred at rt for 2 h. The solvent was removed and the mixture was purified by reverse phase HPLC (30×100 mm PHENOMENEX-LUNA S10 column, 42-82% methanol/$H_2O$/0.1% TFA) to give the title compound: $^1$H NMR ($CD_3OD$, 500 MHz) δ ppm 0.74 (3H, m), 0.97 (3H, m), 1.03 (3H, m), 1.57 (1H, dd, J=5, 15 Hz), 1.63 (1H, m), 1.76 (2H, dd, J=5, 15 Hz), 2.19 (1H, m), 2.54 (1H, m), 2.90 (1H, dd, J=10, 15 Hz), 3.21 (2H, m), 3.35-3.53 (7H, m), 3.85 (1H, m), 4.08 (1H, dd, J=5, 10 Hz), 4.23-4.30 (2H, m), 6.75 (1H, m), 6.92 (2H, m), 7.37 (1H, s), 7.71 (1H, m), 8.06 (1H, s), 8.13 (1H, m), 8.39 (1H, m). MS (ESI) (M+H)$^+$ 613.27.

Example 13

N-((1R,2S)-3-(3,5-difluorophenyl)-1-hydroxy-1-((2R,4R)-4-propoxypyrrolidin-2-yl)propan-2-yl)-3-methoxy-5-(2-oxopyrrolidin-1-yl)benzamide

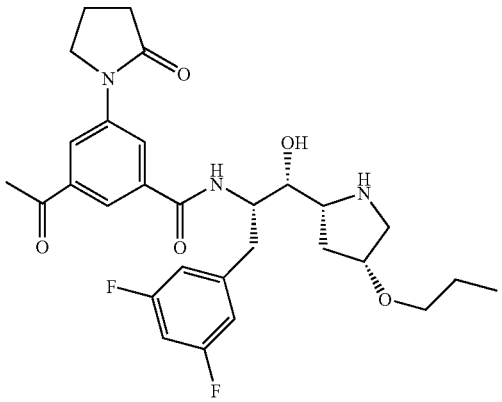

Step 13 (A): (2R,4R)-tert-Butyl 2-((1S,2S)-1-(tert-butyldimethylsilyloxy)-3-(3,5-difluorophenyl)-2-(3-methoxy-5-(2-oxopyrrolidin-1-yl)benzamido)propyl)-4-propoxypyrrolidine-1-carboxylate. To a solution of (2R,4R)-tert-butyl 2-((1S,2S)-1-(tert-butyldimethylsilyloxy)-3-(3,5-difluorophenyl)-2-(3-hydroxy-5-(2-oxopyrrolidin-1-yl)benzamido)propyl)-4-propoxypyrrolidine-1-carboxylate (Preparation I, 27 mg, 0.037 mmol) in DMF (1 mL) were added cesium carbonate (24 mg, 0.074 mmol) and methyl iodide (25 mg, 0.185 mmol) and the reaction mixture was stirred at 80° C. for 3 h, at rt for 3 days and microwaved at 80° C. for 6 h. Ethyl acetate (100 mL) was added and the mixture was washed with $H_2O$ and concentrated under vacuum. The crude mixture was purified by silica gel Flash Chromatography (0% to 20% to 40% to 60% EtOAc/Hexane step gradient) to give 20 mg of the title compound: $^1$H NMR ($CDCl_3$, 500 MHz) δ ppm 0.02 (3H, s), 0.07 (3H, s), 0.85 (9H, s), 0.88 (3H, m), 1.46-1.54 (11H, m), 2.02-2.07 (1H, m), 2.10-2.16 (2H, m), 2.20 (1H, m), 2.59 (2H, m), 2.64 (1H, dd, J=10, 15 Hz), 2.92 (1H, m), 3.28-3.37 (3H, m), 3.76 (1H, dd, J=5, 10 Hz), 3.84 (3H, s), 3.88-3.92 (2H, m), 3.98 (1H, m), 4.04-4.13 (2H, m), 4.58 (1H, m), 6.60 (1H, m), 6.78 (2H, d, J=5 Hz), 7.23 (1H, s), 7.34 (1H, s), 7.80 (1H, s), 8.05 (1H, brd s). MS (ESI) (M+H)$^+$ 746.41.

Step 13 (B): N-((1R,2S)-3-(3,5-Difluorophenyl)-1-hydroxy-1-((2R,4R)-4-propoxypyrrolidin-2-yl)propan-2-yl)-3-methoxy-5-(2-oxopyrrolidin-1-yl)benzamide. The solution of (2R,4R)-tert-butyl 2-((1S,2S)-1-(tert-butyldimethylsilyloxy)-3-(3,5-difluorophenyl)-2-(3-methoxy-5-(2-oxopyrrolidin-1-yl)benzamido)propyl)-4-propoxypyrrolidine-1-carboxylate (Step 13 (A), 20 mg) in HCl (4.0 M solution in dioxane, 1 mL) was added 2 drops of $H_2O$ and the mixture was stirred at rt for 1 h. The solvent was removed and the mixture was purified by reverse phase HPLC (30×100 mm PHENOMENEX-LUNA S10 column, 34-82% methanol/$H_2O$/0.1% TFA) to give 5 mg of the title compound: $^1$H NMR ($CD_3OD$, 500 MHz) δ ppm 0.97 (3H, m), 1.63 (2H, m), 2.20 (3H, m), 2.53 (1H, m), 2.63 (2H, m), 2.87 (1H, m), 3.35-3.51 (5H, m), 3.80 (1H, m), 3.83 (3H, s), 3.92 (2H, m), 4.04 (1H, m), 4.18 (1H, m), 4.28 (1H, m), 6.77 (1H, m), 6.90 (2H, m), 6.99 (1H, m), 7.39 (1H, m), 7.41 (1H, m). MS (ESI) (M+H)$^+$ 532.34.

Example 14

N-((1R,2S)-3-(3,5-difluorophenyl)-1-hydroxy-1-((2R,4R)-4-propoxypyrrolidin-2-yl)propan-2-yl)-3-isopropoxy-5-(2-oxopyrrolidin-1-yl)benzamide

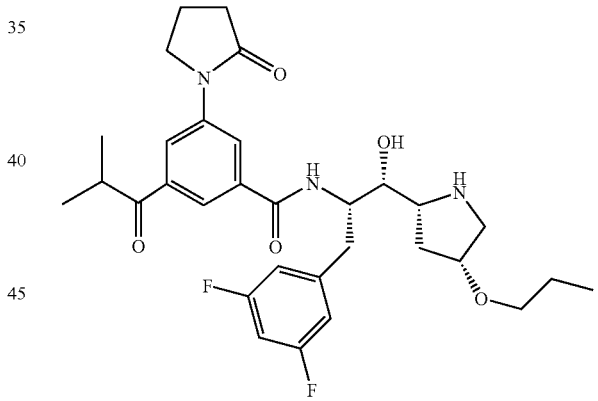

Step 14 (A): (2R,4R)-tert-butyl 2-((1S,2S)-1-(tert-butyldimethylsilyloxy)-3-(3,5-difluorophenyl)-2-(3-isopropoxy-5-(2-oxopyrrolidin-1-yl)benzamido) propyl)-4-propoxypyrrolidine-1-carboxylate. To a solution of (2R,4R)-tert-butyl 2-((1S,2S)-1-(tert-butyldimethylsilyloxy)-3-(3,5-difluorophenyl)-2-(3-hydroxy-5-(2-oxopyrrolidin-1-yl)benzamido)propyl)-4-propoxypyrrolidine-1-carboxylate (Preparation I, 38 mg, 0.05 mmol) in DMF (1 mL) were added cesium carbonate (29 mg, 0.09 mmol) and 2-iodopropane (42 mg, 0.25 mmol) and the reaction mixture was microwaved at 60° C. for 2 h. Ethyl acetate (100 mL) was added and the mixture was washed with Brine, $H_2O$ and concentrated under vacuum. The crude mixture was purified by silica gel Flash Chromatography (0% to 20% to 30% to 40% EtOAc/Hexane step gradient) to give 21 mg of the title compound: $^1$H NMR ($CDCl_3$, 500 MHz) δ ppm 0.01 (3H, s), 0.07 (3H, s), 0.86 (9H, s), 0.88 (3H, m), 1.32 (6H, d, J=5 Hz), 1.46-1.54 (11H, m), 2.03-2.21 (4H, m), 2.59 (2H, m), 2.62 (1H, dd, J=10, 15 Hz), 2.94 (1H, m), 3.26-3.36 (3H, m), 3.76 (1H, dd, J=5, 10 Hz), 3.84-3.91 (2H, m), 3.97 (1H, m), 4.04-4.07 (1H, m), 4.11-4.13 (1H, m), 4.55 (1H, m), 4.63 (1H, m), 6.59 (1H, m), 6.78 (2H, d, J=5 Hz), 7.20 (1H, s), 7.33 (1H, s), 7.71 (1H, s), 7.99 (1H, d, J=10 Hz). MS (ESI) (M+H)+ 775.45.

Step 14 (B): N-((1R,2S)-3-(3,5-difluorophenyl)-1-hydroxy-1-((2R,4R)-4-propoxypyrrolidin-2-yl)propan-2-yl)-3-isopropoxy-5-(2-oxopyrrolidin-1-yl)benzamide. The solution of (2R,4R)-tert-butyl 2-((1S,2S)-1-(tert-butyldimethylsilyloxy)-3-(3,5-difluorophenyl)-2-(3-isopropoxy-5-(2-oxopyrrolidin-1-yl)benzamido)propyl)-4-propoxypyrrolidine-1-carboxylate (Step 14 (A), 21 mg) in HCl (4.0 M solution in dioxane, 1 mL) was added 2 drops of H₂O and the mixture was stirred at rt for 2 h. The solvent was removed and the mixture was purified by reverse phase HPLC (21.2×50 mm PHENOMENEX-LUNA S10 column, 34-82% methanol/H₂O/0.1% TFA) to give 11 mg of the title compound: ¹H NMR (CD₃OD, 500 MHz) δ ppm 0.97 (3H, m), 1.32 (6H, m), 1.63 (2H, m), 2.14-2.22 (3H, m), 2.52 (1H, m), 2.62 (2H, t, J=10 Hz), 2.86 (1H, dd, J=10, 15 Hz), 3.35-3.51 (5H, m), 3.80 (1H, m), 3.91 (2H, m), 4.04 (1H, m), 4.16-4.22 (1H, m), 4.27 (1H, m), 4.62 (1H, m), 6.77 (1H, m), 6.90 (2H, m), 6.96 (1H, m), 7.35 (1H, m), 7.40 (1H, m). MS (ESI) (M+H)+ 560.30.

Example 15

N¹-((1R,2S)-3-(3,5-difluorophenyl)-1-hydroxy-1-((2R,4R)-4-propoxypyrrolidin-2-yl)propan-2-yl)-N³-(1-phenylethyl)isophthalamide

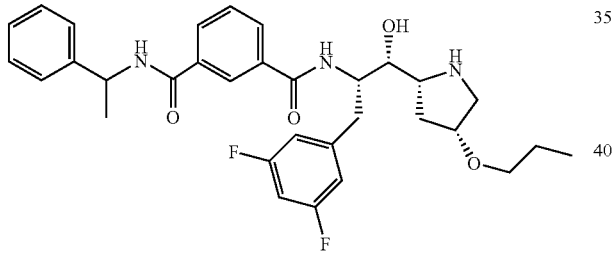

Step 15 (A): (2R,4R)-tert-Butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid (Step 1 (C), 40 mg, 0.06 mmol) in dichloromethane (1.5 mL) was added Hunig's base (24 mg, 0.18 mmol) to make a clear solution and HATU (28 mg, 0.072 mmol) was then added. After stirring for 20 min, the reaction mixture was added 1-phenylethanamine (15 mg, 0.12 mmol) and the reaction mixture was stirred at rt overnight. The reaction mixture was concentrated under vacuum and purified by silica gel Flash Chromatography (0% to 15% to 30% EtOAc/Hexane step gradient) to give 40 mg of the title compound (87% yield): ¹H NMR (CDCl₃, 500 MHz) δ 0.01 (3H, s), 0.05 (3H, s), 0.85 (9H, s), 0.89 (3H, m), 1.46 (9H, s), 1.50 (2H, m), 1.58 (3H, d, J=5 Hz), 2.02-2.05 (1H, m), 2.20 (1H, dd, J=5, 10 Hz), 2.64 (1H, m), 2.88-2.94 (1H, m), 3.30-3.37 (3H, m), 3.78 (1H, dd, J=5, 15 Hz), 4.00 (1H, m), 4.07-4.13 (2H, m), 4.60 (1H, m), 5.33 (1H, m), 6.56-6.61 (2H, m), 6.77 (2H, d, J=10 Hz), 7.25 (1H, m), 7.32 (2H, m), 7.37 (2H, m), 7.48 (1H, m), 7.97-8.01 (2H, m), 8.20 (1H, m), 8.24-8.31 (1H, m). MS (ESI) (M+H)+ 780.49.

Step 15 (B): Preparation of N¹-((1R,2S)-3-(3,5-difluorophenyl)-1-hydroxy-1-((2R,4R)-4-propoxypyrrolidin-2-yl)propan-2-yl)-N³-(1-phenylethyl)isophthalamide. The solution of (2R,4R)-tert-butyl 2-((1S,2S)-1-(tert-butyldimethylsilyloxy)-2-(3-(carbamoyl)benzamido)-3-(3,5-difluorophenyl)propyl)-4-propoxypyrrolidine-1-carboxylate (Step 15 (A), 40 mg) in HCl (4.0 M solution in dioxane, 1 mL) was added 2 drops of H₂O and the mixture was stirred at rt for 1 h. The solvent was removed and the mixture was purified by reverse phase HPLC (30×100 mm PHENOMENEX-LUNA S5 column, 50-82% methanol/H₂O/0.1% TFA) to give 30 mg of the title compound: ¹H NMR (CD₃OD, 500 MHz) δ ppm 0.97 (3H, m), 1.58 (3H, d, J=5 Hz), 1.62 (2H, m), 2.16 (1H, m), 2.50 (1H, m), 2.86 (1H, m), 3.34-3.49 (5H, m), 3.81 (1H, m), 4.06 (1H, dd, J=5, 10 Hz), 4.21-4.25 (2H, m), 5.22-5.28 (1H, m), 6.73 (1H, m), 6.89-6.90 (2H, m), 7.25 (1H, m), 7.34 (2H, m), 7.41 (2H, d, J=10 Hz), 7.53 (1H, t, J=10 Hz), 7.79-7.81 (1H, m), 7.97 (1H, d, J=10 Hz), 8.12-8.13 (1H, m). MS (ESI) (M+H)+ 566.29.

Example 16

N¹-((1R,2S)-3-(3,5-difluorophenyl)-1-hydroxy-1-((2R,4R)-4-propoxypyrrolidin-2-yl)propan-2-yl)-N³-(1-(4-fluorophenyl)ethyl)isophthalamide

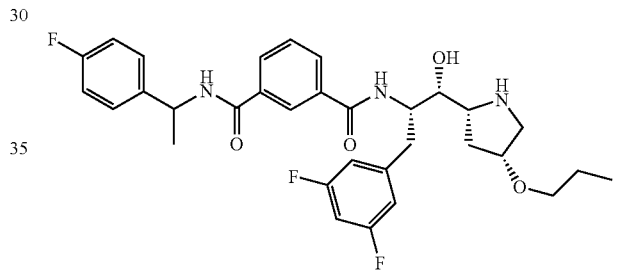

Step 16 (A): (2R,4R)-tert-Butyl 2-((1S,2S)-1-(tert-butyldimethylsilyloxy)-2-(3-(carbamoyl)benzamido)-3-(3,5-difluorophenyl) propyl)-4-propoxypyrrolidine-1-carboxylate. To a solution of 3-(((1S,2S)-1-((2R,4R)-1-(tert-butoxycarbonyl)-4-propoxypyrrolidin-2-yl)-1-(tert-butyldimethylsilyloxy)-3-(3,5-difluorophenyl)propan-2-yl)carbamoyl)benzoic acid (Step 1 (C), 40 mg, 0.06 mmol) in dichloromethane (1.5 mL) was added Hunig's base (24 mg, 0.18 mmol) to make a clear solution and HATU (28 mg, 0.072 mmol) was then added. After stirring for 20 min, the reaction mixture was added 1-(4-fluorophenyl)ethanamine (17 mg, 0.12 mmol) and the reaction mixture was stirred at rt overnight. The reaction mixture was concentrated under vacuum and purified by silica gel Flash Chromatography (0% to 15% to 30% EtOAc/Hexane step gradient) to give 38 mg of the title compound (84% yield): ¹H NMR (CDCl₃, 500 MHz) δ 0.02 (3H, s), 0.05 (3H, s), 0.84 (9H, s), 0.89 (3H, m), 1.47 (9H, s), 1.50 (2H, m), 1.58 (3H, d, J=5 Hz), 2.00-2.05 (1H, m), 2.22 (1H, m), 2.64 (1H, m), 2.86-2.92 (1H, m), 3.28-3.37 (3H, m), 3.76 (1H, m), 4.00 (1H, m), 4.07-4.12 (2H, m), 4.61 (1H, m), 5.31 (1H, m), 6.51-6.52 (1H, m), 6.60 (1H, m), 6.77 (2H, d, J=10 Hz), 7.00 (2H, m), 7.34 (2H, dd, J=5, 10 Hz), 7.49 (1H, m), 7.99-8.02 (2H, m), 8.20 (1H, s), 8.33 (1H, m). MS (ESI) (M+H)+ 798.46.

Step 16 (B): N¹-((1R,2 S)-3-(3,5-Difluorophenyl)-1-hydroxy-1-((2R,4R)-4-propoxypyrrolidin-2-yl)propran-2-yl)-

N³-(1-(4-fluorophenyl)ethyl)isophthalamide. The solution of (2R,4R)-tert-butyl 2-((1S,2S)-1-(tert-butyldimethylsilyloxy)-2-(3-(carbonyl)benzamido)-3-(3,5-difluorophenyl)propyl)-4-propoxypyrrolidine-1-carboxylate (Step 16 (A), 38 mg) in HCl (4.0 M solution in dioxane, 1 mL) was added 2 drops of H₂O and the mixture was stirred at rt for 1 h. The solvent was removed and the mixture was purified by reverse phase HPLC (30×100 mm PHENOMENEX-LUNA S5 column, 34-90% methanol/H₂O/0.1% TFA) to give 30 mg of the title compound: ¹H NMR (CD₃OD, 500 MHz) δ ppm 0.97 (3H, m), 1.58 (3H, d, J=5 Hz), 1.62 (2H, m), 2.17 (1H, m), 2.50 (1H, m), 2.86 (1H, m), 3.34-3.49 (5H, m), 3.81 (1H, m), 4.06 (1H, dd, J=5, 10 Hz), 4.22-4.25 (2H, m), 5.21-5.27 (1H, m), 6.73 (1H, m), 6.89-6.90 (2H, m), 7.07 (2H, m), 7.41-7.44 (2H, m), 7.53 (1H, t, J=10 Hz), 7.79-7.82 (1H, m), 7.96 (1H, m), 8.12-8.14 (1H, m), MS (ESI) (M+H)⁺ 584.32.

Example 17

N¹-((1R,2S)-1-hydroxy-3-phenyl-1-((2R,4R)-4-(propylsulfonyl)pyrrolidin-2-yl)propan-2-yl)-5-(oxazol-2-yl)-N³,N³-dipropylisophthalamide

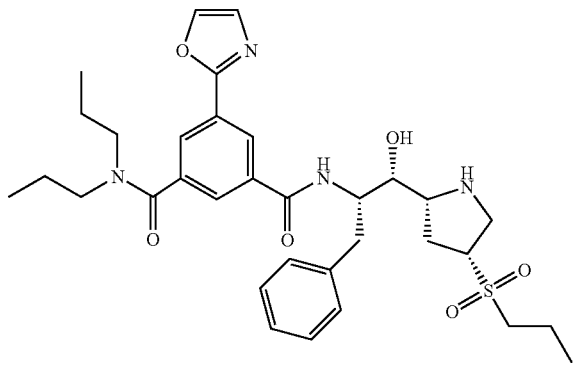

Step 17 (A): (2R,4R)-tert-butyl 2-(1S,2S)-2-(benzylcarbonyl)-1-(tert-butyldimethylsilyloxy)-3-phenylpropyl)-4-hydroxypyrrolidine-1-carboxylate. A solution of the compound of Preparation J (230 mg, 0.37 mmol) dissolved in a mixture of 3 mL of ethanol and 0.5 mL of water was treated with Wilkinsin's catalyst (28 mg, 8% by weight). The resulting was heated to 95° C. for 16 h, then allowed to cool to rt. A solution of KMnO₄ (117 mg, 0.74 mmol) dissolved in 0.4 mL of water was then added, followed by methanol until the solution became homogeneous, and the resulting reaction solution was stirred rt for 16 h. The reaction solution was then partitioned between ethyl acetate and water and the organic layer was separated, dried, and concentrated to a crude product which was purified using column chromatography to provide 110 mg of the desired alcohol (51%). ¹H NMR (500 MHz, CDCl₃) δ ppm 0.12 (m, 6H) 0.95 (s, 9H), 1.47 (s, 9H), 2.16 (s, 2H), 2.38 (t, J=11.90 Hz, 1H), 3.27 (d, J=10.68 Hz, 2H) 3.50 (d, J=6.71 Hz, 1H) 3.61 (s, 1H) 3.77 (s, 1H) 3.94 (d, J=11.60 Hz, 1H) 4.20 (s, 2H), 4.37 (dd, J=7.32, 2.14 Hz, 1H) 4.82 (s, 1H) 4.94 (d, J=8.85 Hz, 1H) 7.21 (m, 10H). MS (ESI) (M+H−Boc)⁺=485.23.

Step 17 (B): (2R,4S)-tert-butyl 2-((1S,2S)-2-(benzyloxycarbonyl)-1-(tert-butyldimethylsilyloxy)-3-phenylpropyl)-4-(methylsulfonyloxy)pyrrolidine-1-carboxylate. A solution 126 mg of triphenylphosphine (0.48 mmol) in THF (3 mL) was treated with 84 mm (0.48 mmol) of a 40% solution of DEAD in toluene. After stirring for 5 min, 43 mg of methanesulfonic acid was added. After another 5 min, a solution of the compound of Step 17 (A) (90 mg, 0.16 mmol) dissolved in an additional 3 mL of THF was added, followed by DIPEA (124 mg, 0.96 mmol). The reaction solution was stirred at rt for 30 min, then heated to 60° C. for 4.5 hr. The cooled reaction solution was partitioned between ethyl acetate and water, the organic layer was concentrated, and the crude product was purified by chromatography eluting with a gradient of 5 to 20% ethyl acetate in hexanes to provide 100 mg (94%) of the desired mesylate. ¹H NMR (500 MHz, CDCl₃) δ ppm 0.02 (s, 3H) 0.11 (s, 3H) 0.92 (s, 9H) 1.48 (s, 9H) 2.30 (m, 2H) 2.46 (d, J=6.10 Hz, 1H) 2.92 (m, 2H) 3.28 (d, J=13.12 Hz, 1H) 3.41 (d, J=12.21 Hz, 1 H) 3.89 (d, J=12.82 Hz, 1H) 4.18 (m, 1H) 4.30 (m, 3H) 4.66 (d, J=9.16 Hz, 1 H) 4.82 (d, J=12.21 Hz, 1H) 4.94 (d, J=9.16 Hz, 1H) 5.16 (s, 1H) 7.19 (m, 10 H). MS (ESI) (M+H−Boc)⁺=563.24.

Step 17 (C): (2R,4R)-tert-butyl 2-((1S,2S)-2-(benzyloxycarbonyl)-1-(tert-butyldimethylsilyloxy)-3-phenylpropyl)-4-(propylthio)pyrrolidine-1-carboxylate. A solution of 4 mmol of propanethiol and 4 mmol (160 mg) of a 60% dispersion of sodium hydride in mineral oil were dissolved in 4 mL of DMF, and the solution was allowed to stir until the production of hydrogen gas ceased. A solution of the compound of step 17 (B) (200 mg, 0.30 mmol) dissolved in 3 mL of DMF was then treated with 1.5 mL of the above solution of thiolate anion and the reaction solution was stirred rt for 16 h. The reaction solution was partitioned between ethyl acetate and water, the organic layer was concentrated, and the crude product was purified by chromatography eluting with a gradient of 5 to 20% ethyl acetate in hexanes to provide 130 mg (67%) of the desired thiol and 27 mg (16%) of the corresponding elimination product. ¹H NMR (500 MHz, CDCl₃) δ ppm 0.06 (d, J=29.91 Hz, 6H) 0.94 (s, 9H) 0.98 (t, J=7.17 Hz, 3H) 1.47 (s, 9H) 1.60 (td, J=14.57, 7.17 Hz, 2H) 1.69 (s, 1H) 2.13 (2.28 (m, 1H) 2.38 (s, 1H) 2.52 (s, 2H) 2.95 (m, 2H) 3.22 (dd, J=43.49, 12.97 Hz, 1H) 3.91 (m, 1H) 4.10 (m, 1H) 4.24 (d, J=7.32 Hz, 1H) 4.77 (m, 1H) 4.95 (m, 1H) 7.19 (m, 10H). MS (ESI) (M+H)⁺=643.35

Step 17 (D): (2R,4R)-tert-butyl 2-((1S,2S)-2-(benzyloxycarbonyl)-1-(tert-butyldimethylsilyloxy)-3-phenylpropyl)-4-(propylsulfonyl)pyrrolidine-1-carboxylate. A solution of 130 mg (0.2 mmol) of the compound of step 17 (C) dissolved in 2 mL of methanol was treated with a solution of 240 mg (0.4 mmol) of ozone dissolved in 0.4 mL of water. After stirring at rt from 30 min, the reaction solution was partitioned between ethyl acetate and water, the organic layer was concentrated, and the crude product was purified by chromatography with a gradient of 20 to 80% ethyl acetate in hexanes to provide 86 mg (64%) of the desired sulfone and 37 mg (28%) of the sulfoxide intermediate as a lower-eluting compound. ¹H NMR (500 MHz, CDCl₃) δ ppm 0.06 (s, 3H) 0.11 (s, 3H) 0.96 (s, 9H) 1.07 (t, J=7.32 Hz, 3H) 1.47 (s, 9H) 1.87 (dd, J=13.43, 6.71 Hz, 3H) 2.03 (s, 1H) 2.26 (t, J=12.21 Hz, 1H) 2.38 (s, 1H) 2.68 (s, 1H) 2.90 (s, 2H) 3.46 (m, 2H) 3.75 (s, 1H) 4.09 (m, 2H) 4.26 (d, J=7.02 Hz, 1H) 4.77 (m, 1H) 4.95 (m, 1H) 7.18 (m, 10H) MS (ESI) (M+H−Boc)⁺=575.25

Step 17 (E): (2R,4R)-tert-butyl 2-((1S,2S)-2-amino-1-tert-butyldimethylsilyloxy)-3-phenylpropyl)-4-(propylsulfonyl)pyrrolidine-1-carboxylate. A 30 mg portion of 10% palladium on carbon was solvated with 5 mL of MeOH and then 86 mg (0.13 mmol) of the compound of step 17 (D) was added. The reaction mixture was placed under 50 psi of hydrogen gas in a Parr apparatus and shaken for 3 h. The catalyst was removed by filtration through a glass fiber to provide the amine (68 mg, 99%). ¹H NMR (500 MHz, CDCl₃) δ ppm 0.06 (m, 6H) 0.93 (s, 9H) 1.08 (t, J=7.02 Hz, 3H) 1.47 (s, 9H) 1.90

(d, J=7.32 Hz, 2H) 2.27 (m, 1H) 2.35 (dd, J=12.82, 6.71 Hz, 1H) 2.74 (s, 1H) 2.90 (m, 3H) 2.98 (ddd, J=10.68, 5.49, 2.44 Hz, 1H) 3.13 (d, J=12.21 Hz, 1H) 3.46 (d, J=8.24 Hz, 2H) 4.00 (s, 1H) 4.19 (d, J=2.14 Hz, 1H) 4.30 (s, 1H) 4.38 (s, 1 H) 7.22 (m, 5H). MS (ESI) (M+H)$^+$=541.32

Step 17 (F): (2R,4R)-tert-butyl 2-((1S,2S)-2-(3-(benzamido)-5-(oxazol-2-yl)benzamido)-1-(tert-butyldimethylsilyloxy)-3-phenylpropyl)-4-(propylsulfonyl)pyrrolidine-1-carboxylate. To a solution of 3-(dipropylcarbamoyl)-5-(oxazol-2-yl)benzoic acid (prepared as reported in WO 2002/02512, 20 mg, 0.062 mmol) in DCM is added HATU (28 mg, 0.073 mmol) and DIEA (33 mg, 0.26 mmol). After the solution is stirred at rt for 5 min, a 28 mg portion of the compounds of step 17 (E) (0.052 mmol) is added. The reaction solution was stirred 16 h at rt, and then the reaction solution was partitioned between ethyl acetate and water, the organic layer was concentrated, and the crude product was purified by chromatography eluting with a step gradient of 20% to 50% to 70% ethyl acetate in hexanes to provide 40 mg (98%) of the desired amide. MS (ESI) (M+H−Boc)$^+$=739.34

Step 17 (G): $N^1$-((1R,2S)-1-hydroxy-3-phenyl-1-((2R,4R)-4-(propylsulfonyl)pyrrolidin-2-yl)propan-2-yl)-5-(oxazol-2-yl)-$N^3$,$N^3$-dipropylisophthalamide. A 40 mg (0.48 mmol) portion of the compound of step 17 (F) was dissolved in 1 mL of 4 M HCl in dioxane, and 100 µL of water was added. After stirring at rt for 3 h. the solvents were removed and the crude product was purified by prep HLPC under standard conditions to provide 25 mg of the desired product as the TFA salt (84%). $^1$H NMR (500 MHz, CDCL$_3$) δ ppm 0.74 (t, J=7.02 Hz, 3H) 1.04 (t, J=7.02 Hz, 3H) 1.13 (t, J=7.48 Hz, 3H) 1.39 (m, 1H) 1.56 (m, 2H) 1.76 (m, 2H) 1.90 (td, J=15.26, 7.32 Hz, 2H) 2.61 (m, 1H) 2.73 (m, 1H) 2.85 (dd, J=13.73, 11.29 Hz, 1H) 3.19 (m, 4H) 3.46 (dd, J=13.89, 3.20 Hz, 1H) 3.52 (t, J=7.02 Hz, 2H) 3.72 (m, 1H) 3.80 (m, 1H) 3.99 (ddd, J=11.60, 6.41, 2.44 Hz, 1H) 4.15 (m, 2H) 4.25 (m, 1H) 7.16 (t, J=7.32 Hz, 1H) 7.25 (t, J=7.63 Hz, 2H) 7.30 m, 2H) 7.37 (d, J=0.61 Hz, 1H) 7.63 (t, J=1.53 Hz, 1H) 8.06 (s, 1H) 8.11 (t, J=1.53 Hz, 1H) 8.36 (t, J=1.53 Hz, 1H) MS (ESI) (M+H)$^+$=625.70.

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5; U.S. Pat. Nos. 6,410,266 and 6,361,972). T225 flask culture of HEK293-9B.A1 were grown to 80% confluency in DMEM supplemented with 2 mM L-glutamine, 10 µg/ml penicillin, 10 µg/ml streptomycin, 3 µg/ml puromycin, 100 nM methotrexate, and 10% fetal bovine serum (invitrogen, Carlsbad, Calif.), harvested, and resuspended at 2×10$^8$ cells per 10 ml of lysis buffer consisting of 50 mM HEPES pH7.0 containing a protease inhibitor cocktail of AEBSF 104 µM, aprotinin 80 nM, leupeptin 2 µM, bestatin 4 µM, pepstatin A 1.5 µM, and E-64 1.4 µM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein connection of 5 mg/ml, then aliquots were frozen in liquid nitrogen for further storage at −70° C. Immediately before carrying out a binding assay, and aliquot of cell homogenate was thawed and diluted to a concentration of 100 µg/ml in assay buffer consisting of 50 mM HEPES pH 5.0 and 0.1% CHAPSO. Assays were initiated in polypropylene 96-well plates (Costar, Cambridge, Mass.) by the addition of 200 µl of cell homogenate to 50 µl of assay buffer containing 1 nM radioligand (WO 2004 013098, compound 3, where the methoxy group is substituted for C($^3$H)$_3$:80 Ci/mMol) various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using Wallac 1450 Microbeta liquid scintillation counter (PerkinElmer, Boston, Mass.). Ki values of competing compounds were derived through Cheng-Prussoff correction of IC50 values calculated using XLfit (IDBS, Guildford, UK).

Abbreviations:

AEBSF: 4-(2-Aminoethyl)benzensulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

Activity of example compounds of the invention is provided in Table 1, wherein +++ denotes activity of 0.1 μM or greater potency, and ++ denotes potency in the range of 0.1 to 1.0 μM.

TABLE 1

| Compound of Example | Activity Rating[a] |
|---|---|
| 7 | ++ |
| 11 | +++ |
| 12 | +++ |
| 17 | +++ |

[a]Activity based on $IC_{50}$ values:
+++ = <0.1 μM
++ = 0.1-1.0 μM

In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A; Lewis, M; Smith, D. W.; Pak, R. PCT Publication WO 01/0175435; Fechteler, K; Kostka, M; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; T. S. et al., *Proc. Natl. Acad. Sci. USA*, 1996, 93, 13170-13175), western blot (Klafki, H.-W.; Ambramowski, D. et al., *J. Biol. Chem.*, 1996, 271, 28655-28659), enzyme linked immunosorbent assay (ELISA) as demonstrated by Seubert, P.; Vigo-Pelfry, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A; Lewis, M.; Smith, D. W.; Pak, R. PCT Publication WO 01/0175435; Shearman, M.; Beher, D. et al., *Biochemistry*, 2000, 39, 8698-8704. The Aβ present in a homogenous sample containing membranes can be detected by timer-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark. Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plants or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantities of Aβ is described elsewhere (Roberts, S. B.; Hendrick, J. P.; Vinitsky, A.: Lewis, M.; Smith, D. W.; Pak, R. PCT Publication WO 01/0175435; Shearman, M.; Beher, D. et al., *Biochemistry*, 2000, 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors administered to animals and Aβ levels in multiple compartments, such as plasma, cerebral spinal fluid, and brain extracts, are monitored from Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CFS are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 1,000, 000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or times release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well know to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chose route of administration and standard pharmaceutical practice.

The dosage regimen for the compounds of the present application will, of course, vary depending upon known factors, such as the pharmacodynamic characteristics of the particular agent and its more and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinary skilled physician or veterinarian can readily determine and prescribe the effective amount of the drug required to prevent, counter, or arrest the progress of the condition.

Advantageously, compounds of the present application may be administered in a single daily does, or the total daily dosage may be administered in divided doses of two, three, or four times daily.

The compounds for the present application can be administered in intranasal form via topical use of suitable intranasal vehicles or via transdermal routes, using those forms of transdermal skin patches well known to those of ordinary skill in that art. To be administered in the form of a transdermal delivery system, the dosage administration will, or course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitable selected with respect to the invented form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxylmethylcellulose, polyethylene glycol, waxes, and the like. Lubricants used in these dosage forms include sodium oleate, sodium stearate, magnesium stearate, sodium benzoate, sodium acetate, sodium chloride and the like. Disintegrators includes, without limitations, starch, methyl cellulose, agar, bentonite, xanthan gum, and the like.

The compounds of the present disclosure can also be administered in the form of liposome delivery systems, such as small unilamellar vesicles, large unilamellar vesicles, and multilamellar vesicles. Liposomes can be formed from a variety of phospholipids, such as cholesterol, stearylmine, or phosphatidylcholines.

Compounds of the present disclosure may also be coupled with soluble polymers as targetable drug carriers. Such polymers can include poylvinylpyrrolidone, pyran copolymer, polyhdryoxypropylmethacrylamidephenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polyactic acid, polyglycolic acid, copolymers of polyactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask for any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parental solutions. Solutions for parenteral administration preferably contain water soluble salt of the active ingredient, suitable stabilizing agents, and if necessary, buffer substances. Antioxidizing agents such as sodium bisulfide, sodium sulfite, or ascorbic acid, either alone or combined, are suitable stabilizing agents. Also used are citric acid and its salts and sodium EDTA. In addition, parental solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. The compound having formula (Id); or a stereoisomer thereof,

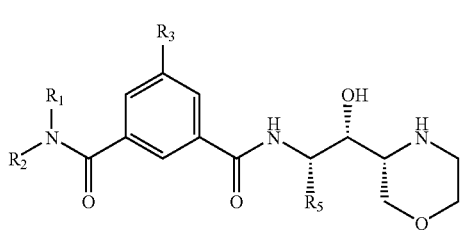

wherein $R_1$ is hydrogen or $C_{1-6}$alkyl;

$R_2$ is $C_{1-6}$alkyl or phenyl($C_{1-4}$alkyl) in which said phenyl is optionally substituted with halogen; or $R_1$ and $R_2$ are joined together with the nitrogen to form a 5- or 6-membered ring optionally substituted by $R_4$;

$R_3$ is hydrogen, $C_{1-6}$alkyl, oxazole, thiazole, or $NR_{12}$—(CO)—$R_{13}$ in which $R_{12}$ and $R_{13}$ are independently $C_{1-6}$alkyl or are joined together with the nitrogen to form a 5- or 6-membered ring;

$R_4$ is $C_{1-4}$alkyl optionally substituted with $C_{1-4}$alkoxy; and $R_5$ is $C_{1-6}$alkyl or phenyl($C_{1-4}$alkyl) in which each group is optionally substituted with one or two halogen;

or a nontoxic pharmaceutically acceptable salt thereof.

2. The compound, or a stereoisomer thereof, which is N-((1R,2S)-3-(3,5-difluorophenyl)-1-hydroxy-1-((2R,4R)-4-propoxypyrrolidin-2-yl)propan-2-yl)-3-((R)-2-(methoxymethyl)pyrrolidine-1-carbonyl)-5-(oxazol-2-yl)benzamide.

* * * * *